(12) United States Patent
Grenning

(10) Patent No.: US 11,952,327 B2
(45) Date of Patent: *Apr. 9, 2024

(54) METHODS AND COMPOSITIONS FOR TERPENOID SYNTHESIS

(71) Applicant: University of Florida Research Foundation, Inc., Gainesville, FL (US)

(72) Inventor: Alexander James Grenning, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 419 days.

This patent is subject to a terminal disclaimer.

(21) Appl. No.: 16/333,728

(22) PCT Filed: Sep. 15, 2017

(86) PCT No.: PCT/US2017/051870
§ 371 (c)(1),
(2) Date: Mar. 15, 2019

(87) PCT Pub. No.: WO2018/053322
PCT Pub. Date: Mar. 22, 2018

(65) Prior Publication Data
US 2019/0270700 A1    Sep. 5, 2019

Related U.S. Application Data

(60) Provisional application No. 62/394,852, filed on Sep. 15, 2016.

(51) Int. Cl.
| | |
|---|---|
| *C07C 253/30* | (2006.01) |
| *C07B 37/02* | (2006.01) |
| *C07C 255/31* | (2006.01) |
| *C07C 255/47* | (2006.01) |
| *C07C 403/18* | (2006.01) |
| *C07D 221/22* | (2006.01) |
| *C07D 307/94* | (2006.01) |
| *C07D 311/94* | (2006.01) |
| *C07D 317/72* | (2006.01) |

(52) U.S. Cl.
CPC .......... *C07C 253/30* (2013.01); *C07B 37/02* (2013.01); *C07C 255/31* (2013.01); *C07C 255/47* (2013.01); *C07C 403/18* (2013.01); *C07D 221/22* (2013.01); *C07D 307/94* (2013.01); *C07D 311/94* (2013.01); *C07D 317/72* (2013.01); *C07C 2601/14* (2017.05); *C07C 2601/16* (2017.05); *C07C 2602/30* (2017.05); *C07C 2602/32* (2017.05); *C07C 2602/34* (2017.05); *C07C 2603/30* (2017.05)

(58) Field of Classification Search
CPC .... C07C 253/30; C07C 255/31; C07C 255/47
See application file for complete search history.

(56) References Cited

PUBLICATIONS

Foster et al. J. Am. Chem. Soc. 1947, 69, 1893-1896 (Year: 1947).*
Cope et al. J. Am. Chem. Soc. 1941, 63, 1843-1852 (Year: 1941).*
Vanderwerf et al. Organic Syntheses 1955, Coll. vol. 3, p. 44 (Year: 1955).*
MacLeod et al. Australian Journal of Chemistry 1990, 43, 1309-1326 (Year: 1990).*
Kamijo et al. Tetrahedron Letters 2016, 57, 137-140 (Year: 2015).*
Mishriky et al. J. Chem. Research (S), 1997, 316-317 (Year: 1997).*
Lahtigui et al. Angew. Chem. Int. Ed. 2016, 55, 15792-15796 (Year: 2016).*
Liu et al., Enantioselective γ-Alkylation of α,β-Unsaturated Malonates and Ketoesters by a Sequential Ir-Catalyzed Asymmetric Allylic Alkylation/Cope Rearrangement, J Am Chem Soc. 138(16): 5234-5237, 2016.
Vertesalijai et al., Knoevenagel Adducts as Trimethylenemethane Dipole Surrogates, Angewandte Chemie International Edition, vol. 55, Issue 1, 317-320, 2016.
Maimone et al., Modern synthetic efforts toward biologically active terpenes, Nature Chemical Biology, vol. 3, 396-407, 2007.
Hong et al., The Contruction of All-Carbon Quatemary Stereocenters by Use of Pd-Catalyzed Asymmetric Allyllc Alkylation Reactions in Total Synthesis, European J Org Chem., vol. 2013(14), 2745-2759, 2013.
Sheth, Asymmetric Synthesis of Natural Products and Medicinal Drugs Through One-Pot-Reaction Strategies, Synthesis, vol. 47, pp. A-AC, 2015.
International Search Report issued for PCT/US2017/051870, dated Dec. 1, 2017.

* cited by examiner

*Primary Examiner* — Matthew P Coughlin
(74) *Attorney, Agent, or Firm* — Thomas Horstemeyer LLP.

(57) ABSTRACT

In one aspect, the disclosure relates to methods for preparation of terpene and terpene-like molecules. In a further aspect, the disclosure relates to the products of the disclosed methods, i.e., terpene and terpene-like molecules prepared using the disclosed methods. Intermediates for the synthesis of a wide variety of terpenoids are γ-allyl Knoevenagel adducts or quasi γ-allyl Knoevenagel adducts are disclosed. In various aspects, methods of preparing terpenoids through these intermediates are disclosed. The methods can comprise α-alkylation of an allylic electrophile followed by ring-closure metathesis to a polycyclic terpenoid structure. In a further aspect, the disclosure pertains to terpenoid frameworks, and compounds prepared via disclosed oxidation and substitution reactions on the disclosed terpenoid frameworks. This abstract is intended as a scanning tool for purposes of searching in the particular art and is not intended to be limiting of the present disclosure.

19 Claims, 18 Drawing Sheets

Knoevenagel adducts 5a – 5g
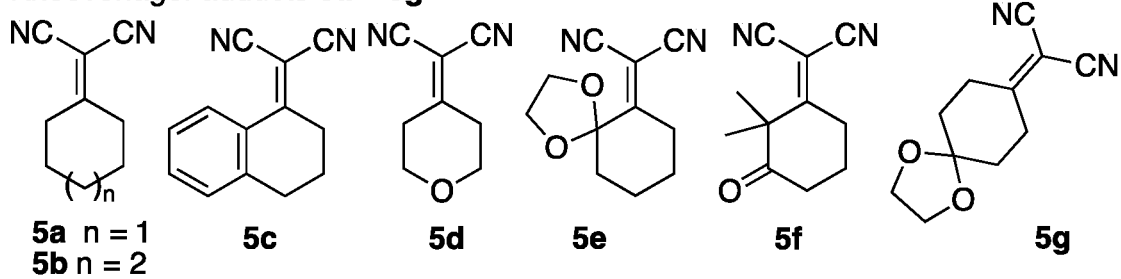
allylic electrophile 2a – 2g
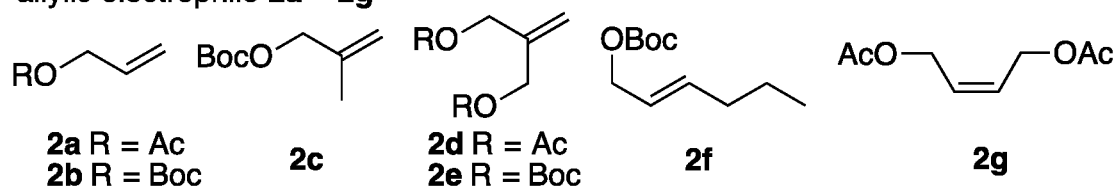
1,3-dicarbonyl nucleophiles 7a – 7g
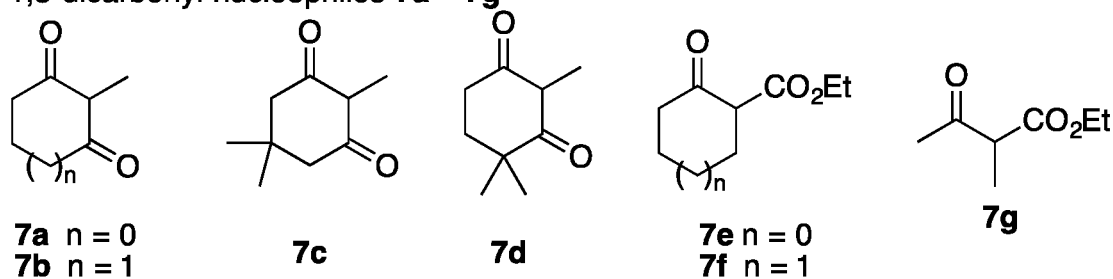
FIG. 5

FIG. 6 (continues onto next page)

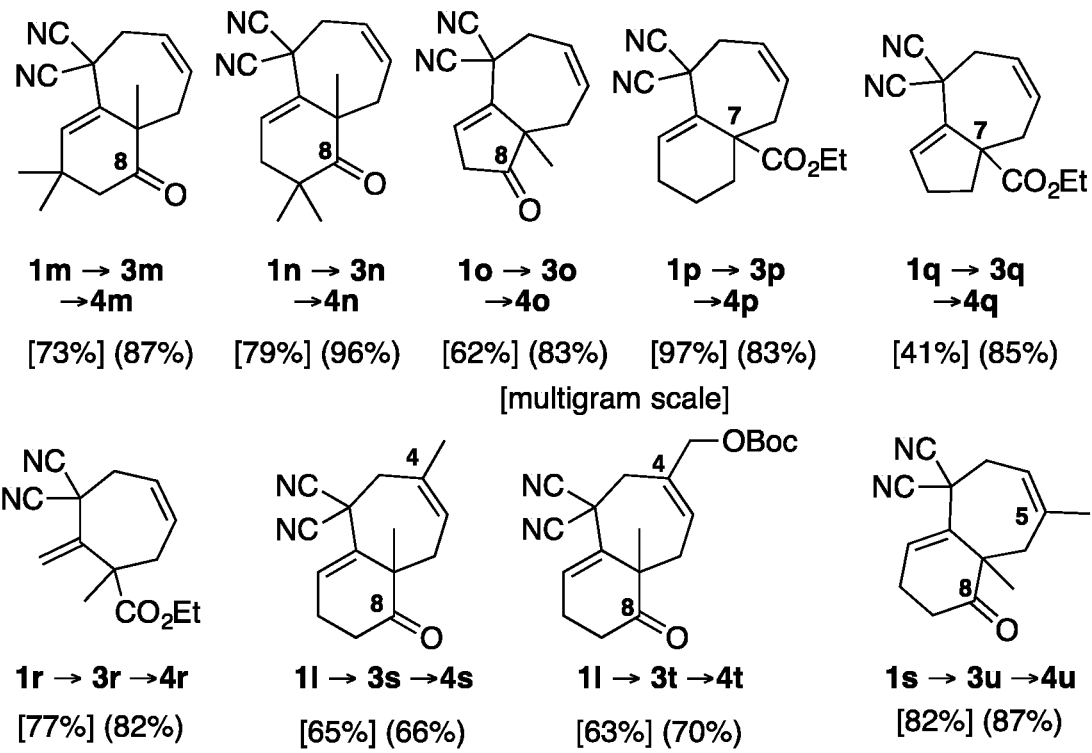
i. 1.05 equiv. allyl carbonate, 1 mol% Pd(PPh$_3$)$_4$, THF, rt.
ii. 1 – 5 mol% Grubbs II, toluene, 80-100°C.
FIG. 6 (continued from previous page)
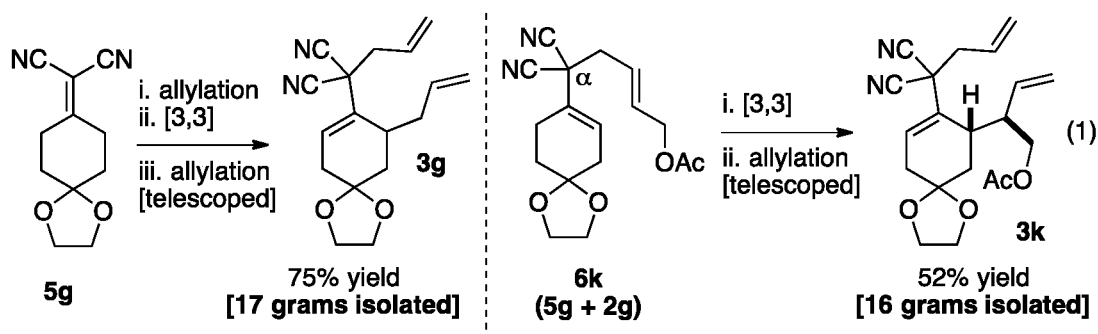
FIG. 7

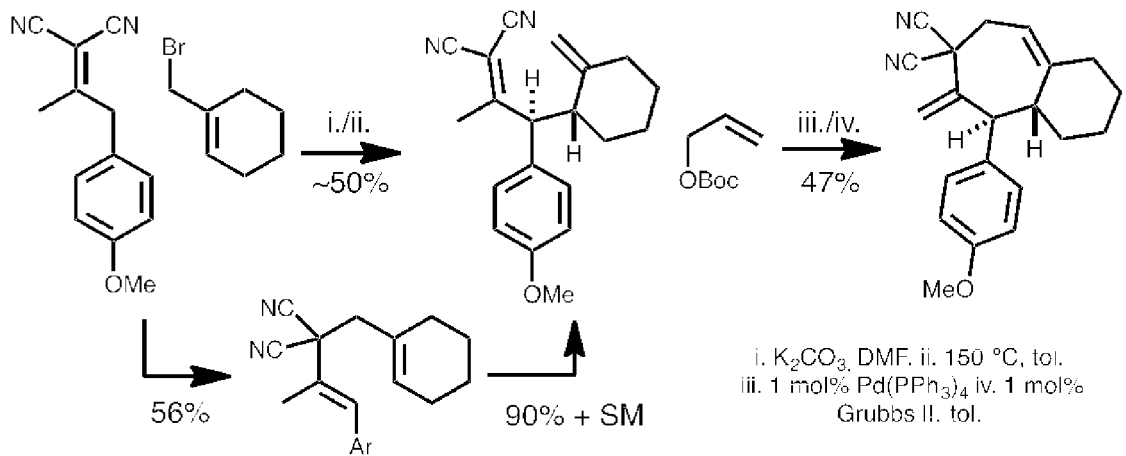
FIG. 19
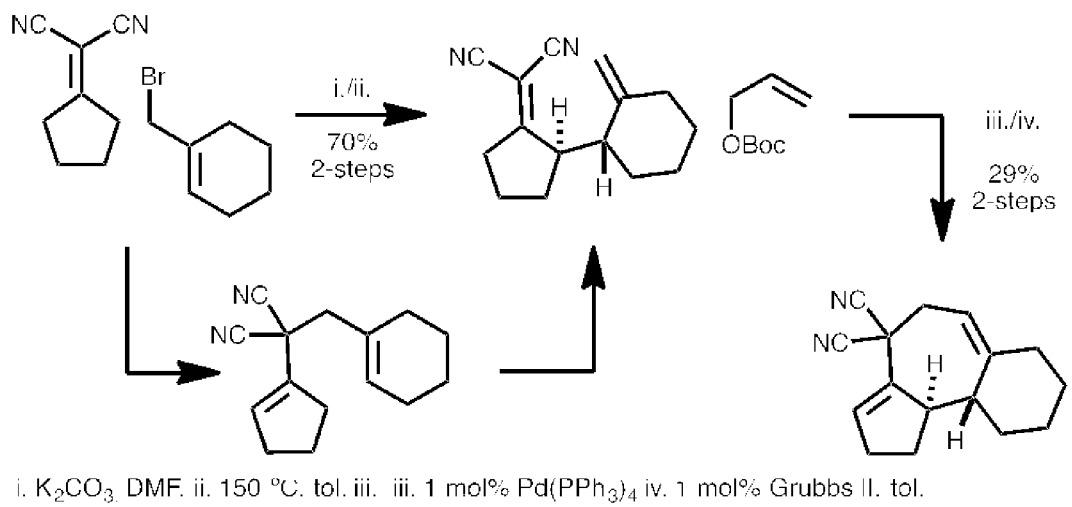
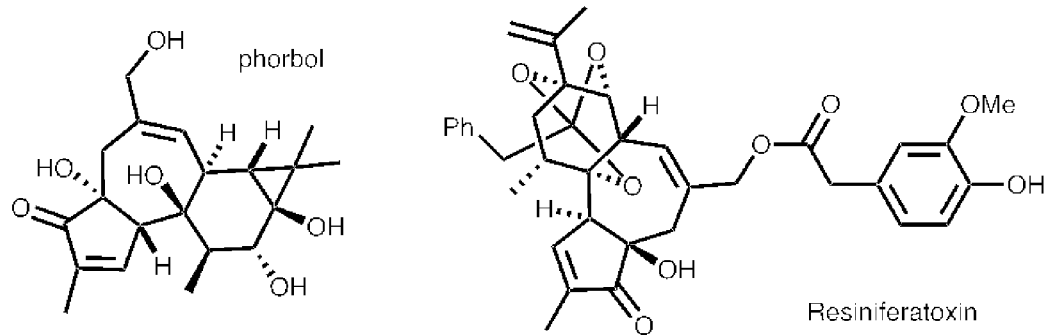
FIG. 20

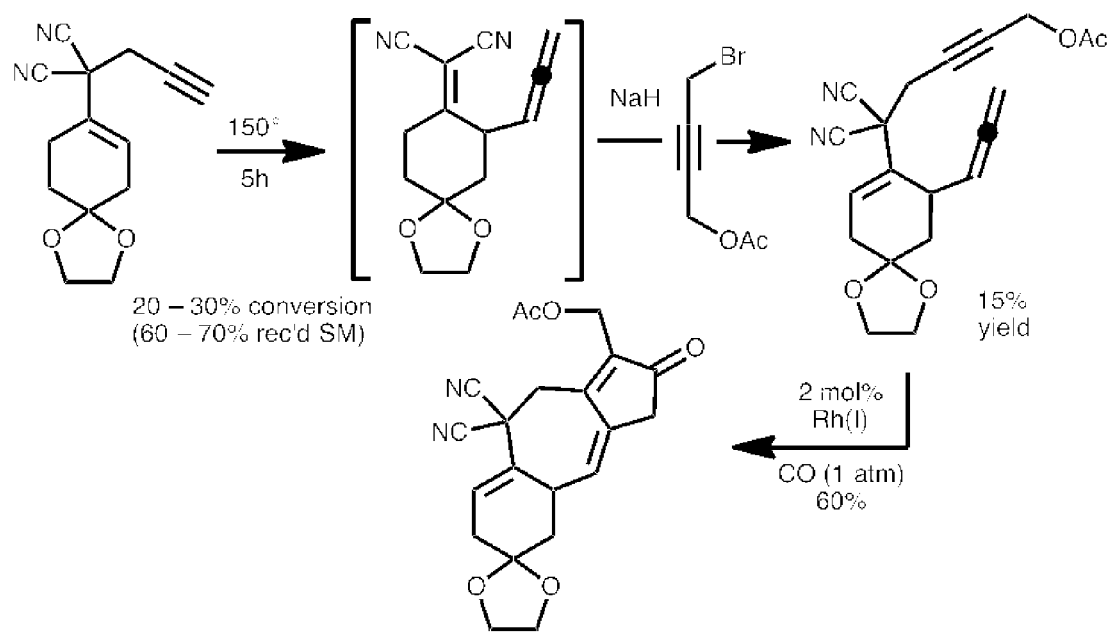
FIG. 21
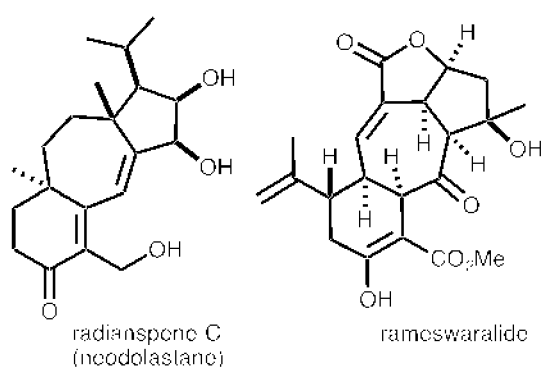
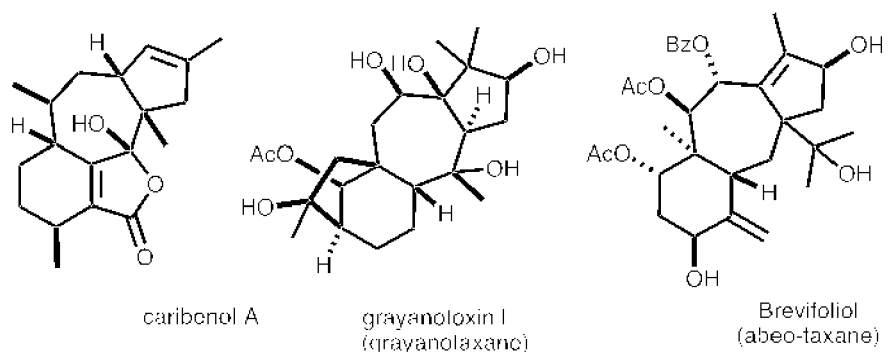
FIG. 22 i. NH$_4$OAc, PhH:AcOH, ii. allyl bromide, K$_2$CO$_3$ iii. 1 mol% Grubbs II, iv. MeOK, MeOH, v. CuO (cat.)

METHODS AND COMPOSITIONS FOR TERPENOID SYNTHESIS

CROSS-REFERENCE TO RELATED APPLICATIONS

This application is a National Phase Application of International Application No. PCT/US2017/051870, filed Sep. 25, 2017, which claims the benefit of U.S. Provisional Application No. 62/394,852, filed on Sep. 15, 2016, which applications are incorporated herein by reference in their entirety.

BACKGROUND

Structurally complex terpenoid natural products have been recognized as important therapeutic agents. Many terpenoid natural products contain a polycyclic core bearing a medium-sized 7- to 9-membered ring; examples of which are illustrated in FIG. 1. For example, taxol and ingenol are clinically used for the treatment of cancer and actinic keratosis, respectively. In addition to these important drugs, a multitude of related cycloheptane-containing terpenoid natural products have promising, but underexplored medicinal potential. For instance, englerin A and its analogs are being actively investigated for the treatment of renal cancer, phorbol and its esters have been intensely studied due to their potent biological activities, as have pseudoguaianolide natural products. Numerous other natural product classes, including abeo-taxane, neodolastane, cyathane, and icetexane, and individual natural products, such as anthecularin, sandresolide B, frondosin A, and liphagal display promising biological activities. The combination of the polycyclic carbon-framework's rigidity and differences resulting from the substitution and oxidation patterns thereon provide a rich array of potential biological activities. Facile and systematic access to diverse substitution and oxidation patterns about carbocyclic frameworks would advance drug design and development.

Some of the most common synthetic strategies involve ring-closing metathesis, cycloaddition, or cycloisomerization of linear precursors, as illustrated in FIG. 2. For example, intramolecular [5+2] cycloisomerization, [3+2+2] cycloisomerization, the allenyne-Pauson-Khand reaction, [4+3] cycloaddition and [4+2] cycloaddition allow assembly of terpenoid frameworks. "Cyclase/oxidase phase logic," where chemical synthesis mimics a biosynthesis employing a cyclase followed by an oxidase mediated transformation is an effective synthetic philosophy for terpene and terpenoid analog synthesis, often referred to as a "two-phase terpene synthesis". Two-phase terpene synthesis is attractive because unique placements of oxygen atoms can result where in other strategies placement is inaccessible. Nevertheless, terpenoid synthesis via cyclase/oxidase phase logic remains little explored for the preparation of natural products and analogs, which may provide many new and useful drugs. To this end, an effective method of forming a terpene or terpene-like compound through intermediates that are readily differentiated by substitution and base ring-size that can promote a second ring formation that provides or enables further substitution remains a challenge. A synthetic tactic, in addition to those highlighted above, that allows systematic placement of oxygen atoms and other functional groups about common terpenoid frameworks by a tunable strategy is desired. Particularly desirable is a method where a robust and simple reaction sequence can employ readily available reagent-classes to yield unique terpenoid architectures.

Despite advances in synthetic methods for preparation of terpene and terpene-like compounds, there remains a scarcity of synthetic methods that permit simple, scalable, and tunable preparation of these types of molecules. Moreover, there remains a scarcity of synthetic methods for terpene and terpene-like compounds that utilize abundantly available reagent classes such as cycloalkanones, malononitriles, and allylic electrophiles. These needs and other needs are satisfied by the present disclosure.

SUMMARY

In accordance with the purpose(s) of the disclosure, as embodied and broadly described herein, the disclosure, in one aspect, relates to methods for preparation of terpene and terpene-like molecules. In a further aspect, synthetic intermediates for the synthesis of a wide variety of terpenoids are disclosed which comprise γ-allyl Knoevenagel adducts or quasi γ-allyl Knoevenagel adducts are disclosed. In various aspects, methods of preparing terpenoids through these intermediates are disclosed. In a still further aspect, the methods can comprise α-alkylation of an allylic electrophile followed by ring-closure metathesis to a polycyclic terpenoid structure.

In a further aspect, the disclosure relates to γ-allyl Knoevenagel adducts or quasi γ-allyl Knoevenagel adducts prepared by the disclosed methods. In a still further aspect, the disclosure relates to the products of the disclosed methods, such as terpene and terpene-like molecules prepared using the disclosed methods. In a yet further aspect, the disclosure pertains to terpenoid frameworks, and compounds prepared via disclosed oxidation and substitution reactions on the disclosed terpenoid frameworks.

Disclosed are methods of synthesizing a terpenoid framework, comprising: providing a γ-allyl Knoevenagel adduct or a quasi γ-allyl Knoevenagel adduct of the structure:

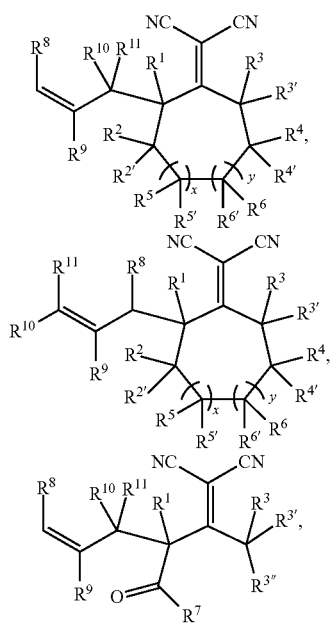

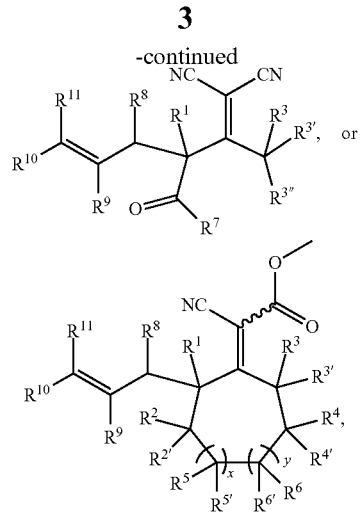

wherein x and y are independently 0 or 1; wherein R, is $C_1$ to $C_6$ alkyl or $C_1$ to $C_6$ alkoxy; wherein $R^1$, $R^2$, $R^{2'}$, $R^3$, $R^{3'}$, $R^{3''}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_6$ to $C_{12}$ alkatrieneyl, $C_3$ to $C_8$ cycloalkanyl, $C_3$ to $C_8$ cycloalkenyl, $C_1$ to $C_{12}$ alkoxy, phenoxy, acetoxy, or phenyl; wherein one or more of $R^2$ with $R^{2'}$, $R^3$ with $R^{3'}$, $R^3$, $R^4$ with $R^{4'}$, $R^5$ with $R^{5'}$, and $R^6$ with $R^{6'}$ is optionally combined as carbonyl, ethylenyl, $C_3$ to $C_8$ cycloalkyl, $C_3$ to $C_5$ cycloalkenyl, $C_5$ to $C_6$ heterocycle containing one or more oxygens; wherein one or more of $R^{2'}$ with $R^{5'}$, $R^{3'}$ with $R^{4'}$, $R^{4'}$ with $R^{6'}$, and $R^{5'}$ with $R^{6'}$ is optionally combined as a π-bond or a π-bond with $R^2$ with $R^5$, $R^3$ with $R^4$, $R^4$ with $R^6$, and/or $R^5$ with $R^6$ combined as an aromatic ring, $C_5$ or $C_6$ cycloalkene, or $C_5$ or $C_6$ cycloalkadiene, and where each of $R^2$, $R^3$, $R^4$, $R^5$, and $R^6$ is combined only once; wherein one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or wherein $R^4R^{4'}C$, $R^5R^{5'}C$ or $R^6R^{6'}C$ can be replaced with an oxygen; and wherein any of the alkyls, alkylenyl, alkadienyl, alkatrienyl, cycloalkyl, cycloalkenyl, alkoxy, phenoxy, aryl, and alkylene chain is optionally substituted with one or more $C_1$ to $C_4$ alkyl, $C_1$ to $C_4$ alkoxy, $C_3$ to $C_6$ cycloalkyl, $C_3$ to $C_6$ cycloalkenyl, phenyl, acetyl, or nitro groups; and wherein $R^8$ is H, phenyl or the oxygen of an oxo group, $R^9$, $R^{10}$, and $R^{11}$ are independently H, $CH_2X$, $C_1$ to $C_{12}$ alkyl, or phenyl, or wherein $R^9$ and $R^{10}$ are combined as a $C_5$ or $C_6$ cycloalkene or phenyl, wherein the $C_1$ to $C_{12}$ alkyl, phenyl, or $C_5$ or $C_6$ cycloalkene can be further substituted with one or more Br, Cl, I, $C_1$ to $C_4$ alkoxy, or where two adjacent carbons are substituted by methylenedioxy.

In an aspect, disclosed are compounds having the structure:

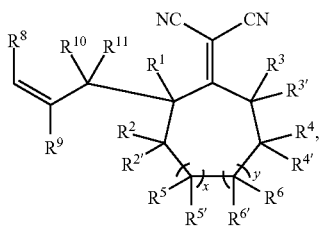

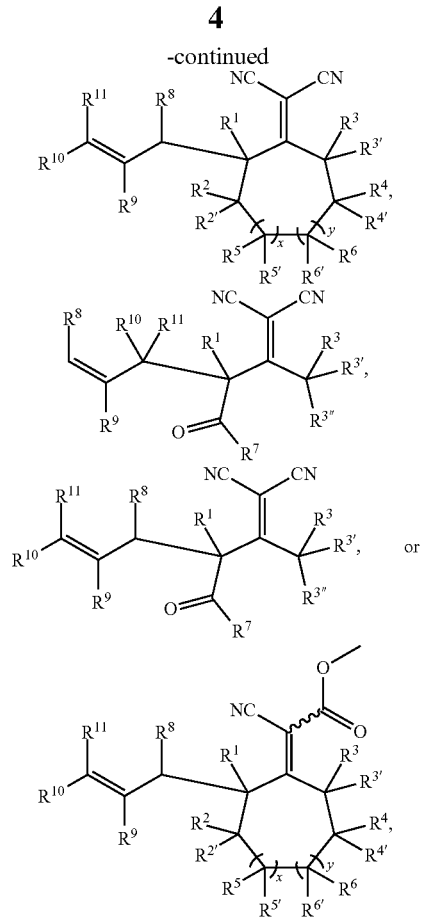

wherein x and y are independently 0 or 1; wherein R, is $C_1$ to $C_6$ alkyl or $C_1$ to $C_6$ alkoxy; wherein $R^1$, $R^2$, $R^{2'}$, $R^3$, $R^{3'}$, $R^{3''}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_6$ to $C_{12}$ alkatrieneyl, $C_3$ to $C_8$ cycloalkanyl, $C_3$ to C cycloalkenyl, $C_1$ to $C_{12}$ alkoxy, phenoxy, acetoxy, or phenyl; wherein one or more of $R^2$ with $R^{2'}$, $R^3$ with $R^{3'}$, $R^{3''}$, $R^4$ with $R^{4'}$, $R^5$ with $R^{5'}$, and $R^6$ with R6' is optionally combined as carbonyl, ethylenyl, $C_3$ to C cycloalkyl, $C_3$ to C cycloalkenyl, $C_5$ to $C_6$ heterocycle containing one or more oxygens; wherein one or more of $R^{2'}$ with $R^{5'}$, $R^{3'}$ with $R^{4'}$, $R^{4'}$ with $R^{5'}$, and $R^{5'}$ with $R^{6'}$ is optionally combined as a π-bond or a π-bond with $R^2$ with $R^5$, $R^3$ with $R^4$, $R^4$ with $R^6$, and/or $R^5$ with $R^5$ combined as an aromatic ring, $C_5$ or $C_6$ cycloalkene, or $C_5$ or $C_6$ cycloalkadiene, and where each of $R^2$, $R^3$, $R^4$, $R^5$, and $R^6$ is combined only once; wherein one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or $R^4R^{4'}C$, $R^5R^{5'}C$ or $R^6R^{6'}C$ can be replaced with an oxygen; and wherein any of the alkyls, alkylenyl, alkadienyl, alkatrienyl, cycloalkyl, cycloalkenyl, alkoxy, phenoxy, aryl, and alkylene chain is optionally substituted with one or more $C_1$ to $C_4$ alkyl, C, to $C_4$ alkoxy, $C_3$ to $C_6$ cycloalkyl, $C_3$ to C cycloalkenyl, phenyl, acetyl, or nitro groups; and wherein $R^a$ is H, phenyl or the oxygen of an oxo group, $R^9$, $R^{10}$, and $R^{11}$ are independently H, $CH_2X$, $C_1$ to $C_{12}$ alkyl, or phenyl, or wherein $R^9$ and $R^{10}$ are combined as a $C_5$ or $C_6$ cycloalkene or phenyl, wherein the $C_1$ to $C_{12}$ alkyl, phenyl, or $C_5$ or $C_6$ cycloalkene can be further substituted with one or more Br, Cl, I, $C_1$ to $C_4$ alkoxy, or where two adjacent carbons are substituted by methylenedioxy. In various aspects, the disclosed compounds are γ-allyl Knoevenagel adducts or quasi γ-allyl Knoevenagel adducts prepared using the disclosed methods.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the disclosure.

FIG. 5 shows exemplary reagents used to prepare the γ-allyl Knoevenagel adducts, according to aspects of the invention.

FIG. 7 show reaction schemes for the telescoping synthesis of α,γ-diallyl Knoevenagel adducts, according to an aspect of the invention.

FIG. 19 shows a reaction scheme where malononitrile-conjugation acts as a driving force for [3,3] rearrangement, according to an aspect of the invention.

FIG. 20 shows a reaction scheme where cyclic-allylic electrophiles yield tricycle alkanes and target terpenes having the tricyclic structure according to an aspect of the invention.

FIG. 21 shows a reaction scheme where 1,5-enyne [3,3] rearrangement yields a 6/7/5 diterpenoid structure, according to an aspect of the invention.

FIG. 22 shows the structure of various terpene-like ring structures accessible by the reaction scheme of FIG. 21, according to an aspect of the invention.

Figure 1:
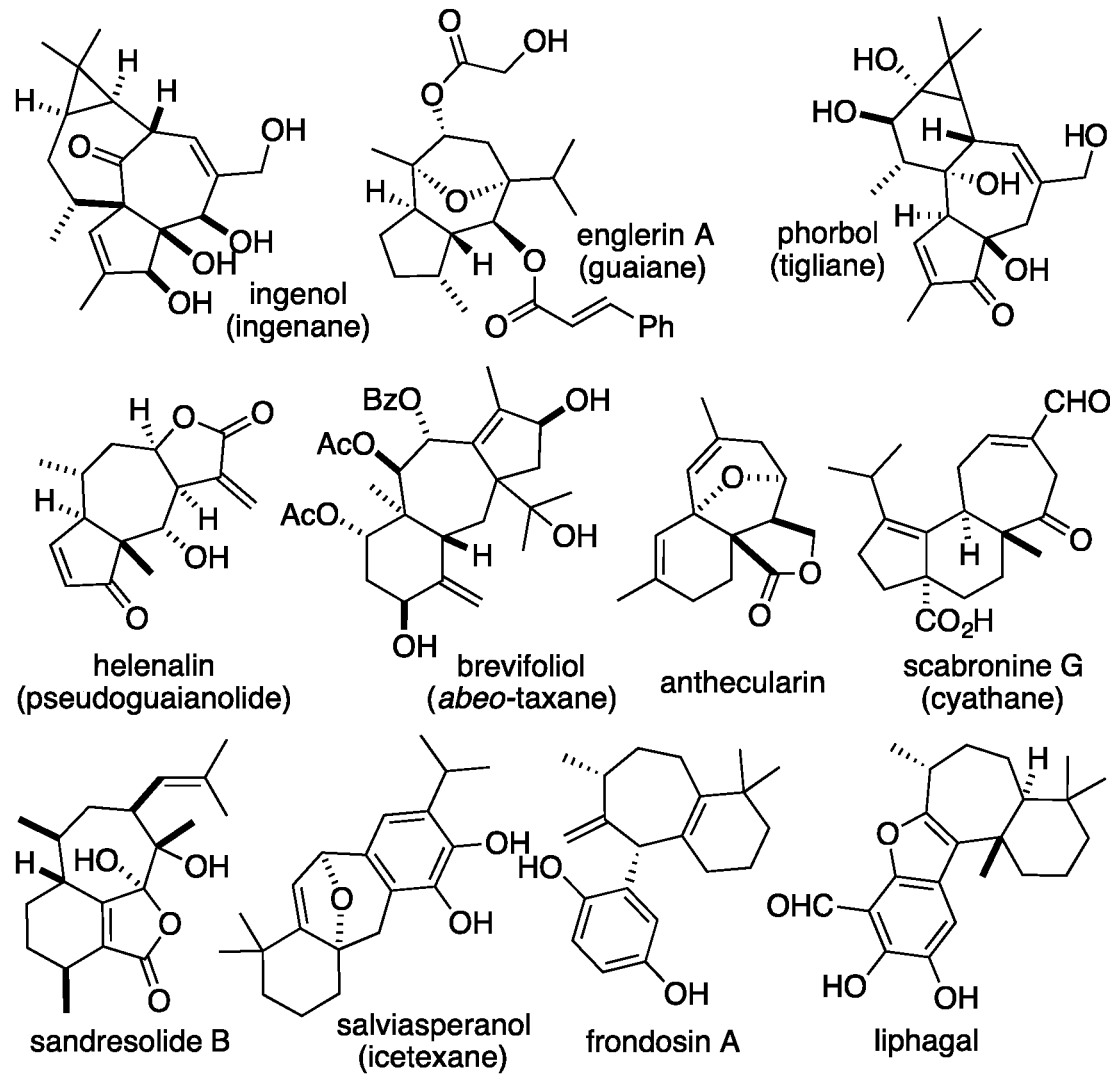
FIG. 1 shows representative medium-sized ring containing terpenoid natural products.
Figure 2:
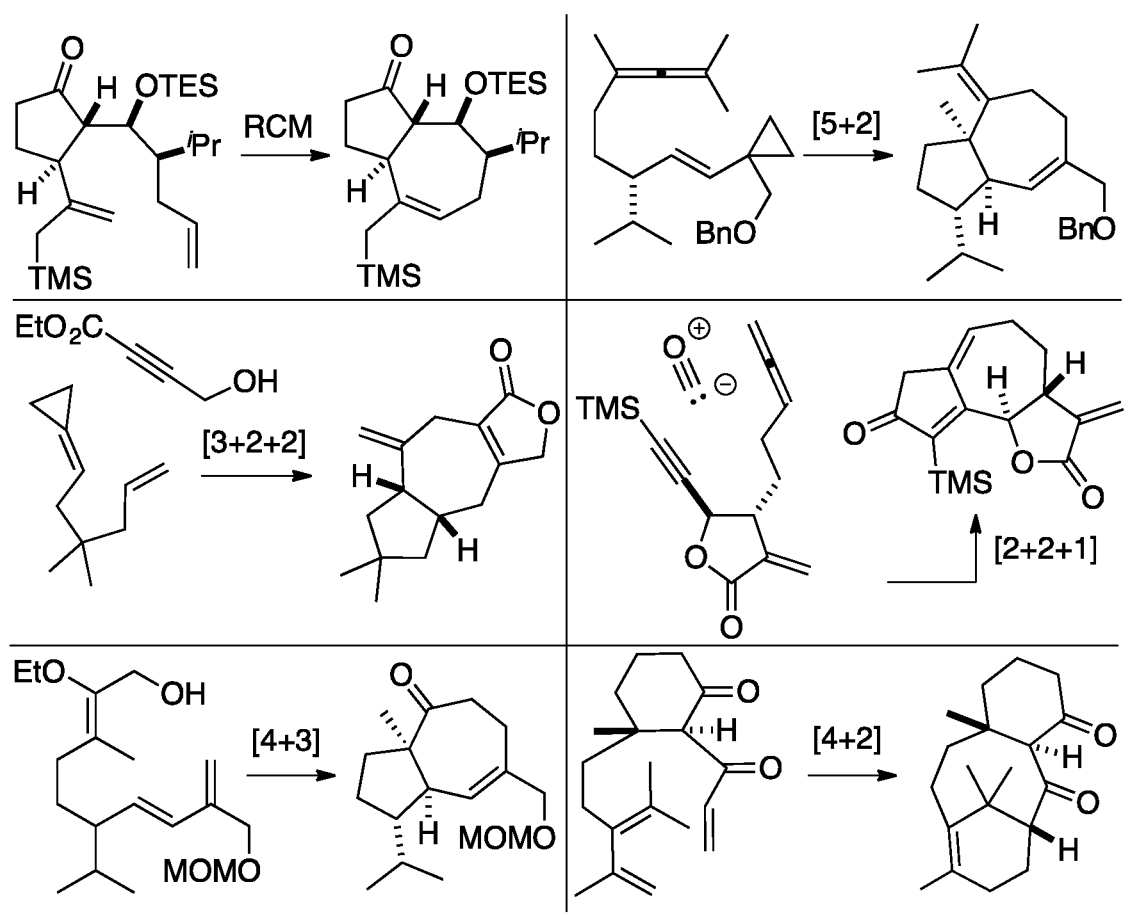
FIG. 2 shows state of the art cyclization routes toward terpenoid polycycloalkane synthesis.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

DETAILED DESCRIPTION

The present disclosure can be understood more readily by reference to the following detailed description of the disclosure and the Examples included therein.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

Unless otherwise expressly stated, it is in no way intended that any method set forth herein be construed as requiring that its steps be performed in a specific order.

Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

B. Compounds

In one aspect, the disclosure relates to compounds prepared using the disclosed methods. In a further aspect, the disclosure relates to γ-allyl Knoevenagel adducts, quasi γ-allyl Knoevenagel adducts, or equivalents prepared by the disclosed methods. In a still further aspect, the disclosure relates to the products of the disclosed methods, such as terpene and terpene-like molecules prepared using the disclosed methods. In a yet further aspect, the disclosure pertains to terpenoid frameworks, and compounds prepared via disclosed oxidation and substitution reactions on the disclosed terpenoid frameworks.

In aspects of the invention, the γ-allyl Knoevenagel adduct 1 or quasi γ-allyl Knoevenagel adduct can have the structure:

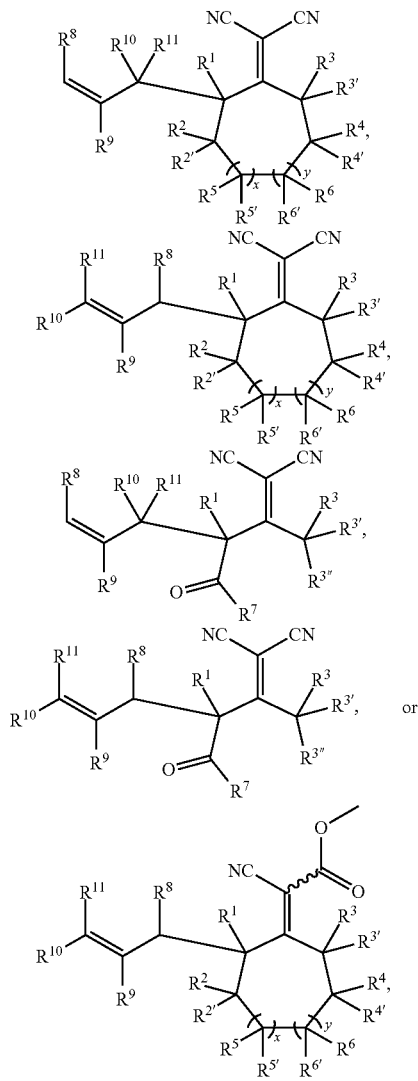

wherein: x and y are independently 0 or 1; wherein R, is $C_1$ to C alkyl or $C_1$ to $C_6$ alkoxy; wherein $R^1$, $R^2$, $R^{2'}$, $R^3$, $R^{3'}$, $R^{3''}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_e$ to $C_{12}$ alkatrieneyl, $C_3$ to $C_8$ cycloalkanyl, $C_3$ to $C_8$ cycloalkenyl, $C_1$ to $C_{12}$ alkoxy, phenoxy, acetoxy, or phenyl; any one or more of $R^2$ with $R^{2'}$, $R^3$ with $R^{3'}$, $R^{3''}$, $R^4$ with $R^{4'}$, $R^5$ with $R^{5'}$, and $R^8$ with $R^6$ is optionally combined as carbonyl, ethylenyl, $C_3$ to $C_8$ cycloalkyl, $C_3$ to $C_8$ cycloalkenyl, $C_5$ to $C_6$ heterocycle containing one or more oxygens; any one or more of $R^{2'}$ with $R^5$, $R^3$ with $R^{4'}$, $R^{4'}$ with $R^{6'}$, and $R^{5'}$ with $R^6$ is optionally combined as a π-bond or a π-bond with $R^2$ with $R^5$, $R^3$ with $R^4$, $R^4$ with $R^6$, and/or $R^5$ with $R^6$ combined as an aromatic ring, $C_5$ or $C_6$ cycloalkene, or $C_5$ or $C_6$ cycloalkadiene, and where each of $R^2$, $R^3$, $R^4$, $R^5$, and $R^6$ is combined only once; one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or any one of $R^4R^{4'}C$, $R^5R^{5'}C$ or $R^6R^{6'}C$ can be replaced with an oxygen; and wherein any of the alkyls, alkylenyl, alkadienyl, alkatrienyl, cycloalkyl, cycloalkenyl, alkoxy, phenoxy, aryl, and alkylene chain is optionally substituted with one or more $C_1$ to $C_4$ alkyl, $C_1$ to $C_4$ alkoxy, $C_3$ to $C_6$ cycloalkyl, $C_3$ to $C_6$ cycloalkenyl, phenyl, acetyl, or nitro groups; and wherein $R^8$ is H, phenyl or the oxygen of an oxo group, $R^9$, $R^{10}$, and $R^{11}$ are independently H, $CH_2X$, $C_1$ to $C_{12}$ alkyl, or phenyl, or wherein $R^9$ and $R^{10}$ are combined as a $C_5$ or $C_6$ cycloalkene or phenyl, wherein the $C_1$ to $C_{12}$ alkyl, phenyl, or $C_5$ or $C_6$ cycloalkene can be further substituted with one or more Br, Cl, I, $C_1$ to $C_4$ alkoxy, or where two adjacent carbons are substituted by methylenedioxy.

The γ-allyl Knoevenagel adduct 1 are derived from a ketone that is converted by reaction with malononitrile to a Knoevenagel adduct followed by γ-allylation that can be direct or via α-allylation followed by [3,3] sigmatropic rearrangement depending upon the structure of the Knoevenagel adduct and the allyl electrophile employed. The quasi γ-allyl Knoevenagel adduct is formed by allylation of the ketone followed by reaction of the ketone with $CNCH_2C(O)OCH_3$. The ketones that can be used have the structure:

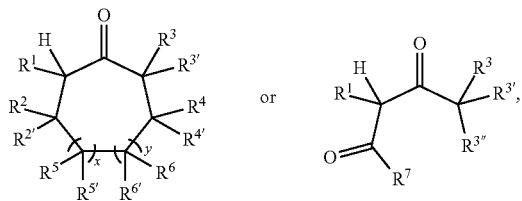

wherein the identity of x, y, and $R^1$, $R^2$, $R^{2'}$, $R^3$, $R^{3'}$, $R^{3''}$, $R^4$, $R^{4'}$, $R^5$, $R^{5'}$, $R^6$, $R^{6'}$, and $R^7$ are as above. The allyl electrophiles that can be used have the structure:

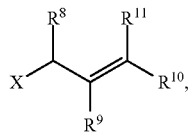

wherein $R^8$, $R^9$, $R^{10}$, and $R^{11}$ are defined as above and X is a leaving group selected from acetoxy, t-butyloxycarbonoxy, Cl, Br, I, trifluroacetoxy, or tosyl.

The intermediate terpenoid scaffolds 4, according to an aspect of the invention, bear a gem-dinitrile group at the 2-position of the carbocyclic framework. This group facilitates diversification of the polycyclic structure by subsequent synthetic transformations. Such quaternary dinitriles undergo decyanation by C—C cleavage and can be employed with other nucleophilic addition reactions. A nitrile functionality is sterically small (A value=0.17), displays metabolic stability, has decreased lipophilicity, and is isosteric to a halogen, such that the gem-dinitrile terpenoid analogs 4 can be considered potential bioactive compounds, according to an aspect of the invention.

Figure 4:
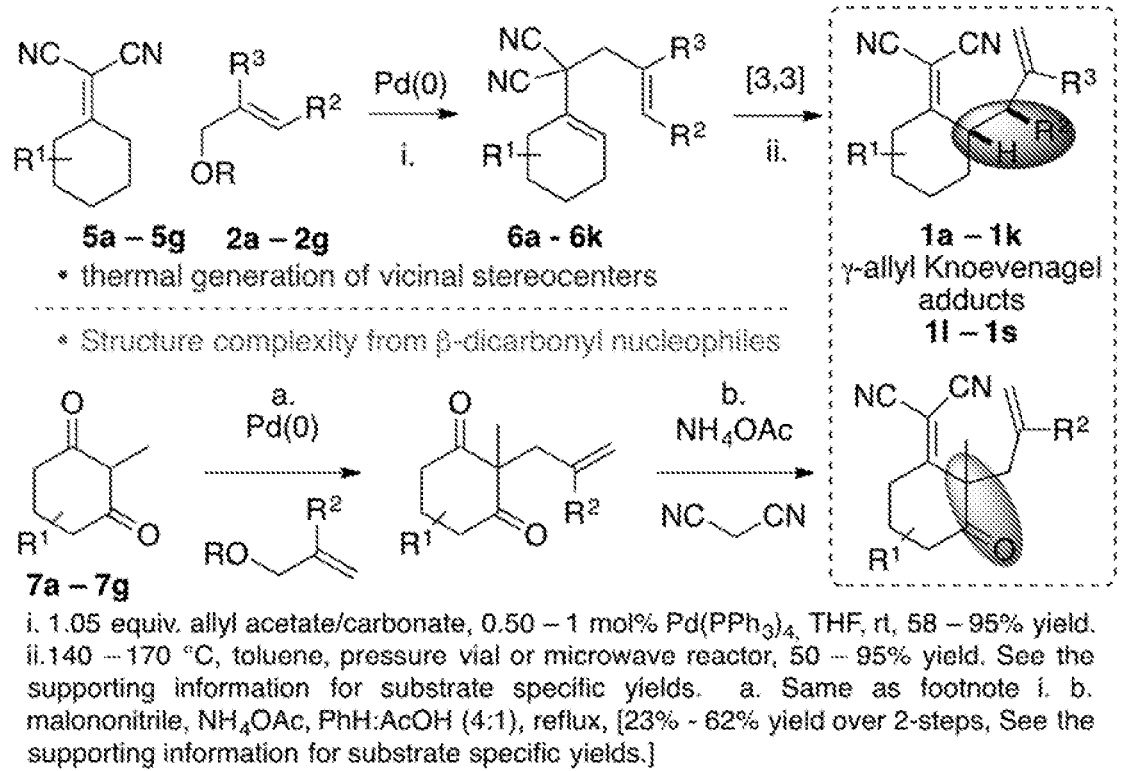
FIG. 4 shows reaction schemes for the synthesis of γ-allyl Knoevenagel adducts, according to aspects of the invention.

The γ-allyl Knoevenagel adducts 1, according to aspects of the invention, can be prepared by: an α-allylation/[3,3] sigmatropic rearrangement sequence of Knoevenagel adducts (5→6→1a-1k) derived from cyclic ketones and malononitrile, as illustrated with, but not limited to, cycloalkenone derived compounds; or by a sequence of allylation followed by Knoevenagel condensation to Knoevenagel adducts (7→11-1s) derived from commercially available β-dicarbonyl compounds, as illustrated with, but not limited to, 2-methyl-1,3-cyclohexan-dione or 2-ethylcarboxyl-cycloalkenone derived compounds, as shown in FIG. 4 top and bottom, respectively.

C. Methods of Preparing the Disclosed Compounds

In various aspects, the disclosure relates to methods for preparation of terpene and terpene-like molecules. In a further aspect, synthetic intermediates for the synthesis of a wide variety of terpenoids are disclosed which comprise γ-allyl Knoevenagel adducts or quasi γ-allyl Knoevenagel adducts are disclosed. In various aspects, methods of preparing terpenoids through these intermediates are disclosed. In a still further aspect, the methods can comprise α-alkylation of an allylic electrophile followed by ring-closure metathesis to a polycyclic terpenoid structure.

Aspects of the invention are directed to methods for formation of γ-allyl Knoevenagel adducts or equivalents that can be formed by various methods, as indicated for two of these methods in FIG. 4, and transformation of the γ-allyl Knoevenagel adducts into cycloheptene-containing terpenoid scaffolds by α-allylation/ring-closing metathesis sequence.

Depending on the choice of the ketone-derived Knoevenagel adduct and an allylic electrophile, substitution and oxidation patterns can be selectively generated and yield a unique terpenoid framework. In aspects of the invention, the synthesis of various 5/7 and 6/7 terpenoid cores are possible, including many that are in a high oxidation state. The method involves a gem-dinitrile and generates two alkenes, which can be chemoselectively transformed into other functionality to access many terpenoid analogs. The method, according to aspects of the invention, allows preparation of medium-sized ring terpenoid structures with controlled cycloalkane ring patterns and functional group incorporation at many of the positions about the polycycloalkane based on the functionalities included in the starting reagents for the γ-allyl Knoevenagel adducts and subsequent transformations thereof.

Figure 3A:
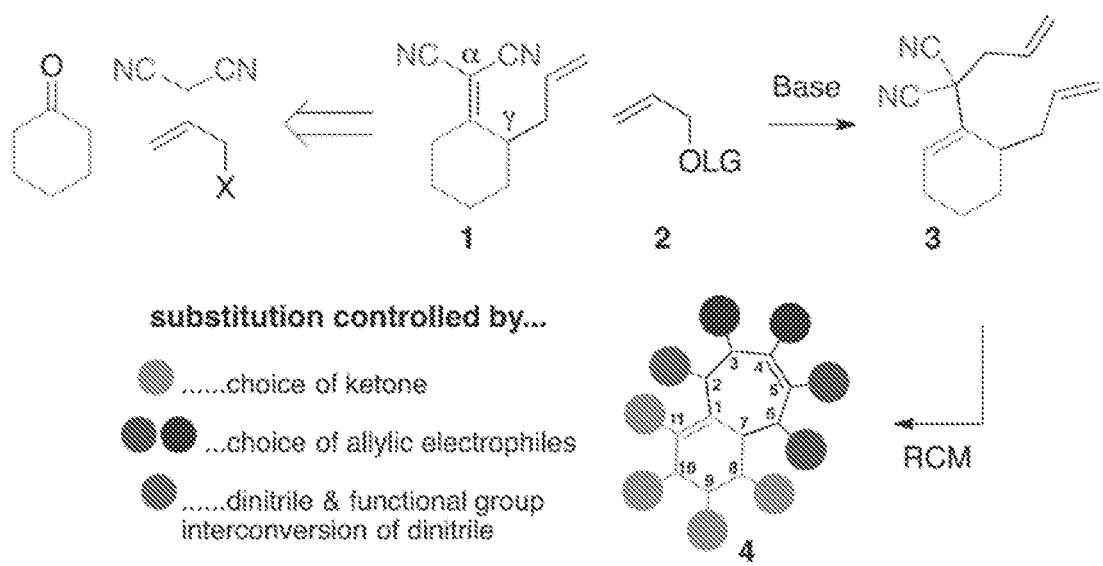
FIGS. 3A-3C illustrate common terpenoid cores that can be formed from cycloalkanones, malononitrile, and allylic electrophiles employing synthetic methods according to aspects of the invention.
Figure 3B:
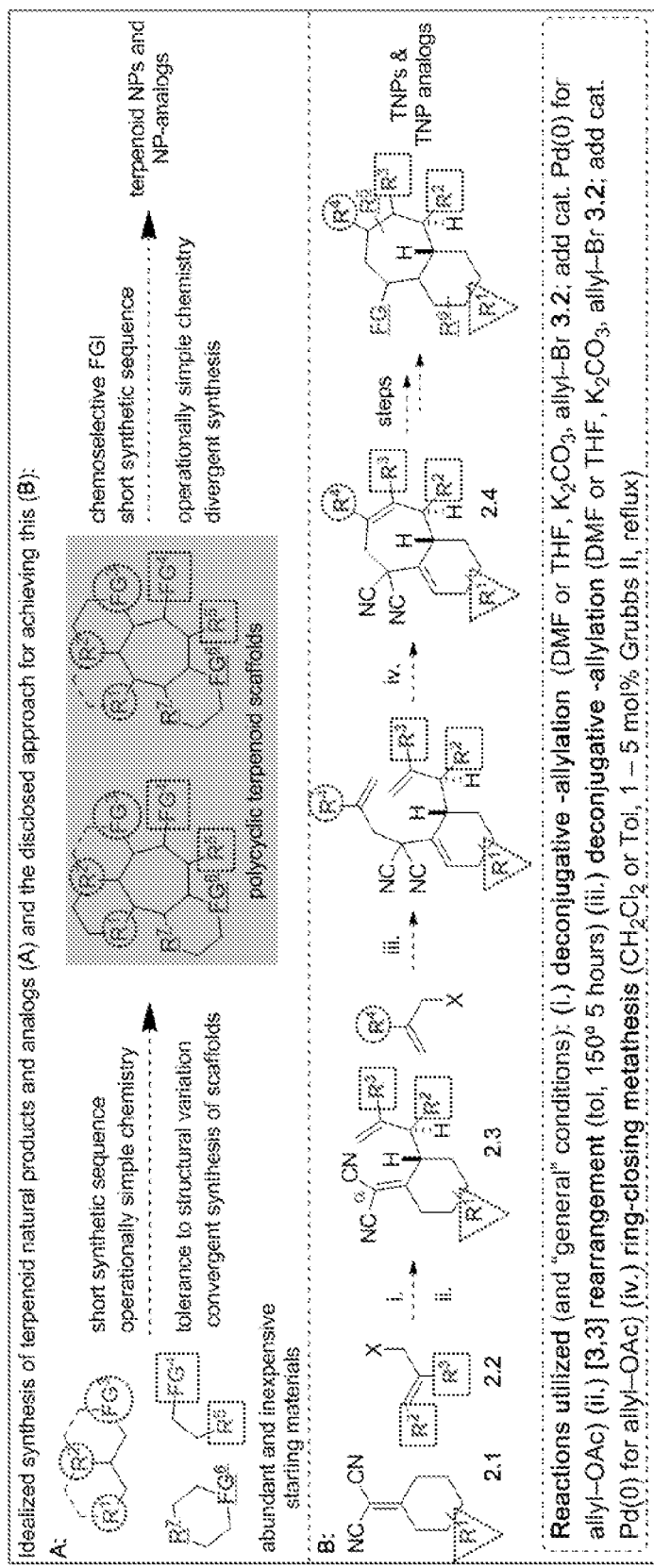
Figure 3C:
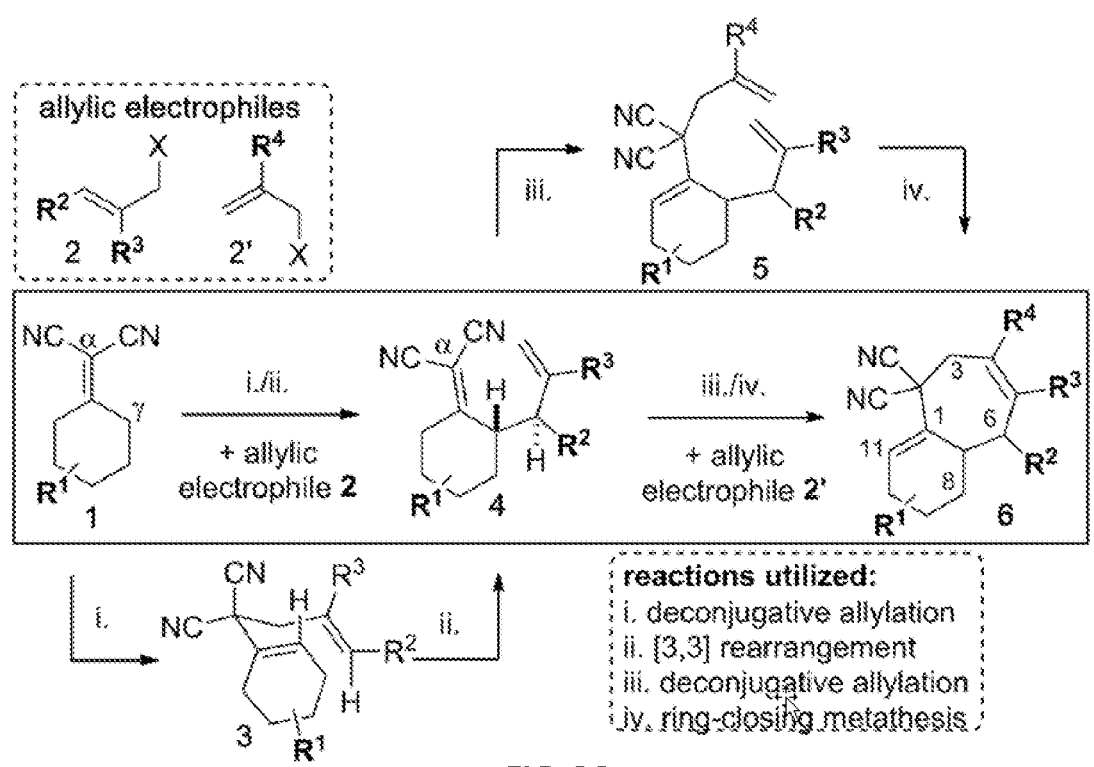

Aspects of the invention are directed to a method to form intermediate structure, according to other aspects of the invention that are γ-allyl Knoevenagel adducts of small 5-, 6-, or 7-membered ring compounds or ketone derived γ-allyl acyclic Knoevenagel adducts. In aspects of the invention, γ-allyl Knoevenagel adducts are converted into non-conjugated diene polycycloalkene precursors by γ-deprotonation/α-alkylation reactions using allylic electrophiles, as indicated in FIG. 3. Subsequently, the non-conjugated diene polycycloalkene precursors, α,γ-diallyl Knoevenagel adducts, are converted into polycycloalkenes via an intramolecular ring-closing olefin metathesis reaction, as exemplary shown in FIG. 3. As shown in FIG. 3, a γ-allyl Knoevenagel adduct 1 undergoes γ-deprotonation followed by α-alkylation with the allylic electrophiles 2 to form the non-conjugated diene polycycloalkene precursor 3. Precursor 3 undergoes a catalyzed metathesis reaction to a terpenoid scaffold 4. Knoevenagel adducts have a low $pK_a$ (~11 in DMSO) allowing mild deprotonation with bases such as $K_2CO_3$ or by the in situ generation of bases using allylic carbonates activated by Pd(0). The γ-allyl Knoevenagel adducts 1 can be prepared from most common cyclic ketones, linear ketones, malononitrile, and allylic electrophiles. Quasi γ-allyl Knoevenagel adducts can be employed where a cyano group is replaced with a carboxyester functionality to promote asymmetric reactions and allow purification of diastereomerically different intermediates. Quasi γ-allyl Knoevenagel adducts are formed from reactions with the allylated ketones rather than allylation of quasi Knoevenagel adducts.

In an aspect, disclosed are methods of synthesizing a terpenoid framework, comprising: providing a γ-allyl Knoevenagel adduct or a quasi γ-allyl Knoevenagel adduct of the structure:

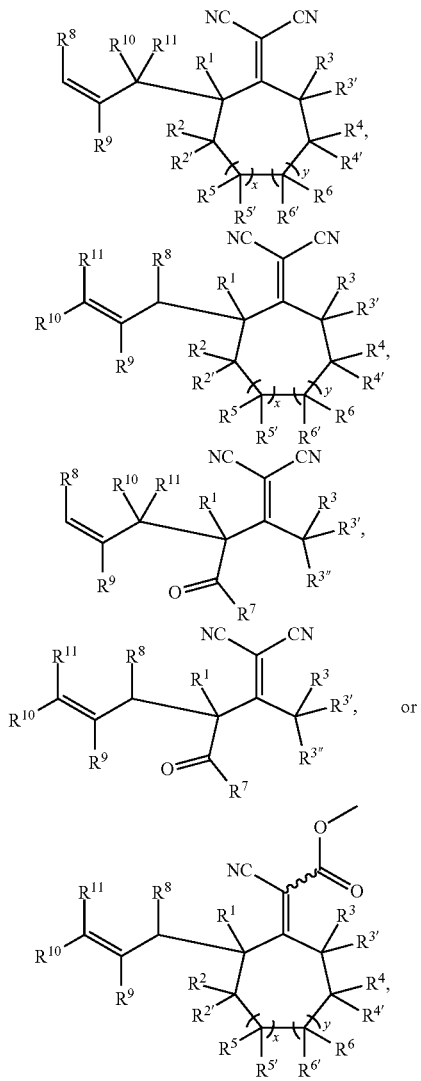

wherein x and y are independently 0 or 1; wherein $R_7$ is $C_1$ to $C_6$ alkyl or $C_1$ to $C_6$ alkoxy; wherein $R^1$, $R^2$, $R^{2'}$, $R^3$, $R^{3'}$, $R^{3''}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_e$ to $C_{12}$ alkatrieneyl, $C_3$ to $C_8$ cycloalkanyl, $C_3$ to C cycloalkenyl, $C_1$ to $C_{12}$ alkoxy, phenoxy, acetoxy, or phenyl; wherein one or more of $R^2$ with $R^{2'}$, $R^3$ with $R^{3'}$, $R^4$ with $R^{4'}$, $R^5$ with $R^{5'}$, and $R^a$ with $R^{6'}$ is optionally combined as carbonyl, ethylenyl, $C_3$ to $C_8$ cycloalkyl, $C_3$ to $C_8$ cycloalkenyl, $C_5$ to $C_6$ heterocycle containing one or more oxygens; wherein one or more of $R^{2'}$ with $R^{5'}$, $R^3$ with $R^{4'}$, $R^{4'}$ with $R^{6'}$, and $R^{5'}$ with $R^{6'}$ is optionally combined as a n-bond or a π-bond with $R^2$ with $R^5$, $R^3$ with $R^4$, $R^4$ with $R^6$, and/or $R^5$ with $R^6$ combined as an aromatic ring, $C_5$ or $C_6$ cycloalkene, or $C_5$ or $C_6$ cycloalkadiene, and where each of $R^2$, $R^3$, $R^4$, $R^5$, and $R^6$ is combined only once; wherein one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or wherein $R^4R^{4'}C$, $R^5R^{5'}C$ or $R^6R^{6'}C$ can be replaced with an oxygen; and wherein any of the alkyls, alkylenyl, alkadienyl, alkatrienyl, cycloalkyl, cycloalkenyl, alkoxy, phenoxy, aryl, and alkylene chain is optionally substituted with one or more $C_1$ to $C_4$ alkyl, $C_1$ to $C_4$ alkoxy, $C_3$ to $C_6$ cycloalkyl, $C_3$ to $C_6$ cycloalkenyl, phenyl, acetyl, or nitro groups; and wherein $R^6$ is H, phenyl or the oxygen of an oxo group, $R^9$, $R^{10}$, and $R^{11}$ are independently H, $CH_2X$, $C_1$ to $C_{12}$ alkyl, or phenyl, or wherein $R^9$ and $R^{10}$ are combined as a $C_5$ or $C_6$ cycloalkene or phenyl, wherein the $C_1$ to $C_{12}$ alkyl, phenyl, or $C_5$ or $C_6$ cycloalkene can be further substituted with one or more Br, Cl, I, $C_1$ to $C_4$ alkoxy, or where two adjacent carbons are substituted by methylenedioxy.

In an aspect, disclosed are methods of synthesizing a terpenoid framework, comprising: providing a γ-allyl Knoevenagel adduct or a quasi γ-allyl Knoevenagel adduct of the structure:

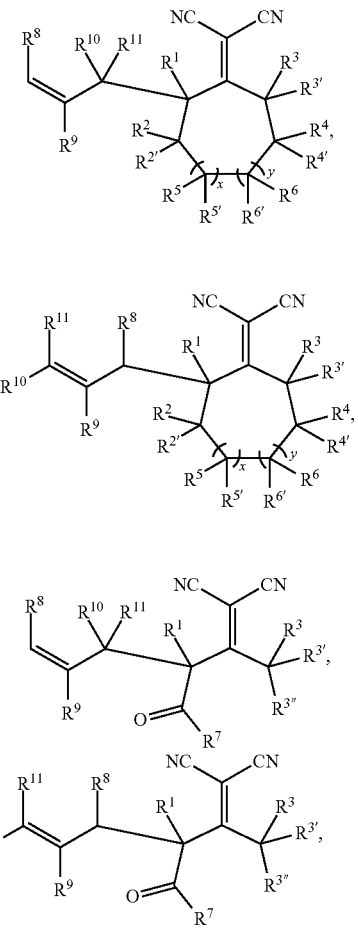

-continued

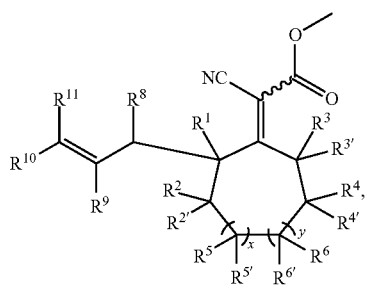

wherein x and y are independently 0 or 1; wherein $R_7$ is $C_1$ to $C_6$ alkyl or $C_1$ to $C_6$ alkoxy; wherein $R^1$, $R^2$, $R^{2'}$, $R^3$, $R^{3'}$, $R^{3'}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_6$ to $C_{12}$ alkatrienyl, $C_3$ to $C_8$ cycloalkanyl, $C_3$ to C cycloalkenyl, $C_1$ to $C_{12}$ alkoxy, phenoxy, acetoxy, or phenyl; wherein one or more of $R^2$ with $R^2$, $R^3$ with $R^{3'}$, $R^3$, $R^4$ with $R^{4'}$, $R^5$ with $R^{5'}$, and $R^6$ with $R^{6'}$ is optionally combined as carbonyl, ethylenyl, $C_3$ to $C_6$ cycloalkyl, $C_3$ to $C_8$ cycloalkenyl, $C_5$ to $C_6$ heterocycle containing one or more oxygens; wherein one or more of $R^{2'}$ with $R^{5'}$, $R^{3'}$ with $R^4$, $R^4$ with $R^{6'}$, and $R^{5'}$ with $R^6$ is optionally combined as a π-bond or a π-bond with $R^2$ with $R^5$, $R^3$ with $R^4$, $R^4$ with $R^6$, and/or $R^5$ with $R^6$ combined as an aromatic ring, $C_5$ or $C_6$ cycloalkene, or $C_5$ or $C_6$ cycloalkadiene, and where each of $R^2$, $R^3$, $R^4$, $R^5$, and $R^6$ is combined only once; wherein one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or wherein $R^4R^{4'}C$, $R^5R^{5'}C$ or $R^6R^{6'}C$ can be replaced with an oxygen; and wherein any of the alkyls, alkylenyl, alkadienyl, alkatrienyl, cycloalkyl, cycloalkenyl, alkoxy, phenoxy, aryl, and alkylene chain is optionally substituted with one or more $C_1$ to $C_4$ alkyl, $C_1$ to $C_4$ alkoxy, $C_3$ to $C_6$ cycloalkyl, $C_3$ to $C_6$ cycloalkenyl, phenyl, acetyl, or nitro groups; and wherein $R^a$ is H, phenyl or the oxygen of an oxo group, $R^9$, $R^{10}$, and $R^{11}$ are independently H, $CH_2X$, $C_1$ to $C_{12}$ alkyl, or phenyl, or wherein $R^9$ and $R^{10}$ are combined as a $C_5$ or $C_6$ cycloalkene or phenyl, wherein the $C_1$ to $C_{12}$ alkyl, phenyl, or $C_5$ or $C_6$ cycloalkene can be further substituted with one or more Br, Cl, I, $C_1$ to $C_4$ alkoxy, or where two adjacent carbons are substituted by methylenedioxy; further comprising reacting the γ-allyl Knoevenagel adduct or a quasi γ-allyl Knoevenagel adduct with an allyl comprising electrophile to form an α,γ-diallyl Knoevenagel adduct or quasi α,γ-diallyl Knoevenagel adduct; and catalyzing a ring-closure metathesis of the α,γ-diallyl Knoevenagel adduct or quasi α,γ-diallyl Knoevenagel adduct to a terpenoid framework.

In an aspect, disclosed are methods of synthesizing a terpenoid framework, comprising: providing a γ-allyl Knoevenagel adduct or a quasi γ-allyl Knoevenagel adduct of the structure:

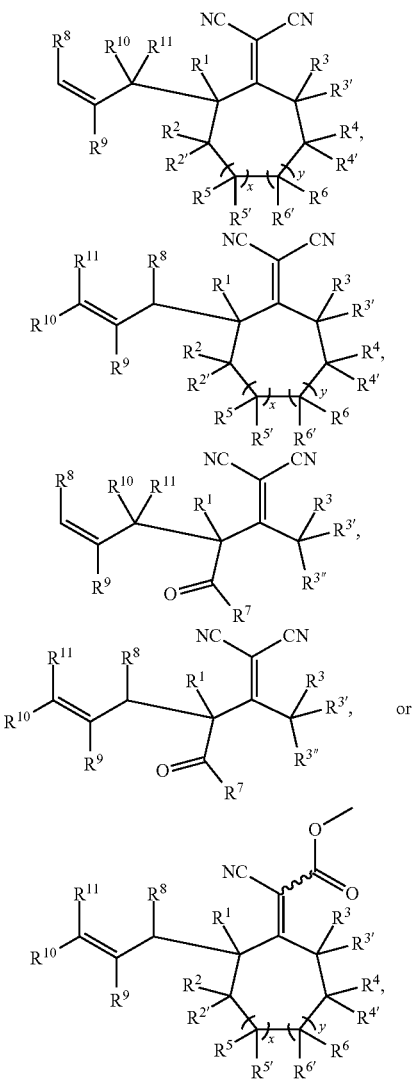

wherein x and y are independently 0 or 1; wherein $R_7$ is $C_1$ to $C_6$ alkyl or $C_1$ to $C_6$ alkoxy; wherein $R^1$, $R^2$, $R^{2'}$, $R^3$, $R^{3'}$, $R^{3'''}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_e$ to $C_{12}$ alkatrienyl, $C_3$ to $C_8$ cycloalkanyl, $C_3$ to $C_8$ cycloalkenyl, $C_1$ to $C_{12}$ alkoxy, phenoxy, acetoxy, or phenyl; wherein one or more of $R^2$ with $R^{2'}$, $R^3$ with $R^{3'}$, $R^{3'''}$, $R^4$ with $R^{4'}$, $R^5$ with $R^{5'}$, and $R^6$ with $R^{6'}$ is optionally combined as carbonyl, ethylenyl, $C_3$ to $C_8$ cycloalkyl, $C_3$ to $C_8$ cycloalkenyl, $C_5$ to $C_6$ heterocycle containing one or more oxygens; wherein one or more of $R^{2'}$ with $R^{5'}$, $R^{3'}$ with $R^4$, $R^{4'}$ with $R^{6'}$, and $R^5$ with $R^{6'}$ is optionally combined as a π-bond or a π-bond with $R^2$ with $R^5$, $R^3$ with $R^4$, $R^4$ with $R^6$, and/or $R^5$ with $R^6$ combined as an aromatic ring, $C_5$ or C cycloalkene, or $C_5$ or $C_6$ cycloalkadiene, and where each of $R^2$, $R^3$, $R^4$, $R^5$, and $R^6$ is combined only once; wherein one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or wherein $R^4R^{4'}C$, $R^5R^{5'}C$ or $R^6R^{6'}C$ can be replaced with an oxygen; and wherein any of the alkyls, alkylenyl, alkadienyl, alkatrienyl, cycloalkyl, cycloalkenyl, alkoxy, phenoxy, aryl, and alkylene chain is optionally substituted with one or more $C_1$ to $C_4$ alkyl, $C_1$ to $C_4$ alkoxy, $C_3$ to C cycloalkyl, $C_3$ to $C_6$ cycloalkenyl, phenyl, acetyl, or nitro groups; and wherein $R^8$ is H, phenyl or the oxygen of an oxo group, $R^9$, $R^{10}$, and $R^{11}$ are independently H, $CH_2X$, $C_1$ to $C_{12}$ alkyl, or phenyl, or wherein $R^9$ and $R^{10}$ are combined as a $C_5$ or $C_6$ cycloalkene or phenyl, wherein the $C_1$ to $C_{12}$ alkyl, phenyl, or $C_5$ or $C_6$ cycloalkene can be further substituted with one or more Br, Cl, I, $C_1$ to $C_4$ alkoxy, or where two adjacent carbons are substituted by methylenedioxy; wherein providing a γ-allyl Knoevenagel adduct or the quasi γ-allyl Knoevenagel adduct comprises reacting a ketone comprising molecule of the structure:

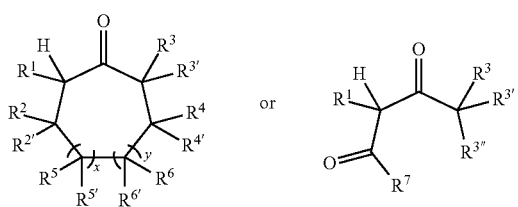

with an allyl electrophile of the structure:

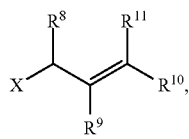

wherein X is a leaving group selected from acetoxy, t-butyloxycarbonoxy, Cl, Br, I, trifluroacetoxy, or tosyl.

D. Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Synthetic Examples. The γ-allyl Knoevenagel adducts 1a-1k, form via an intermediate 3,3-dicyano-1,5-diene 6a-6k that undergo a thermal [3,3] sigmatropic rearrangement. Exemplary Knoevenagel adducts from reaction of the 5a-5g and the allylic acetates/carbonates 2a-2g, shown in FIG. 5, were prepared in one step from commercial material and converted to the dicyano-1,5-dienes 6a-6k via Pd-catalysis in 58-95% yield, where the starting Knoevenagel adducts and allylic electrophiles. Heating 1,5-dienes 6 at 140-170° C. promotes Cope rearrangement to the desired γ-allyl Knoevenagel adducts 1a to 1k in 50-95% yield. Conversion from 6 to 1a-1k via Cope rearrangement is compatible with a variety of structural variation and is diastereoselective (>20:1 dr) when terminally substituted allylic electrophiles are used (2f and 2g). Surprisingly, Knoevenagel condensation of α-quaternary-1,3-diketones, from 7a-7g, is not sterically inhibited nor is there a significant occurrence of over-condensation due to the two ketone moieties. All exemplary syntheses yield the desired products 11-1s, as shown in FIG. 6.

Figure 6:
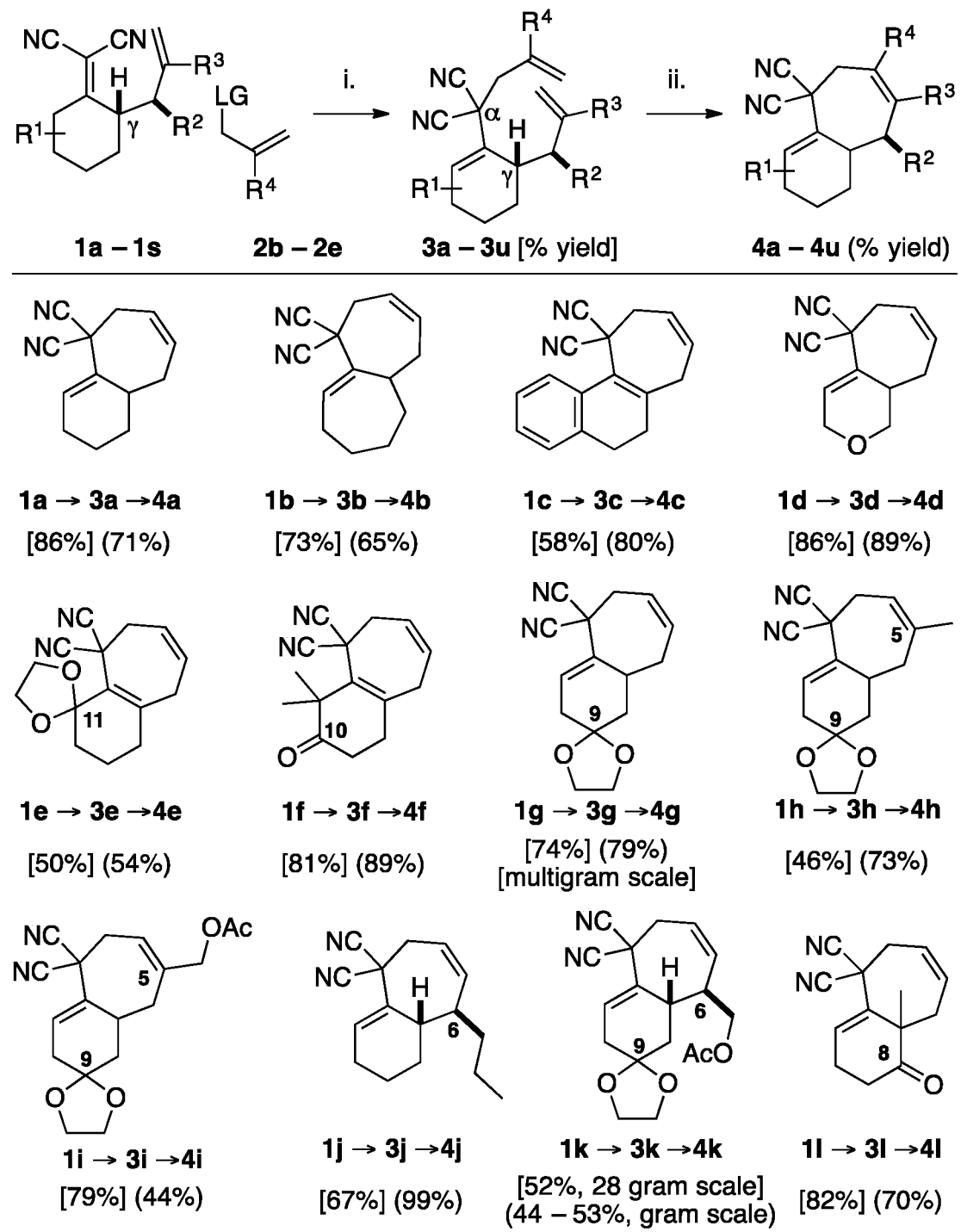
FIG. 6 shows exemplary 5/7 and 6/7 terpene-like bicyloalkanes, which are accessible by allylation followed by ring-closure metathesis (RCM), according to aspects of the invention.

The γ-allyl Knoevenagel adducts 1a-1s were converted to 5/7 and 6/7 bicycloalkanes by Pd-catalyzed α-allylation to 3a-3u followed by ring-closing metathesis to 4a-4u, as shown in FIG. 6, top. Notably, the second α-allylation occurs using 1 mol % Pd(PPh$_3$)$_4$ with various allylic carbonates 2 and is initiated by deprotonation at the least sterically hindered γ-position of the γ-allyl-Knoevenagel adduct 1. Grubbs' second-generation catalyst enables the ring-closing metathesis at a catalyst loading at 1 mol % or less in most cases, although loadings as high as 5 mol % was required for some adducts.

The reaction temperatures between 80 and 100° C. the reaction proceeds smoothly, At temperatures that are greater than 100° C., Cope rearrangement competed with the metathesis forming structures 3 that include 3,3-dicyano-1, 5-dienes. Under the optimized conditions, Cope rearrangement does not occur and the metathesis reaction provides good to excellent yields, 44-99% yields, for the desired bicycloalkanes.

Telescoping the allylation and rearrangement allows step-economy, improves efficiency, and avoids chromatography, as indicated in FIG. 7. For example, Knoevenagel adduct 5g could be converted to the γ-allylated building block 3g without purification on a large scale, more than 20 grams, in 75% overall yield using the standard protocol indicated above. From 6k, the Cope rearrangement and second allylation could be telescoped to yield 3k in 52% yield on a large scale, where 16 grams of 3k is easily isolated.

The terpenoids prepared from γ-allyl Knoevenagel adducts are structurally diverse, as illustrated in FIG. 6. Differentiating base or pre-terpene ring structures, for example, 4a-4g and 4l-4r, begins with the judicious choice of a ketone that encompasses different ring sizes, substitution, and heteroatom content, for example, 4a from cyclohexane, 4b from cycloheptane, 4o from cyclopentane, a tricyclic scaffold from 4c, a heterocycle from 4d, and the inclusion of ketones and protected ketones at many positions, such as C-8, C-9, C-10, and/or C-11, as indicated in FIG. 3 about the cyclohexane ring and two equivalents of allyl electrophiles, for example, allyl acetate or carbonate 2a or 2b. Polycyclics possessing an ester group 7-transangular position, for example, 4p and 4q, can be formed using commercially available Dieckmann adducts, for example, 7e and 7f. The substitution pattern about the cycloheptene or other ring formed upon metathesis ring formation depends upon the allylic alcohol-based electrophiles 2. The substitution at C-4 and C-5, as shown in FIG. 3, is achieved by the order of allylation. For example, methyl groups, as in 4h, 4s, and 4u, and protected carbinols, as in 4i and 4t can be substituents at these positions, which result from the substitution of the allylic alcohols used, for example 2c-2e. Substitution at the 6-position, as indicated in FIG. 3 about the bicyclic frameworks is easily achieved via Cope rearrangement of terminally substituted allylic reagents, such as 2f and 2g. In this manner, one may incorporate a propyl group, as in 4j from 2f as well as an acetoxymethylene, as in 4k from 2g at the 6-position. By varying the ketone and the allylic-based reagents, structurally diverse terpenoid-like molecules with specific oxidation patterns can be prepared. This oxidation pattern affects the terpenoid's biological activity. From a single γ-allyl Knoevenagel adduct, such as 11, diversity can be achieved by varying the allylic electrophile at the late stage 4l, 4s, and 4t. This allows for increased efficiency in diversification.

Figure 8:
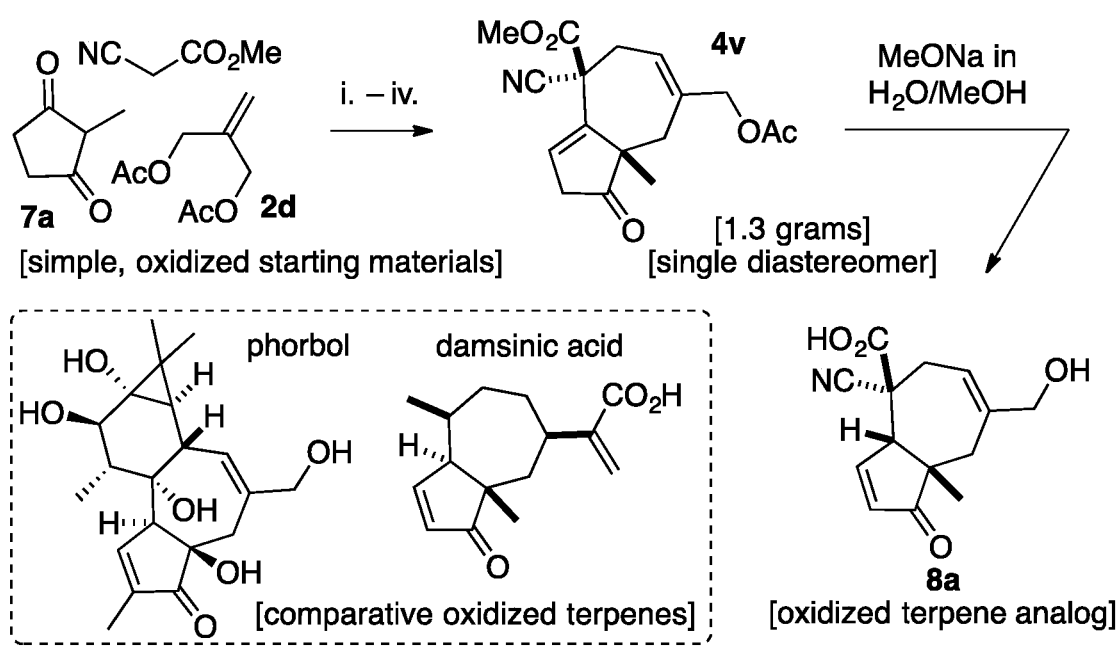
FIG. 8 shows a reaction scheme for Synthesis of cyclopentenone-containing terpenoid congeners, according to an aspect of the invention.

In aspects of the invention, oxidized starting materials are rapidly relayed into complex, oxidized bicyclic cores. As illustrated in FIG. 8, commercially available 2-methyl-1,3-cyclopentandione 7a, methylenepropanediol diacetate 4d, formed in a high yield 1-step synthesis, and commercially available methyl cyanoacetate can form the bicycloalkane terpenoid building block 4v through a four-step synthesis. The second allylation-step, step iii. of FIG. 8, is diastereoselective (10:1 dr) to give 1t that can be isolated as a single diastereomer. Congener 8a of bioactive cyclopentenone natural products tigliane (phorbol) and pseudoguaiane (damsinic acid) can be generated by a base-promoted enoneisomerization, saponification, and deacylation in excellent yield.

Figure 9:
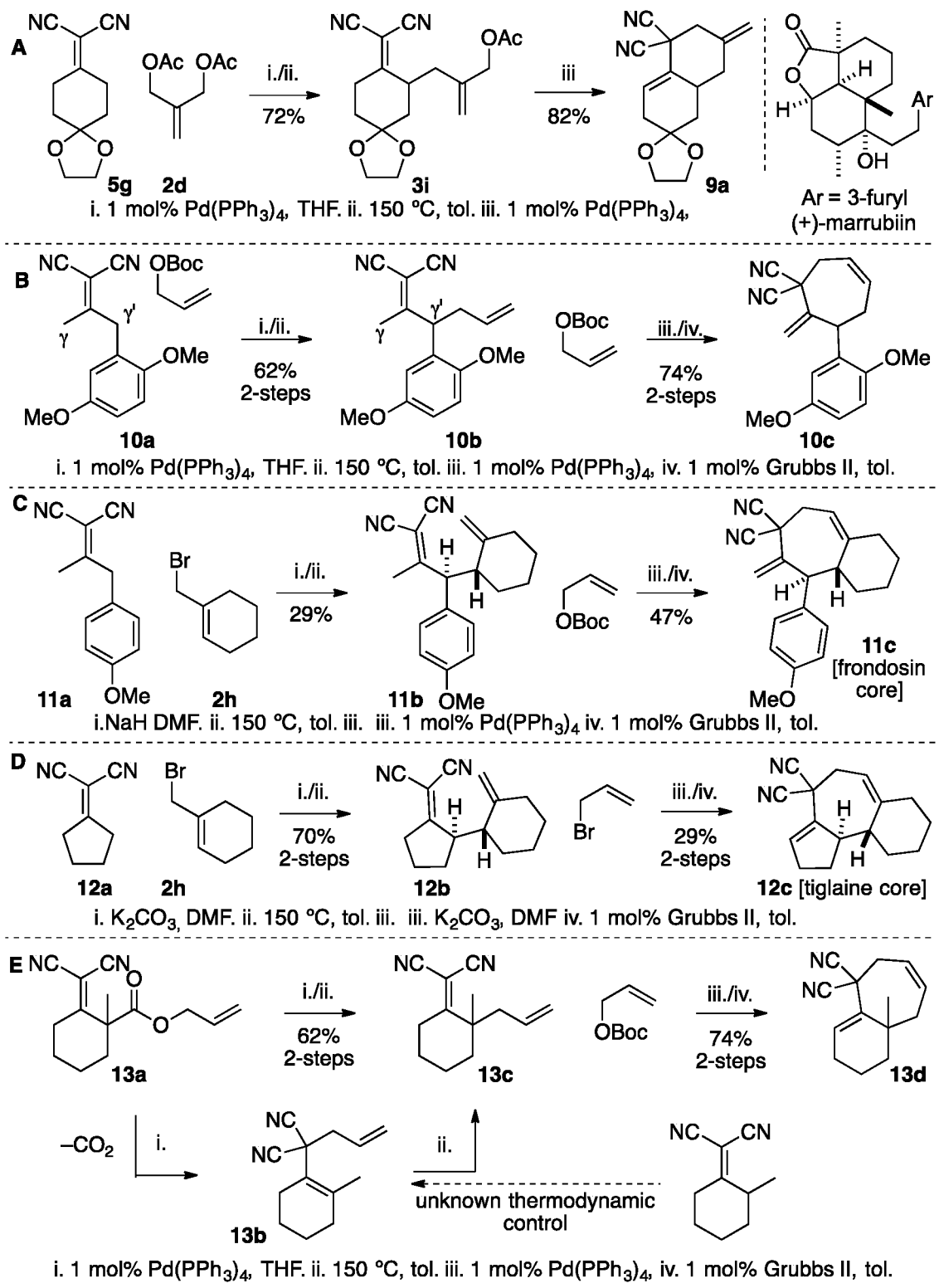
FIG. 9 shows reaction schemes for a variety of transformations to terpenoid congeners involving a [3,3]-rearrangement-centered sequence, according to an aspect of the invention.

The γ-allyl Knoevenagel adducts, according to aspects of the invention, can be used in methods that are varied to make terpenoid scaffolds as illustrated in FIG. 9, according to an aspect of the invention. Variations of the [3,3]-centered synthetic method permits generation of γ-allyl Knoevenagel adducts, as shown in FIG. 9. Allylic electrophiles, such as 2d and 2e, are conjunctive reagents, where α-allylation/[3,3] rearrangement with 5g, intramolecular allylic alkylation yields a decalin core as in reaction A of FIG. 9. Bioactive decalin natural products, such as marrubin, are synthetically viable targets beginning from ketones, malonic acid derivatives, and bis-allylic reagents using the γ-allyl Knoevenagel adducts routes according to an aspect of the invention.

Acyclic Knoevenagel adducts derived from α-arylacetone, as illustrated in reaction B of FIG. 9 for 10a, form γ-allyl Knoevenagel adduct 10b, by allylation/[3,3] rearrangement. This adduct can be transformed into an arylcycloheptene core 10c by an allylation/RCM sequence. This represents a truncated core of frondosin natural products as shown in FIG. 1. The second allylation occurs by deprotonation at the γ-position rather than at the potentially more acidic γ'-position. Any alkylation at a γ'-deprotonation would lead to a mixture of alkene isomers, one of which would not be able to undergo ring-closing metathesis due to geometric restrictions.

By use of cyclic-allylic electrophiles, such as 2h, as indicated in FIG. 9 reaction C, carbon-frameworks bearing an additional ring result. Reaction of the Knoevenagel adduct 11a with cyclic-allylic electrophile 2h yields 11b by the allylation/[3,3] rearrangement in reasonable yield with excellent diastereocontrol (>20:1 dr). Allylation/ring-closing metathesis reaction forms the 6/7 framework 11c, which closely resembles frondosin/liphagal natural products, as shown in FIG. 1. The [3,3] sigmatropic rearrangement step converts internal, trisubstituted alkene of 2h into the disubstituted exomethylene on 11b, which is consistent with the product driving-force being the alkylidenemalononitrile-conjugation for the [3,3] sigmatropic rearrangement rather than formation of the more substituted olefin.

Cyclic Knoevenagel adducts, such as 12a, result in tricyclic carbon frameworks, as shown in FIG. 9 reaction D, where Knoevenagel adduct 12a reacts with cyclic-allylic electrophile 2h such that the allylation/[3,3] sigmatropic rearrangement sequence yields 1,1'-bicycloalkane 12b bearing an exomethylene functional group. Subsequent allylation/RCM forms an angular 5/7/6 ring system 12c. The second allylation step results in a mixture of products derived from competing α-allylation and γ-allylation. The α-allylation provides synthetic tigliane and daphnane frameworks, which are natural products, along with their congeners, are desirable because of their biological activities.

As shown in FIG. 6, deprotonation of γ-allyl Knoevenagel adduct 1 is effective at the less substituted γ-position. By starting with a γ-allyl ester substituted Knoevenagel adduct, such as 13a, a decarboxylative allylation reaction results in a 1,5-diene, such as 13b. The decarboxylative allylation method allows generation of the lower energy Knoeveangel adduct anion by decarboxylation rather than the product indicative of the deprotonation selectivity absent the ester, as shown in FIG. 6. The strong conjugation-driving force directs the Cope rearrangement towards the generation of a quaternary center, as in 13c. Subsequent allylation/RCM forms a 6/7 bicycloalkane, such as 13d, which bears a transangular methyl group at the quaternary carbon.

Figure 10:
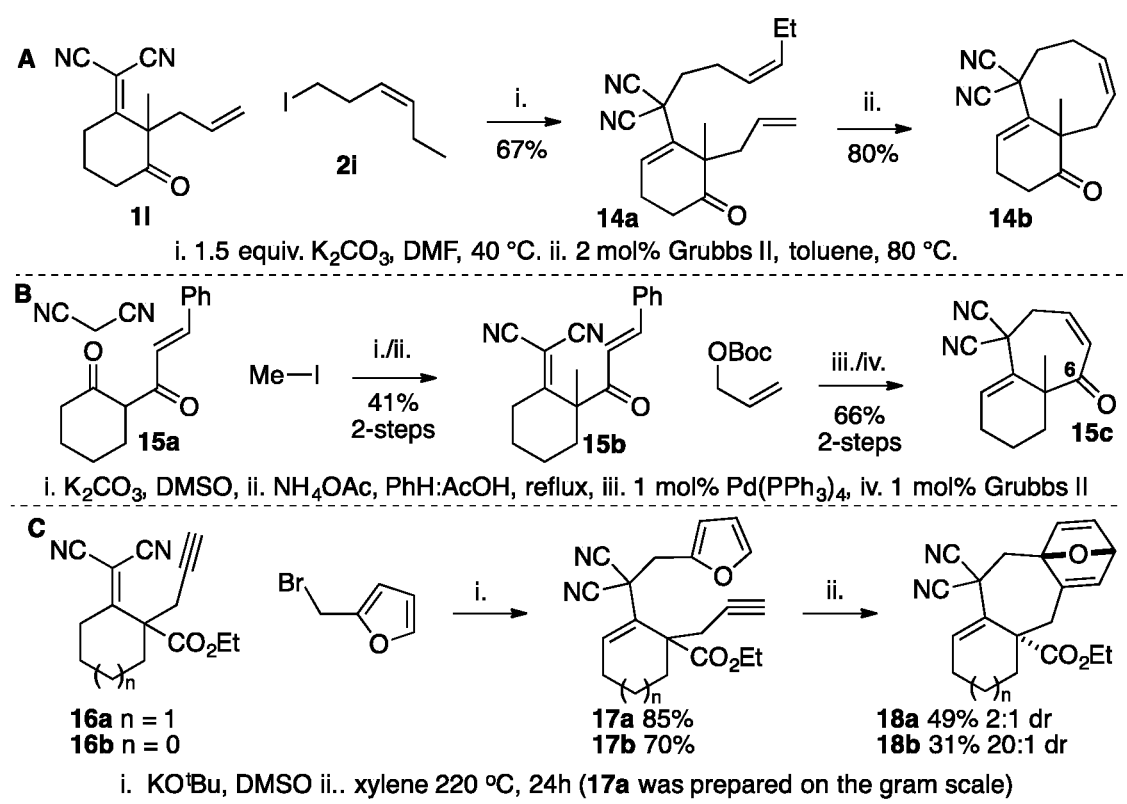
FIG. 10 shows reaction schemes for a variety of transformations to terpenoid congeners that result from 1,3-dicarbonyl compounds for the preparation of the γ-allyl Knoevenagel adducts, according to an aspect of the invention.

Starting from 1,3-dicarbonyl building blocks, exemplary shown in FIG. 10 reaction A, homoallylic iodide 2i alkylation of the Knoevenagel adduct 11 forms diene 14a that forms the cyclooctanoid structure 14b α-alkylation/RCM. Many terpenoid natural products with promising biological activities share this cyclooctanoid structure. Homoallylic iodide 2i can be formed from the corresponding hexenyl alcohol.

As shown in FIG. 10 reaction B, using β-diketone 15a that is prepared by Claisen condensation of cyclohexanone and cinnamoyl chloride, by ketone methylation followed by Knoevenagel condensation cyclic ketone 15b is selectively formed rather than an α,β-unsaturated ketone. Subsequent α-Allylation/RCM of 15b results in a 6-oxo-bicyclo[4.3.0]undecane architecture 15c, which displays a C-6 oxygenation that is common to many natural products, including ingenol, scabronine G, sandresolide B, englerin A, and dihydrohelenalin, as illustrated in FIG. 1.

By selection of functional groups substituted at α- and γ-positions of Knoevenagel adducts, various cycloheptane comprising polycyclics can be formed. For example, as shown in FIG. 10 reaction C, a propargyl group, for example, 16a or 16b and a furan, for example, 17a or 17b allows intramolecular Diels-Alder furan (IMDAF) cycloaddition to yield tricyclic terpenoid building blocks, such as 18a and 18b. These tricyclics are structurally similar to many classes of diterpenoid natural products, such as some illustrated in FIG. 1.

Figure 11:
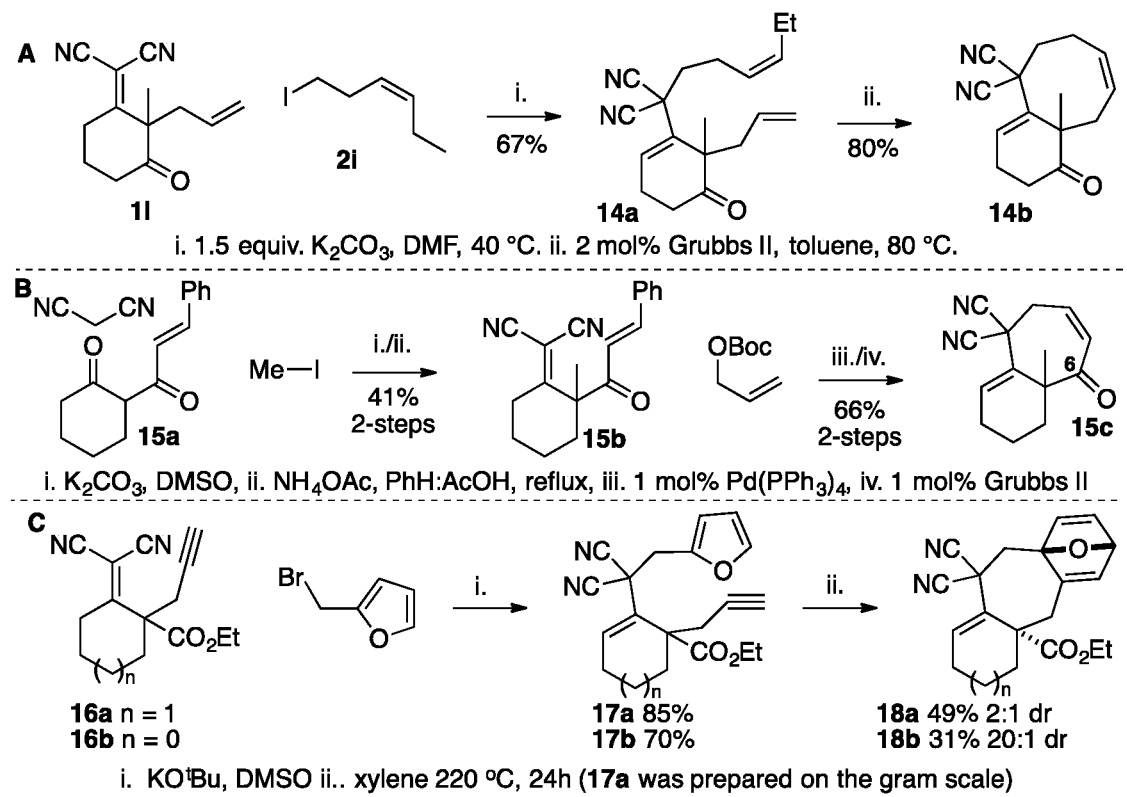
FIG. 11 shows reaction schemes for exemplary transformations of functionality in terpenoid congeners formed via γ-allyl Knoevenagel adducts, according to an aspect of the invention.

The synthetic methods, according to aspects of the invention described above, readily permit formation of a variety of different functionally dense cycloheptenes using widely available reagents to synthesize these complex molecules. Various, "late-stage" chemical transformation of "early stage" terpenoid-like intermediates allows many diverse structures to be formed, as shown in FIG. 11. For example, using ketal-containing substrate 4g with Upjohn conditions ($OsO_4$/NMO), lactone 19a was isolated as a single diastereomer by diastereoselective dihydroxylation followed by intramolecular Pinner reaction and subsequent imidate hydrolysis. Numerous bicyclic [4.2.1] terpenoid-lactones are structurally related, such as hushinone, versicolactone C, aristoyunnolin A, and 2a,11-Dihydroxy-1(10)-tremulen-5,12-olide. Additionally, epoxidation of a ketal-containing substrate, such as 4g, allows diastereoselectively epoxidation, for example, 19b using a standard procedure, which displays a high diastereoselectivity (>20:1 dr), which for 19b in FIG. 11 is assumed based on related syn-dihydroxylation result and modeling studies. Compounds that bear an allylic acetate moiety permit Tsuji-Trost allylation, for example, the conversion of 4i to 19c using para-methoxyphenol as a nucleophile. Enones, such as 4k, are readily deprotected to form α,β-unsaturated ketone, such as 19d, by the use of 12 as a catalyst.

It was discovered that cycloheptyl-alkenes, such as 4o, readily undergo chemoselective transformations, as shown in FIG. 11. For example, hydrogenated of 4o forms 19e chemoselectively with hydrogenation of the C1/C10 alkene is apparently blocked. As occurs with a related substrate, 4v, in FIG. 8, trisubstituted alkenes, such as 4o, are diastereoselectively isomerized to form cyclopentenones, such as 19f under acidic conditions, for example, with $H_2SO_4$, or under basic conditions, for example, using Hunig's base. This scaffold resembles anticancer pseudoguaianolide natural products, such as helenalin, which is shown in FIG. 1. Ketone functionalities are diastereoselectively reduced with $NaBH_4$, for example, the transformation of 4o to 19g. Decyanation under basic conditions by a hydrodecyanation-E2 reaction at C-3 transforms trisubstituted alkenes, such as 4o, to conjugated triene, such as 19h in good yield. Another notable transformation of these trisubstituted alkenes, such as 4o, is the radical decyanation using lithium naphthalenide (LN) that shows reduction selectivity in the presence of other reducible functional groups, as shown for the transformation of 4o to 19i, though with a 1:1 mixture of nitrile isomers.

Figure 12:
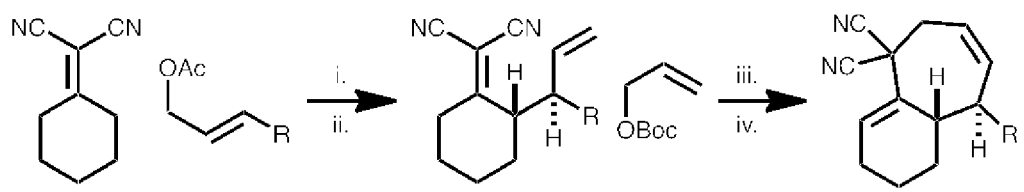
FIG. 12 shows a generalized reaction scheme for structural variation of the terpene-like ring due to the structures of the ketone precursors and the structural variation of the allyl electrophile, according to an aspect of the invention.
Figure 13:
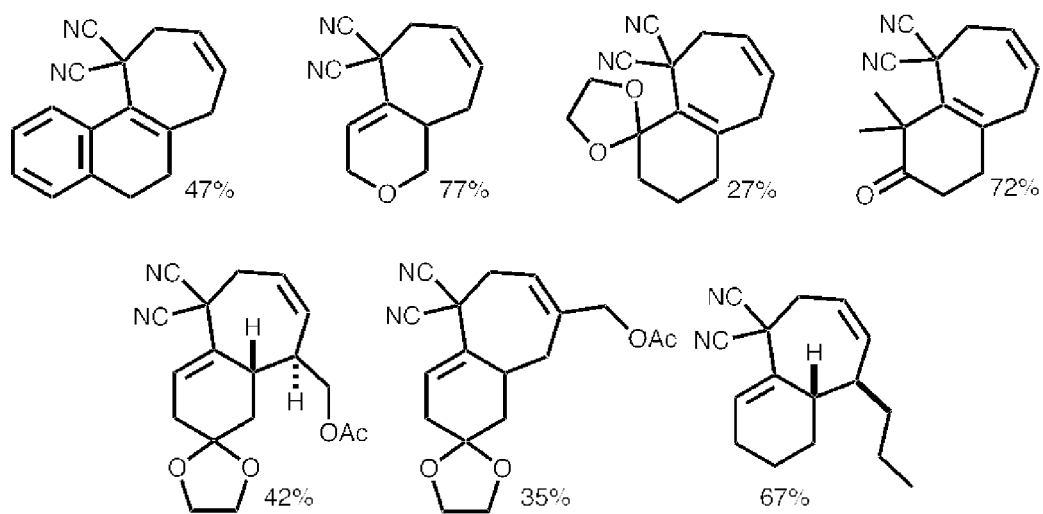
FIG. 13 shows the structure of various terpene-like ring structures formed as per the scheme of FIG. 12 and the overall yields for the transformation, according to an aspect of the invention.
Figure 14:
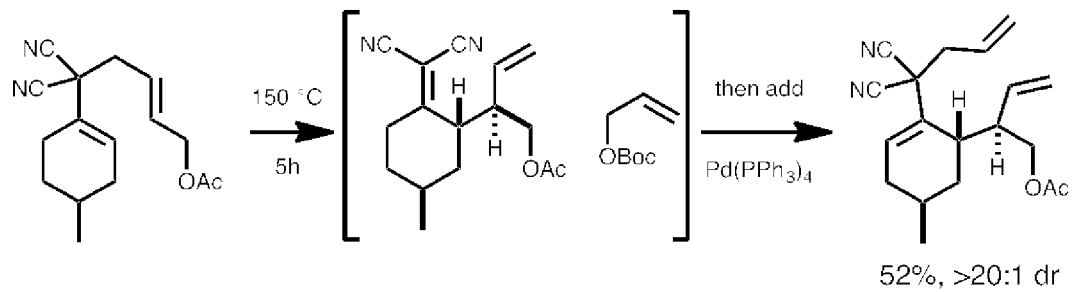
FIG. 14 shows a reaction scheme for an effective one-pot allyl-allyl-allyl coupling via a [3,3] rearrangement, according to an aspect of the invention.

The use of different allyl electrophile additions to form to form the γ-allyl Knoevenagel adduct is illustrated in FIG. 12 and this reaction followed by α-allylation and RCM form a large variety of terpene-like rings with examples shown in FIG. 13 shows the structure of various terpene-like ring structures. An effective one-pot allyl-allyl-allyl coupling via a [3,3] rearrangement, as shown in FIG. 14.

Figure 15:
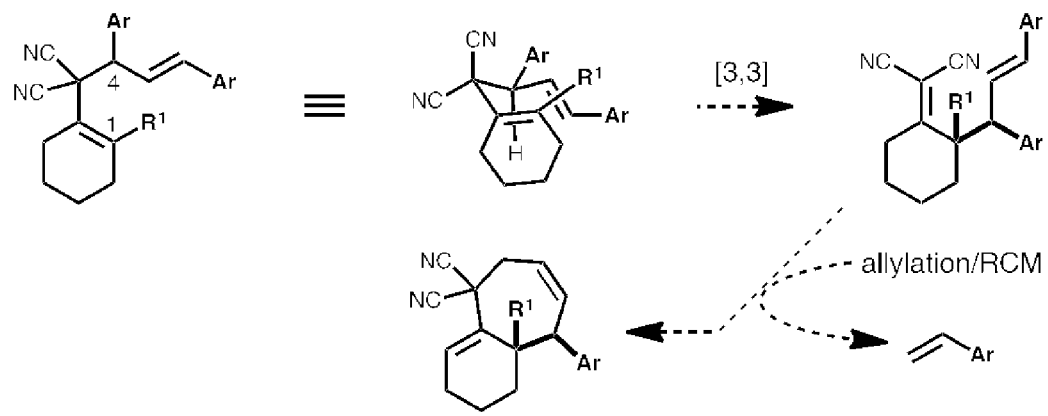
FIG. 15 shows a reaction scheme where alkylidene and styrene conjugation acts as a driving force for [3,3] rearrangement, according to an aspect of the invention.
Figure 16:
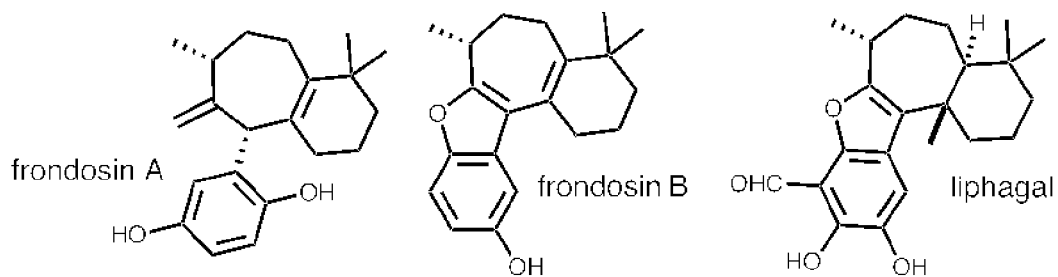
FIG. 16 shows the structure of various terpene-like ring structures accessible by the reaction scheme of FIG. 15, according to an aspect of the invention.
Figure 17:
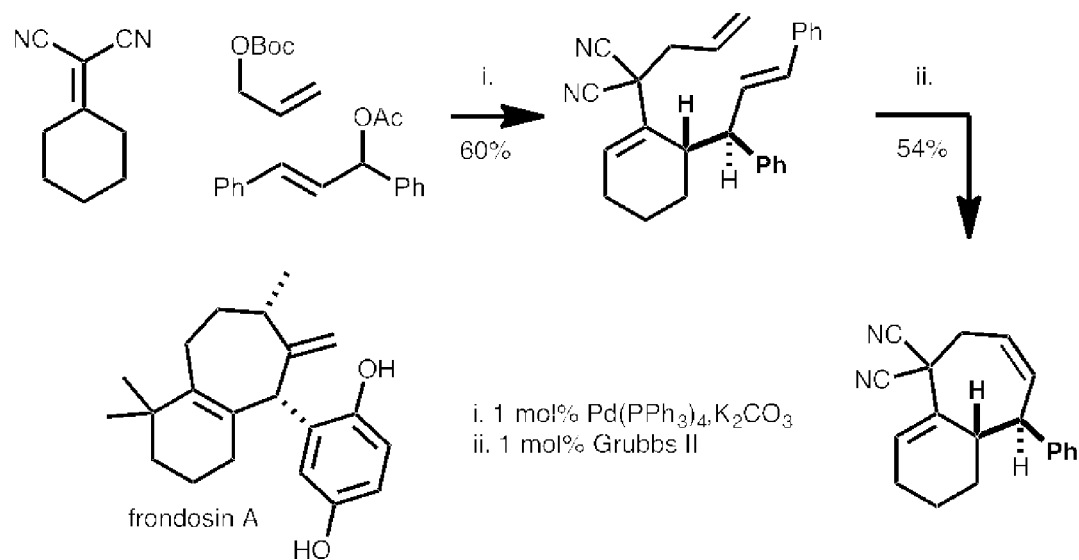
FIG. 17 shows a reaction scheme where direct γ-allylation is carried out to form the γ-allyl Knoevenagel adduct, according to an aspect of the invention.
Figure 18:
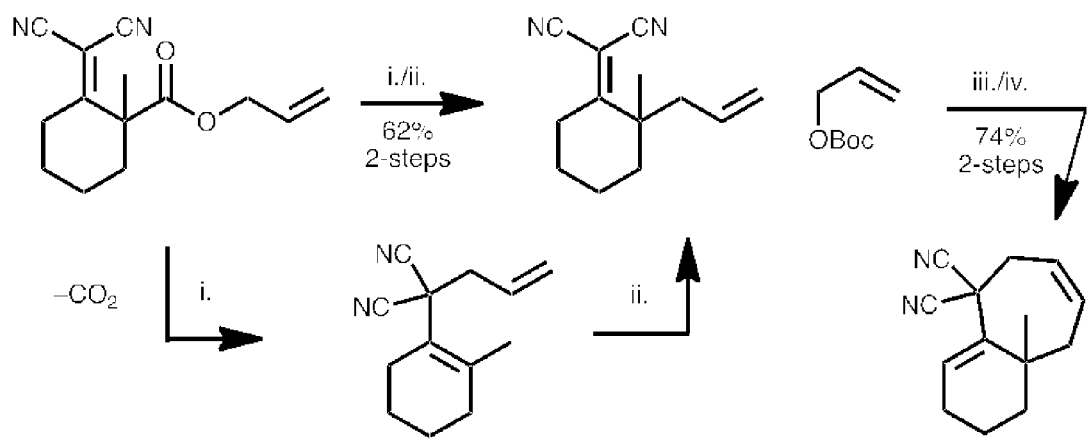
FIG. 18 shows a reaction scheme where a decarbonylation allylation is employed to yield a γ-allyl Knoevenagel adduct where the terpene-like bicycloalkane has a transangular methyl group, according to an aspect of the invention.

As shown in FIG. 15, alkylidene and styrene conjugation can provide a driving force for [3,3] rearrangement to the γ-allyl Knoevenagel adduct, which upon subsequent allylation and RCM can yield a carbon framework common to many terpenes, as illustrated in FIG. 16. In an aspect of the invention, as shown in FIG. 17, a direct γ-allylation without rearrangement can be carried out to form the γ-allyl Knoevenagel adduct of similar structure to that formed by the route with rearrangement shown in FIG. 15. In another aspect of the invention, the decarbonylation allylation from a γ-ester is employed to yield a γ-allyl Knoevenagel adduct that can form terpene-like bicycloalkane with a transangular methyl group, as shown in FIG. 18. In an aspect of the invention, as shown in FIG. 19, malononitrile-conjugation acts as a driving force for [3,3] rearrangement, which can alternately be employed to yield carbon framework common to many terpenes, as illustrated in FIG. 16.

Figure 23:
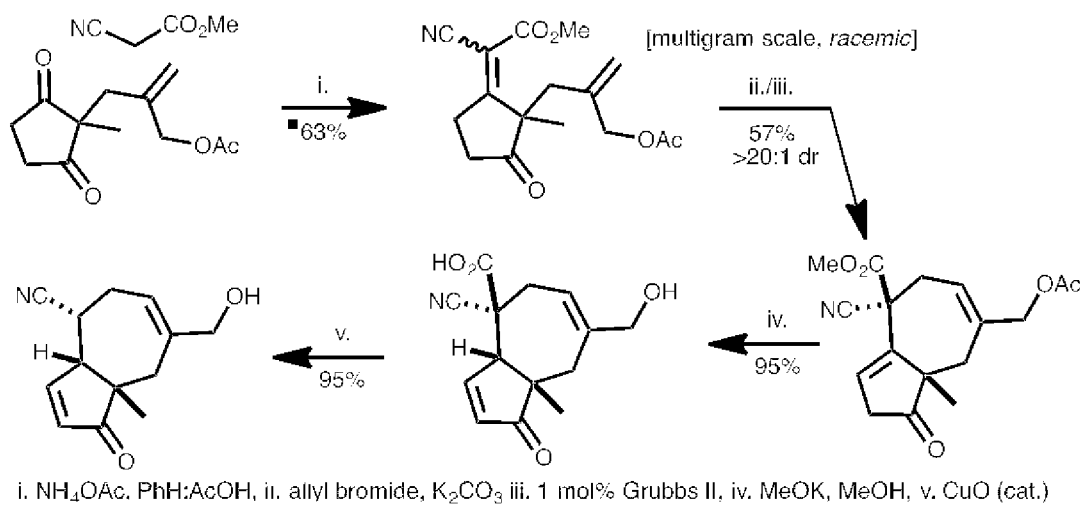
FIG. 23 shows a reaction scheme where a quasi γ-allyl Knoevenagel adduct is used to carry out a desymmetrization reaction, according to an aspect of the invention.
Figure 24:
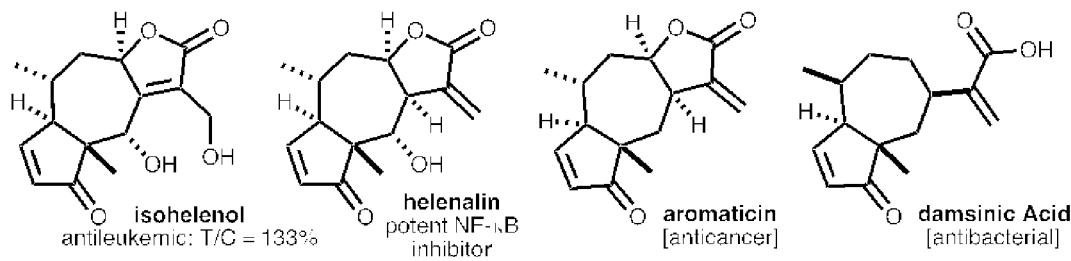
FIG. 24 shows the structure of various terpene-like ring structures accessible by the reaction scheme of FIG. 23, according to an aspect of the invention.

Using Cyclic-allylic electrophiles in the formation of the a γ-allyl Knoevenagel adducts, as shown in FIG. 20, that can form tricycle alkanes common to many target terpenes, according to an aspect of the invention. In another aspect of the invention, 1,5-enyne [3,3] rearrangements followed by α-allylation, cyclization and carbonylation yields a 6/7/5 diterpenoid structure, which is a carbon frame of many terpene ring structures, as shown in FIGS. 21 and 22. In an aspect of the invention, as shown in FIG. 23, quasi γ-allyl Knoevenagel adducts where an asymmetric nucleophile can be formed upon deprotonation to carry out desymmetrization reactions. These desymmetrization reactions can yield bicycle-frameworks that are common to many terpenes, for example, those shown in FIG. 24.

Figure 25:
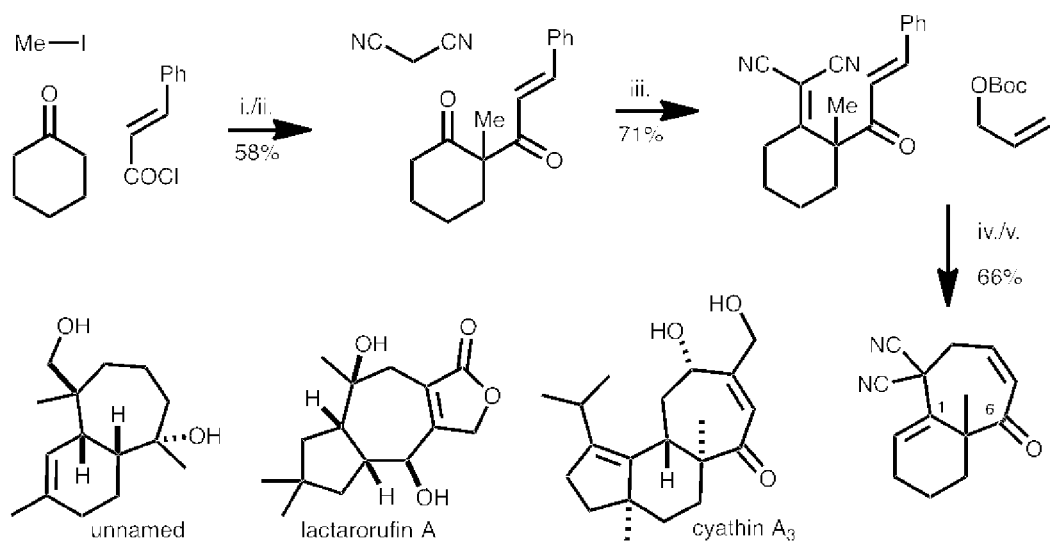
FIG. 25 shows a reaction scheme where an exocyclic 1,3-dione is converted into the γ-allyl Knoevenagel adduct and subsequently into an oxo containing 7 membered ring of the terpene-like ring structure, according to an aspect of the invention.

The γ-allyl Knoevenagel adduct used in the methods according to aspects of the invention, can be accessed by the conversion of an exocyclic 1,3-dione. This adduct can subsequently be converted into an oxo containing 7 membered ring of a terpene-like ring structure, as shown in FIG. 25.

Further Synthetic Examples. Further to the examples provided herein above, the disclosed synthetic methods and compounds can be further illustrated in the further synthetic examples discussed herein. The disclosed synthetic sequence comprising utilizing ketone derived Knoevenagel adducts 1 and allylic electrophiles 2/2' is shown below in Scheme 1 below. It should be noted that the schemes and compound numbering referred to herein this section "Further Synthetic Examples" pertain to the schemes disclosed herein in the immediately following paragraphs.

Scheme 1. Tunable terpenoid synthesis from abundant carbon sources.

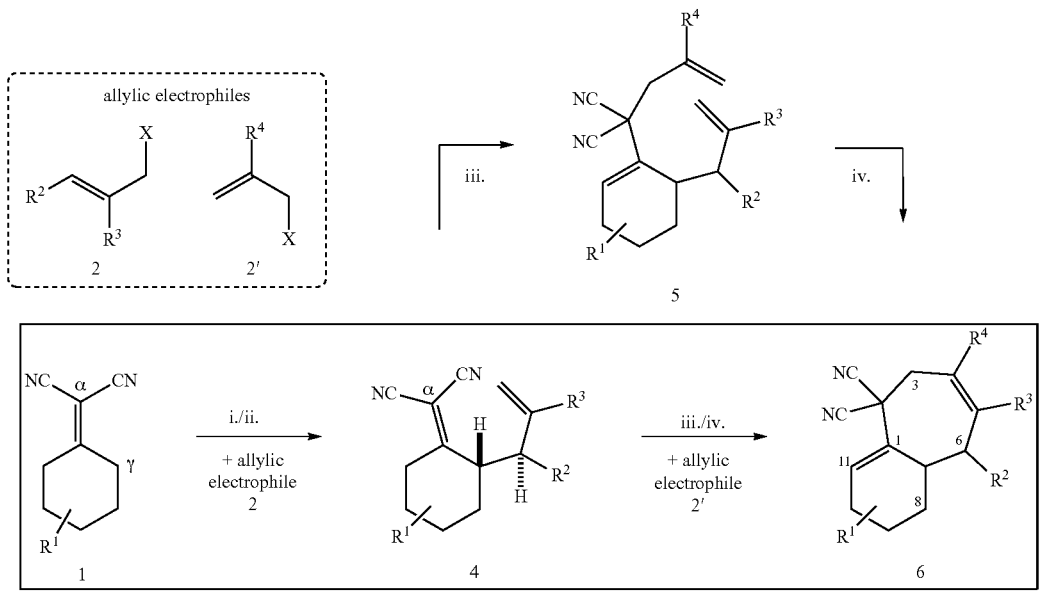

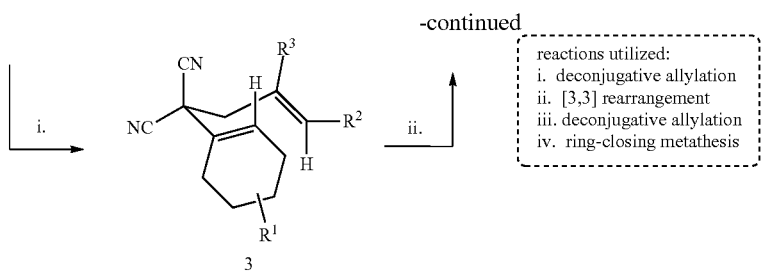

Specifically, deconjugative alkylation between Knoevenagel adduct 1 and allylic electrophile 2 yields 1,5-dienes 3, which can undergo a conjugation-driven Cope rearrangement to g-allyl Knoevenagel adduct 4. Repeating the deconjugative alkylation with allylic electrophile 2′ followed by ring-closing metathesis (RCM) yields common terpenoid cores 6 where substitution patterns can be modified by choice of Knoevenagel adduct 1 and allylic electrophiles 2 and 2′. The chemical transformations are envisioned to be operationally simple: the key C—C fragment couplings proceed via easily generated carbanions prepared from Knoevenagel adducts 1 and 4 (γ-C—H, pKa≤10/DMSO), the [3,3] rearrangement will proceed under thermal conditions and medium-sized ring synthesis by RCM is well precedented using commercial metathesis catalysts.

The architectures 6 can bear a gem-dinitrile functional group at the 2-position. The dinitrile can be important to implementing the proposed route (Scheme 1), but its incorporation can also facilitate diversification. Quaternary dinitriles and related functional groups are known to undergo a variety of reactions including decyanation, hydrolysis and other nucleophilic addition reactions. From a medicinal chemistry perspective, a nitrile is sterically small (A value=0.17), has noted metabolic stability, decreases lipophilicity, and is isosteric to a halogen. The scope of the sequence was examined with respect to the different reagent classes (Schemes 2a-2c, which are referred to collectively as "Scheme 2"). It is well precedented that alkyl halides can undergo deconjugative alkylation with Knoevenagel adducts, however, in some aspects, it may be preferable to utilize allylic acetates and carbonates due to their bench-stability. Under representative conditions, 4a was prepared by Pd-catalyzed deconjugative allylation with 2a followed by heating at 150° C. to promote [3,3] rearrangement. The sequence could be telescoped in >95% yield over the two steps. 6a was prepared by repeating the deconjugative allylation (via 5a) followed by ring-closing metathesis. A series of bicycloalkanes 6b-6j was prepared by varying the starting materials. Due to interest in unique oxidation patterns, oxygenated Knoevenagel adducts 1a-1c were utilized, and 1e to yield 6a-6c, and 6e. Oxygenated allylic electrophiles translate into unique oxidation patterns about the cycloheptyl ring (6h, 6j). Other cyclic systems could also be prepared (6d and 6f). As a final point, when terminally substituted allylic reagents are utilized for the initial alkylation (e.g., 4I and 4j), the allylic transposition results in two new stereocenters diastereoselectively.

Scheme 2a. Synthesis of uniquely functionalized and oxygenated bicycloalkanes.

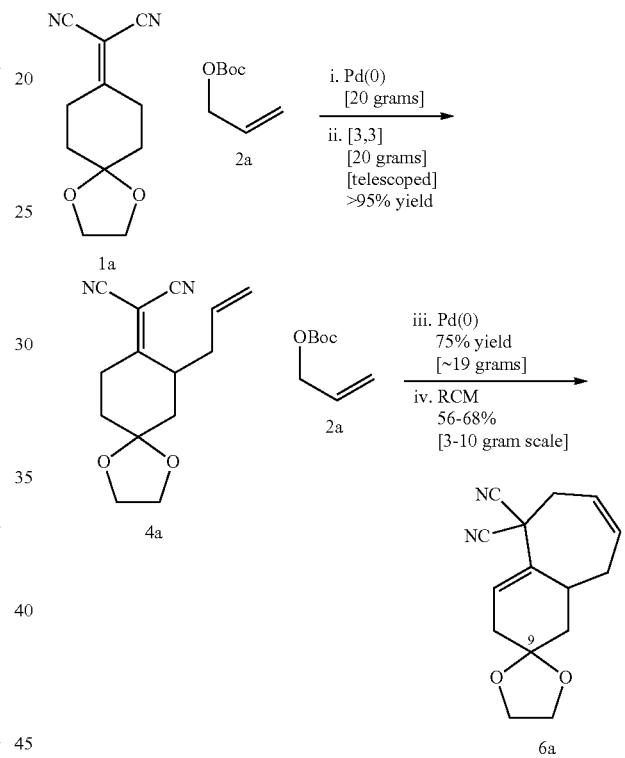

Scheme 2b. Synthesis of uniquely functionalized and oxygenated bicycloalkanes.

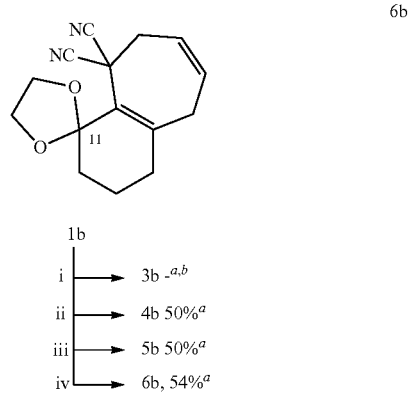

-continued
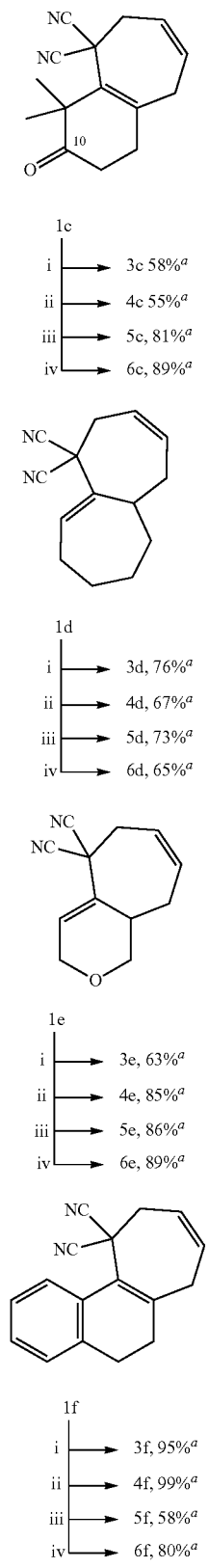
Scheme 2c. Synthesis of uniquely functionalized and oxygenated bicycloalkanes.
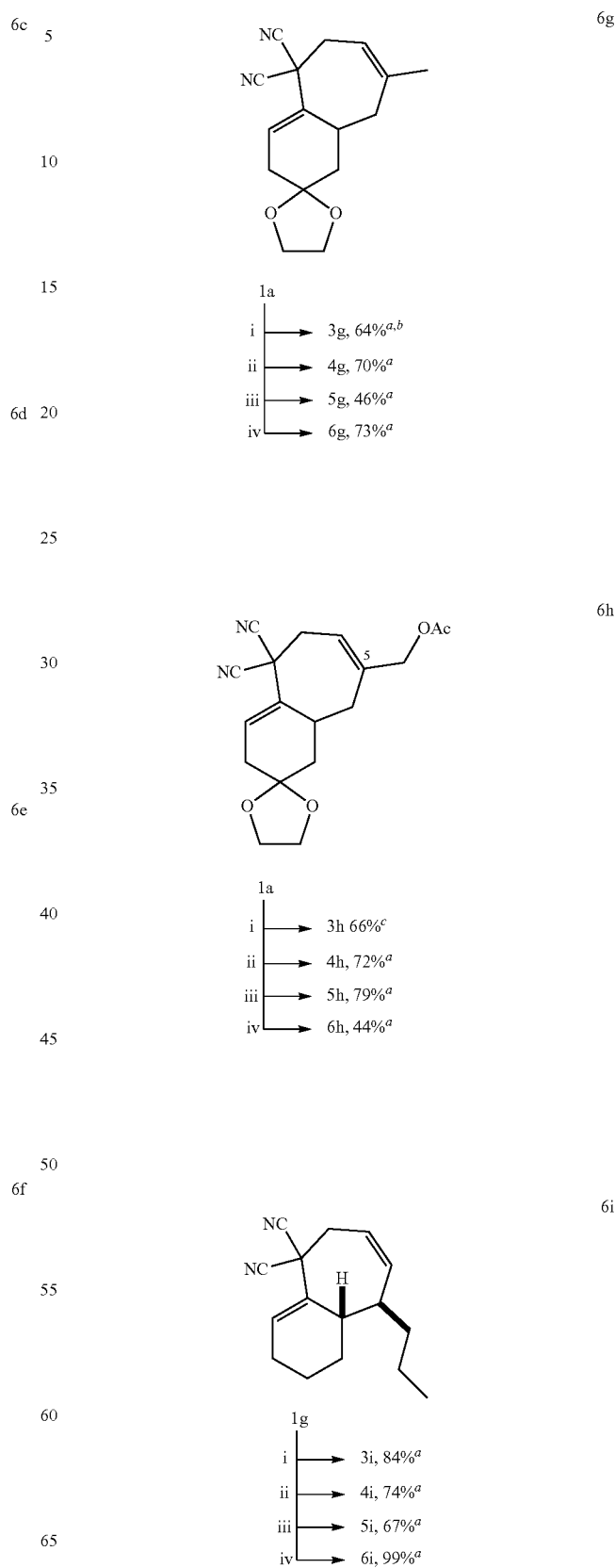

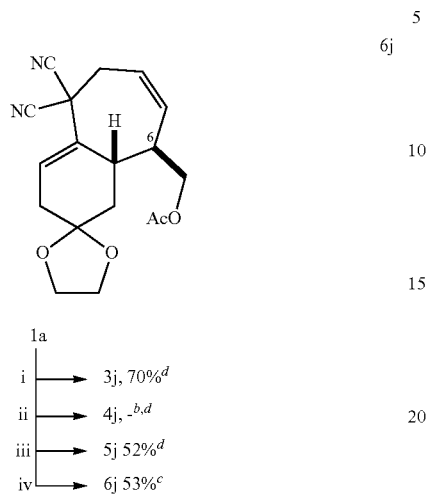

i. → 3j, 70%[d]
ii. → 4j, -[b,d]
iii. → 5j 52%[d]
iv. → 6j 53%[c]

i. 1.05 equiv. allyl acetate or carbonate, 0.50-1 mol% Pd(PPh$_3$)$_4$, THF or CH$_2$Cl$_2$, rt. ii. 140-170° C., toluene, pressure vial, iii. 1.05 equiv. allyl acetate or carbonate, 0.50-1 mol% Pd(PPh$_3$)$_4$, THF or CH$_2$Cl$_2$, iv. 1-5 mol% Grubbs II, toluene, 80° C., [a] standard scale = 50-500 mgs [b]telescoped, [c] > gram scale reaction [d] 15-30 gram scale reaction An additional unique oxidation pattern can be accessed by starting from cyclic, allylated 1,3-diones 7 (Schemes 3a-3c, collectively referred to as "Scheme 3"). Beginning with 7a, a Knoevenagel condensation yields g-allyl Knoevenagel adduct 4k, which can be processed as previously described by deconjugative allylation then ring-closing metathesis to 8-oxobicycle 6k. In addition to the 8-keto functional group in the cyclopentenone (6k) or hexenone (6l-6p), oxygenation and aliphatic substitution can be varied in the cycloheptyl ring resulting in unique bicycloalkanes (6n-6p). Furthermore, bicycloalkane 6q was prepared on the gram-scale. 6q or related structures may be useful in the synthesis of pseudoguaianolide natural products.

Scheme 3a. Synthesis of 8-oxo bicycloalkanes.

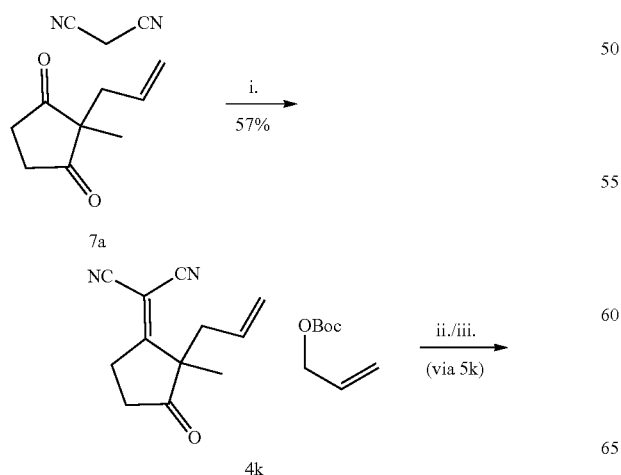

Scheme 3b. Synthesis of 8-oxo bicycloalkanes.

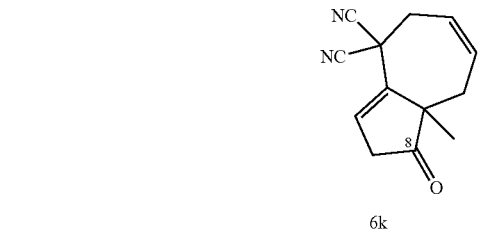

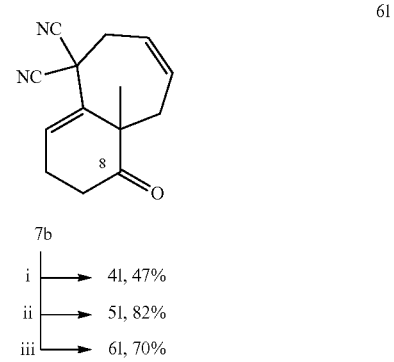

i. → 4l, 47%
ii. → 5l, 82%
iii. → 6l, 70%

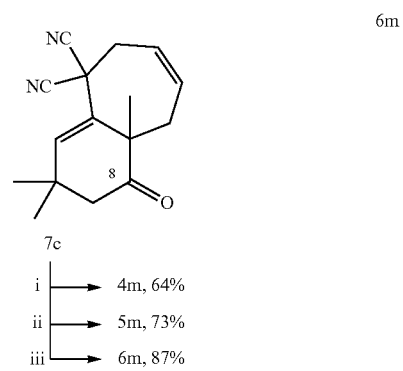

i. → 4m, 64%
ii. → 5m, 73%
iii. → 6m, 87%

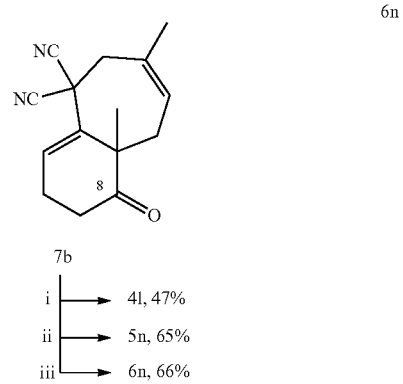

i. → 4l, 47%
ii. → 5n, 65%
iii. → 6n, 66%

-continued

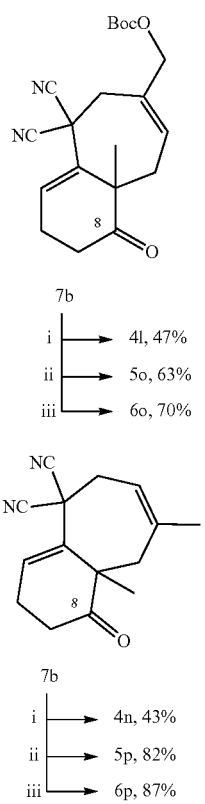

7b
i → 4l, 47%
ii → 5o, 63%
iii → 6o, 70%

7b
i → 4n, 43%
ii → 5p, 82%
iii → 6p, 87% i. NH₄OAc, AcOH, Tol, reflux, ii.1.05 equiv. allyl carbonate, 1 mol% Pd(PPh₃)₄, THF, rt. iii. 1-5 mol% Grubbs II, toluene, 80° C.

Scheme 3c. Synthesis of 8-oxo bicycloalkanes.

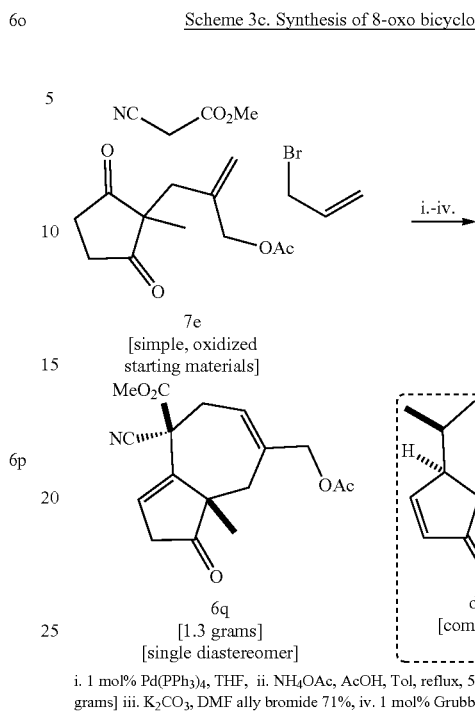

i. 1 mol% Pd(PPh₃)₄, THF, ii. NH₄OAc, AcOH, Tol, reflux, 59% over two steps [5.9 grams] iii. K₂CO₃, DMF ally bromide 71%, iv. 1 mol% Grubbs II, DCM, 80%

The use of cyclic allylic electrophile 2h (Scheme 4A) was examined. Surprisingly, it was determined that deconjugative alkylation of 1h and the cyclic allyl bromide yielded 8a, which underwent diastereoselective Cope rearrangement to 8b (two steps, 70% yield). Repeating the deconjugative allylation followed by ring-closing metathesis yielded the angularly fused tricycloalkane (two steps, 29% yield). Excitingly, this is a rapid entry into a challenging class of natural products (tigliane and daphnane).

Scheme 4a. Variations on the disclosed strategy.

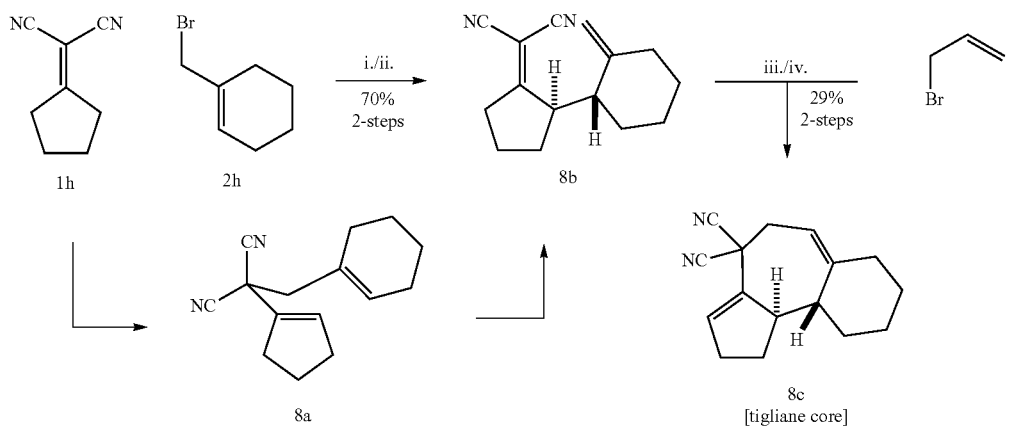

i. K₂CO₃, DMF, ii. 150° C., tol, iii. K₂CO₃, DMF iv. 1 mol% Grubbs II, tol.

Using a variant of Tunge's decarboxylative allylation allowed conversion of 9a to the 1,5-diene 9b bearing a tetrasubstituted olefin (Scheme 4B). It should be pointed out that the decarboxylative method is essential to generating the more substituted Knoevenagel adduct!s allyl anion as standard deprotonation conditions results in deprotonation from the less substituted γ-position (see many of the schemes above). Surprisingly, it was determined that a [3,3] rearrangement to prepare a quaternary center was feasible. In this case, the conjugation-driving force allows for a favorable allylic transposition. Using the standard protocol, 9c was then converted to the bicycloalkane 9d bearing an angular methyl group.

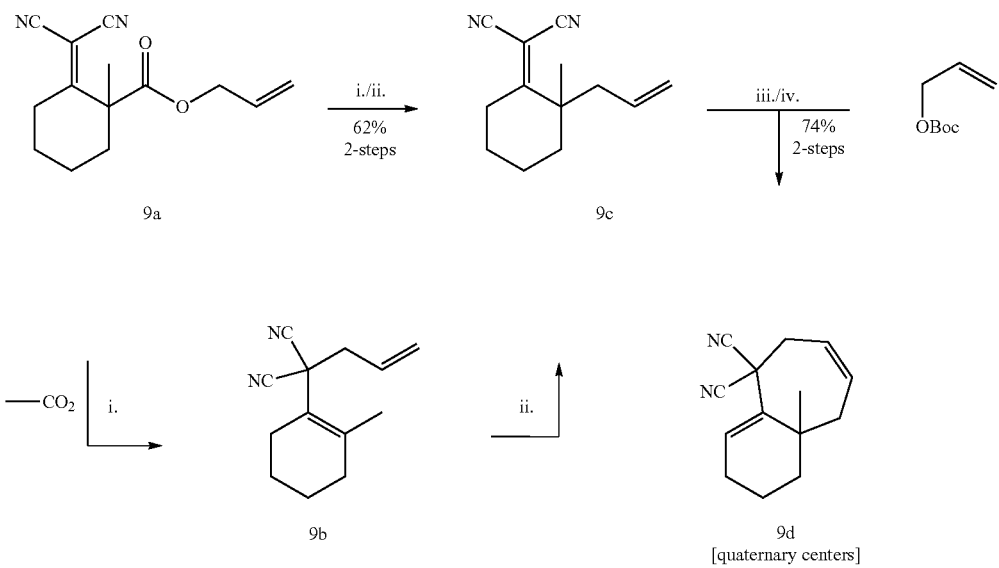

Scheme 4b. Variations on the disclosed strategy.

i. 1 mol% Pd(PPh₃)₄, THF, ii. 150° C., tol. iii. 1 mol% Pd(PPh₃)₄, iv. 1 mol% Grubbs II, tol.

An additional unique oxygenation pattern can be prepared by utilizing exocyclic 1,3-dione 10a (Scheme 4C). 10a is prepared from cyclohexanone by Claisen condensation with cinnamoyl chloride, then methylation (K2CO3, MeI). 10a was then subjected to standard Knoevenagel condensation conditions and 10b was isolated. Interestingly, the molecule contains two ketones but condensation was only observed at the cyclohexanone. The sequence is then completed as previously described to yield a 6-oxygenated scaffold 10c.

Scheme 4c. Variations on the disclosed strategy.

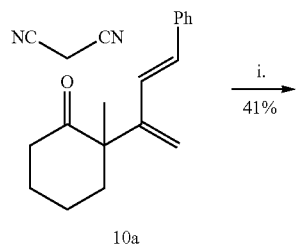

10a

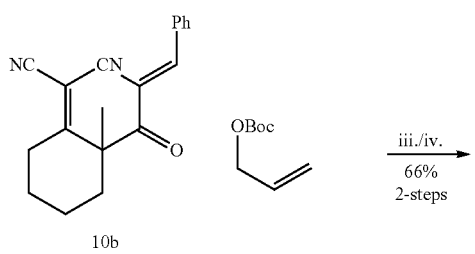

10b

-continued

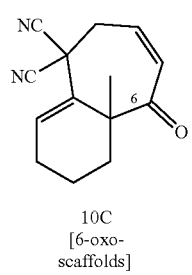

10C
[6-oxo-scaffolds]

i. NH₄OAc, PhH:AcOH, reflux, ii. 1 mol% Pd(PPh₃)₄, THF, iii. 1 mol% Grubbs II, tol The disclosed sequences immediately above terminated by ring-closing metathesis. However, other cyclization reactions can be utilized (Schemes 5a and 5b, referred to collectively as "Scheme 5"). For example, 11a, prepared by deconjugative α-allylation/[3,3] Cope rearrangement, underwent intramolecular deconjugative α-allylation to yield the decalin 11b. Though not initially of interest at the outset of our studies, decalin natural products, such as marrubiin, may be synthetically viable targets beginning from ketones, malonic acid derivatives, and bis-allylic reagents. γ-Propargyl Knoevenagel adducts 12a-b were prepared by alkylation then Knoevenagel condensation from their respective commercially available cyclic b-keto esters. Deconjugative alkylation (to 13a-b) with furfuryl bromide followed by intramolecular Diels-Alder furan (IMDAF) cycloaddition yields the tricyclic frameworks 14a-14b. Although the cycloaddition yields are modest, this has the potential to be a simple approach to diterpenoid natural product analogs related to icetexane and neodolastane families.

Scheme 5a. Other cyclization reactions in lieu of ring-closing metathesis.

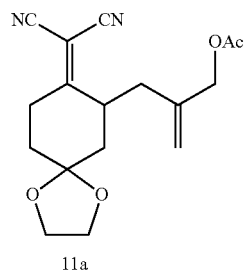

11a

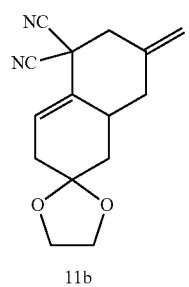 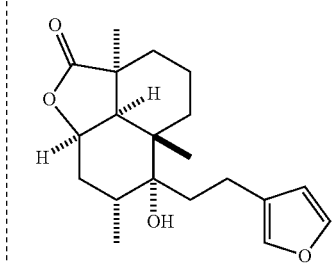

11b (+)-marrubiin
[comparative decalin
natural product]

i. K$_2$CO$_3$, 1 mol% Pd(PPh$_3$)$_4$

Scheme 5b. Other cyclization reactions in lieu of ring-closing metathesis.

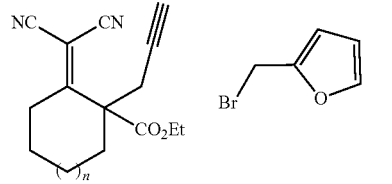

12a n = 1
12b n = 0

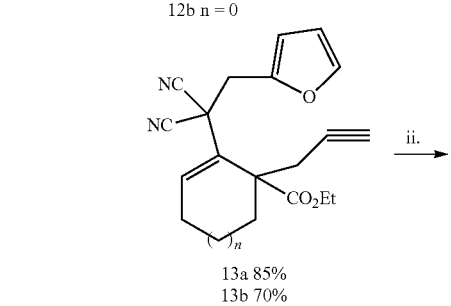

13a 85%
13b 70%

-continued

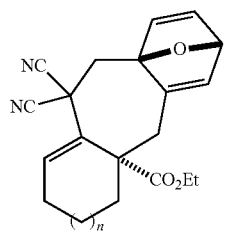

14a 49% 2:1 dr
14b 31% 20:1 dr i. KO$^t$Bu, DMSO ii.. xylene 220° C., 24 h (14a was prepared on the gram scale)

Functional group interconversions were examined (Schemes 6a-6e, collectively referred to as "Scheme 6"). Under Upjohn conditions, the lactone 15a was isolated as a single diastereomer via dihydroxylation followed by concomitant intramolecular nitrile hydrolysis. The acetal 6j could be selectively deprotected. Substrate 6k underwent a variety of chemoselective transformation in good to excellent yield including hydrogenation, reductive decyanation, dehydrocyanation, and ketone reduction. Building block 6q also underwent reductive decyanation diastereoselectively yielding substrate 15g bearing an ester moiety. Alternatively ester hydrolysis and decarboxylation provides access to the mononitrile 15h. 16a was prepared by the standard procedure on the 10-gram scale. The nitrile could be converted to the methyl ester 15i diastereoselectively under simple conditions. Conditions for the synthesis of the allyl ester 15j were examined, which are precedented to undergo a variety of chemical transformation including decarboxylative protonation (deprotection) and allylation. Finally, using Dash's simple protocol for nitrile hydrolysis, amide 15k and tricyclic imide 15l were prepared.

Scheme 6a. Examples of functional group interconversion reactions.

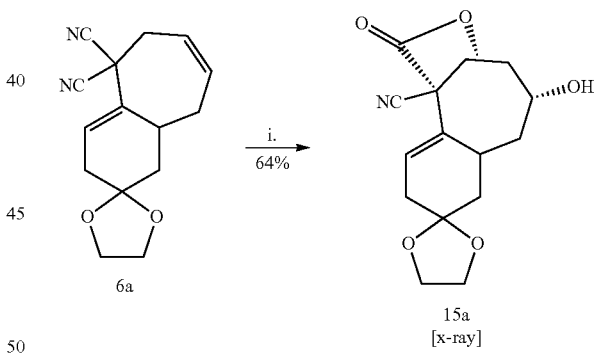

6a  15a [x-ray]

Scheme 6b. Examples of functional group interconversion reactions.

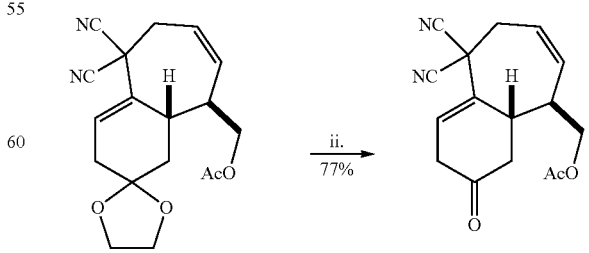

6i  15b

Scheme 6c. Examples of functional group interconversion reactions.
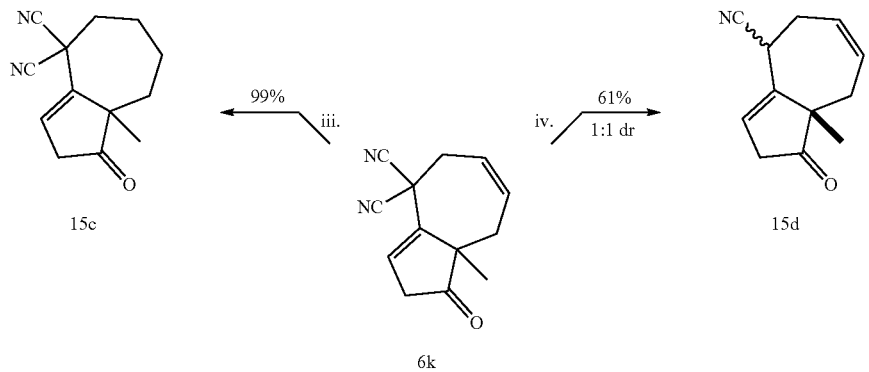
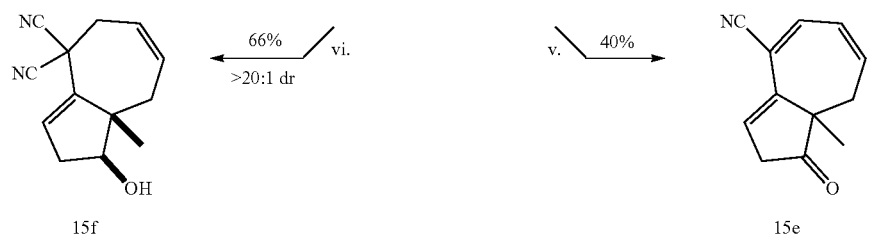
Scheme 6d. Example of functional group interconversion reactions.
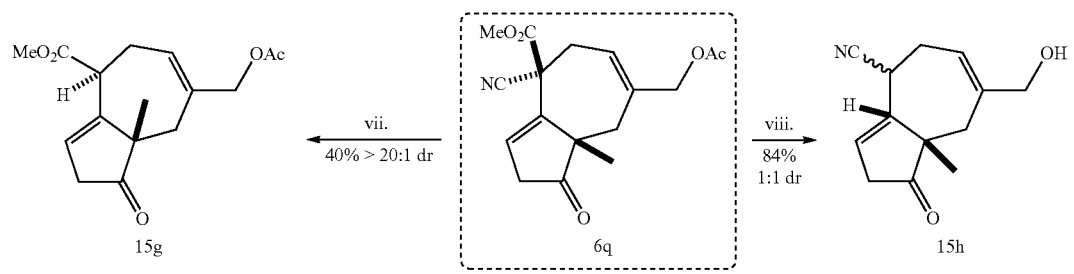

Scheme 6e. Examples of functional group interconversion reactions.

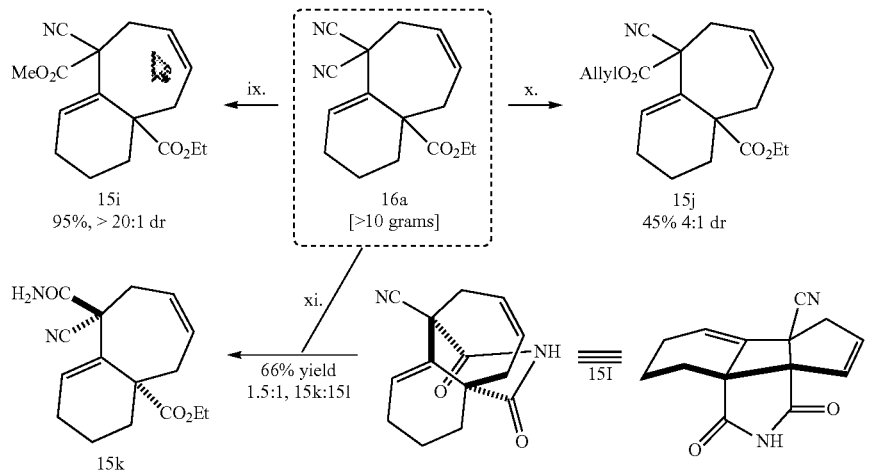

i. 3 mol % OsO$_4$, 1.5 equiv. NMO, in acetone/H$_2$O, rt, 2 h, ii. 10 mol % I$_2$, acetone reflux, 12 h, iii. 7% w/w Pd/C, H$_2$, THF, 4 h, iv. 3 equiv. LN (1M in THF), then MeOH/NH$_4$Cl, -78° C., 2 min, v. 1.5 equiv. NaH, DMF, 5 min, vi. 1 equiv. NaBH$_4$, MeOH, 0° C., 15 min., vii. 3 equiv. LN (1M in THF), then MeOH/NH$_4$Cl, -78° C., viii. (a) 3 equiv. NaOH, H$_2$O/MeOH, (b) 10 mol % Cu$_2$O, MeCN, 80° C., ix. 5 equiv. K$_2$CO$_3$, MeOH, then 2M HCl, x. K$_2$CO$_3$, allyl alcohol xi. 3 equiv. KO$^t$Bu, tert-amyl alcohol 0° C.

Further experimental details for the foregoing further synthetic methods are disclosed herein below.

1. General Experimental Details. All commercial materials were used without further purification. 2-methyl-1,3-cycloalkanones were either commercial or prepared by methylation from 1,3-cycloalkanones by the literature procedure (Lertpibulpanyaa, D.; Marsden, S. P. Org. Biomol. Chem. 2006, 4, 3498). 2-cinnamoylcyclohexan-1-one 10a was prepared according to the previously reported procedure (Casey, M; Donnelly, J. A.; Ryan, J. C.; Ushioda, S. ARK/ VOC 2003 (vii) 310). Allylated diones 7a-d were prepared according to published procedure (Trost, B. M.; Curran, P. D. J. Am. Chem. Soc. 1980, 102 (17), 5699) using different electrophiles. All other synthetic protocols are outlined below. $^1$H NMR and $^{13}$C NMR spectra were recorded in CDCl$_3$ using a 500 MHz spectrometer (with CHCl3 residual peak as an internal standard). All $^{13}$C NMR spectra were recorded with complete proton decoupling. HRMS data were recorded on Agilent Time of Flight 6200 spectrometer. Reaction progress was monitored by thin-layer chromatography (TLC) and visualized by UV light, phosphomolybdic acid stain, and KMnO$_4$ stain. All reactions were carried out using anhydrous solvents obtained dried by passing through activated alumina columns.

2. General procedure A: synthesis of allyl carbonate derivatives. The reaction scheme is as follows:

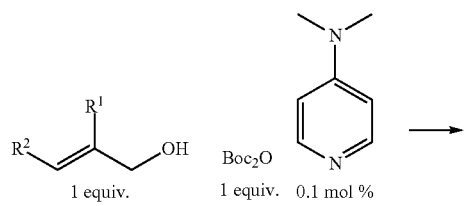

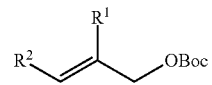

Allyl alcohol (1 equiv.) and di-tert-butyl dicarbonate (1 equiv.) was dissolved in THF (~1M or neat). DMAP (0.1 mol %) was added, and then the solution was gently heated using a heat gun until effervescence was observed. After completion (as determined by no more effervescence observed), the mixture was filtered through a silica plug, and the solvent was evaporated. Vacuum distillation or column chromatography (hexanes-ethyl acetate) affords the pure product.

3. General procedure B: synthesis of allyl acetate derivatives. The reaction scheme is as follows:

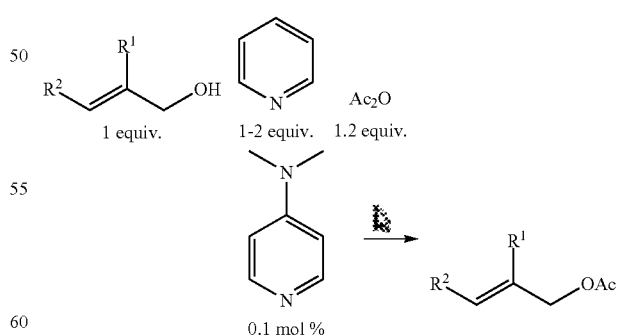

Allyl alcohol (1 equiv.) and acetic anhydride (1.2 equiv.) were dissolved in DCM (~1M) at 0° C. Pyridine (1 equiv.) and DMAP (0.1 mol %) were then added. The reaction mixture was stirred at 0° C. for 30 min. and was then allowed to reach room temperature. After completion, the mixture was quenched with 2N HCl and the organic layer was washed with H$_2$O, brine and was dried over Na$_2$SO$_4$. Careful evaporation of the remaining solvents affords the pure compound without further purification.

4. General procedure C: Synthesis of Knoevenagel adducts. The reaction scheme is as follows:

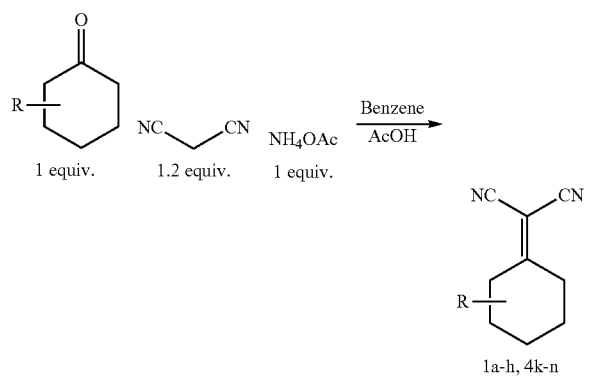

All reaction components were dissolved in benzene/glacial acetic acid (respectively 4:1, 1.0M) and refluxed using a Dean-Stark apparatus until completion as monitored by TLC. The mixture was then cooled to room temperature and the solvents were evaporated. The residue was diluted with EtOAc and washed with a saturated solution of NaHCO$_3$, water, and brine. The organic layer was dried over Na$_2$SO$_4$, filtered and the volatile components were evaporated in vacuo. Pure compounds were isolated via column chromatography (hexanes-ethyl acetate).

5. General procedure D: Pd-catalyzed α-allylation of Knoevenagel adducts. The reaction scheme is as follows:

Tetrakis(triphenylphosphine)palladium(0) (1 mol %) was charged in a flame dried Schlenk flask under a nitrogen atmosphere and dissolved in THF (0.5M with respect to the limiting reagent). Allyl acetate (1.1 equiv.) or allyl carbonate (1.1 equiv.) derivative was then added to the reaction mixture directly followed by the substrate (1 equiv.). The reaction mixture was stirred at room temperature or 40° C. until completion. After reaction, the crude mixture was concentrated in vacuo and purified via column chromatography (hexanes-ethyl acetate). NOTE: When allylic acetates are utilized, finely ground K$_2$CO$_3$ (1.5 equiv.) is added to the reaction mixture.

6. General procedure E: [3, 3] Sigmatropic rearrangement. The reaction scheme is as follows:

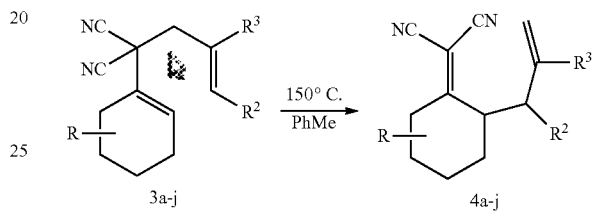

α-Allylated Knoevenagel adduct 3a-*j* were charged in a pressure vial and dissolved in toluene (~0.5M) heating at 150° C. (unless otherwise specified) for the indicated period of time afforded the rearranged products 4a-j. Toluene was removed in vacuo and the crude products were purified by column chromatography (hexanes-ethyl acetate).

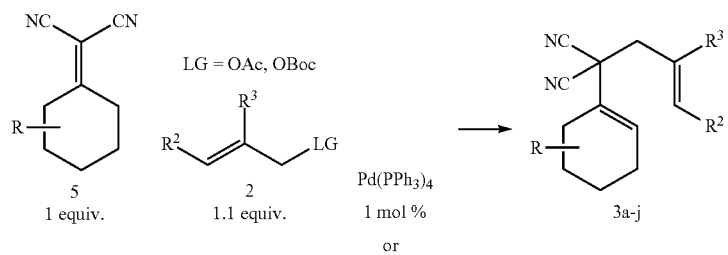

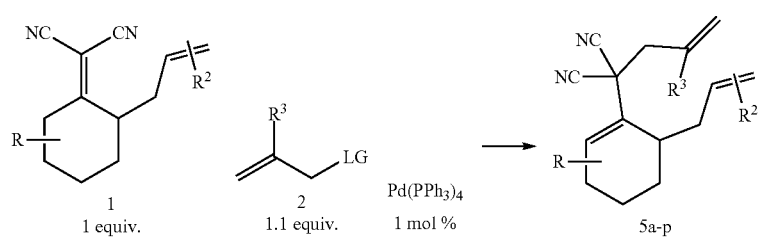

9.4 Ring-closing metathesis of SI-2 to 10c. The reaction scheme is as follows:

7. General Procedure F: Ring Closing Metathesis. The reaction scheme is as follows:

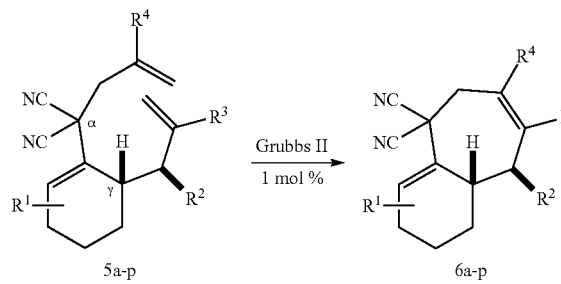

Grubbs II catalyst (1 mol %) was charged into a flame-dried Schlenk flask under a nitrogen atmosphere and dissolved in dry toluene. In a separate vessel, α,γ-diallylated Knoevenagel adduct 5a-p was dissolved in dry toluene unless otherwise specified (final concentration~0.05M) and then added via syringe to the reaction vessel. The reaction mixture was stirred at 80° C. (unless specified differently below). After reaction, the crude mixture was passed through a short pad of silica gel and eluted with dichloromethane to remove particles of the catalyst. The solvents were removed in vacuo and the pure compound was purified via column chromatography (hexanes-ethyl acetate).

8. Synthesis of decalin 11b. The reaction scheme is as follows:

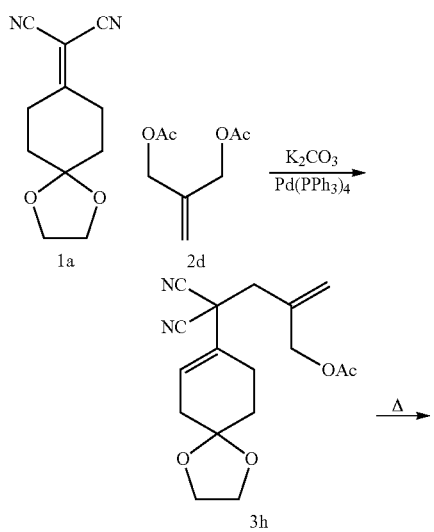

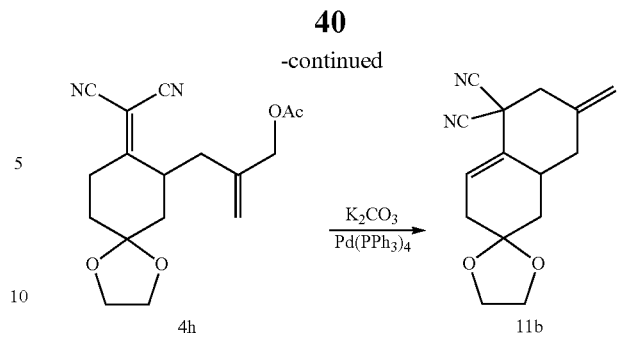

11b was prepared using general procedures C, D and E.

8.1. Intramolecular allylation on substrate 4h (11b). The reaction scheme is as follows:

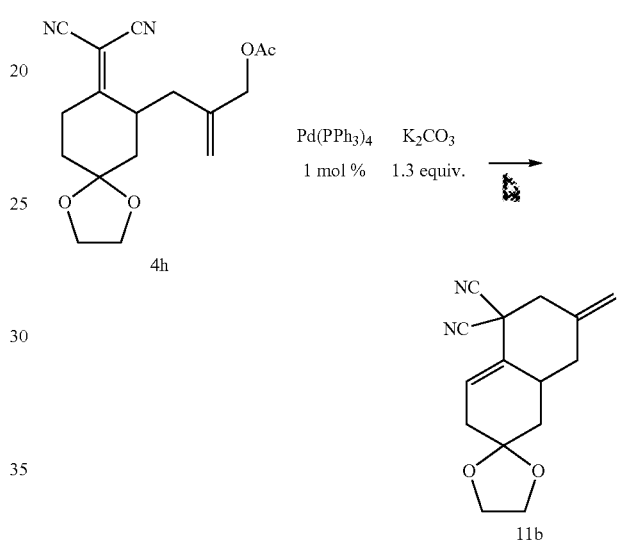

Pd(PPh$_3$)$_4$ (1.1 mg, 0.0001 mmol, 1 mol %) was charged in a flame-dried Schlenk flask under a nitrogen atmosphere and dissolved in anhydrous CH$_2$Cl$_2$. Ground K$_2$CO$_3$ (20 mg, 0.142 mmol, 1.5 equiv.) was then added followed by substrate 4h (30 mg, 0.095 mmol, 1.0 equiv.) (concentration~0.5 M). The reaction mixture was stirred at room temperature and after 2 hours, the reaction was complete. Purification was achieved by directly passing the reaction through a short column using a solvent mixture of 4:1 hexanes/EtOAc. Concentration of the solution gave 11b as a colorless oil (20 mg, 82%).

9. Synthesis of 6-oxo-terpenoid scaffold 10c. The reaction scheme is as follows:

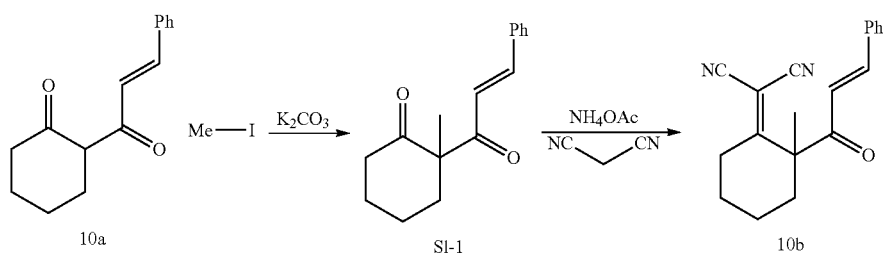

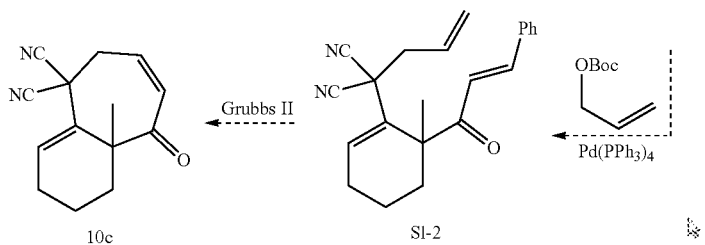

9.1. Methylation of 10a—SI-1. The reaction scheme is as follows:

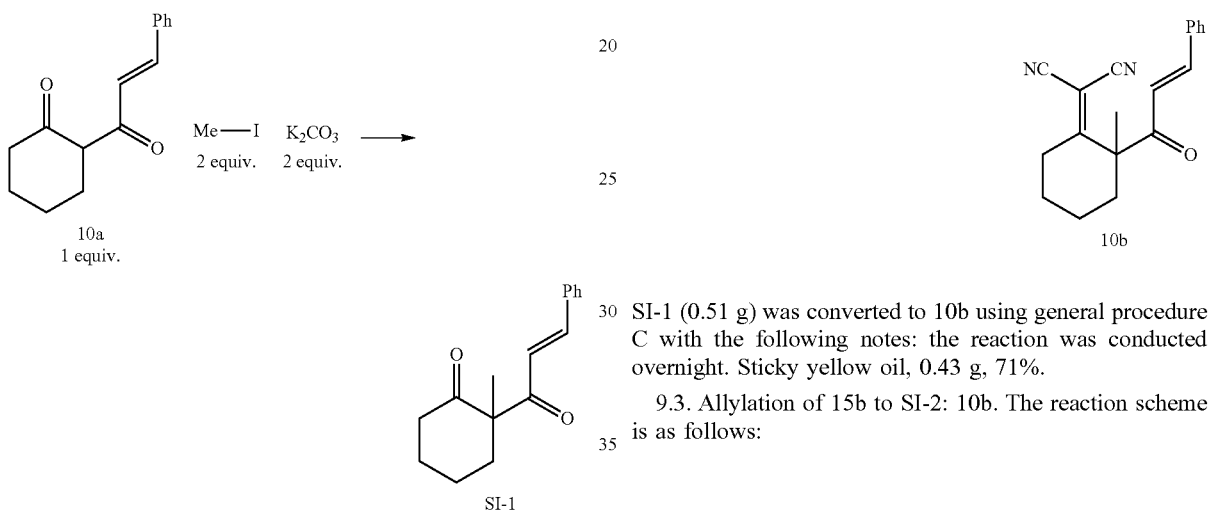

Ground K$_2$CO$_3$ (2.4 g, 17.5 mmol, 2 equiv.) was added to 50 mL DMSO in a 250 mL flask under N$_2$. 10a (2 g, 8.7 mmol, 1 equiv.) in 50 mL DMSO was then added dropwise at room temperature to the reaction mixture. The reaction was stirred for 5 min. Finally, MeI (2.5 g, 17.5 mmol, 2 equiv.) was added dropwise. After 45 min., the reaction mixture was quenched with 1M HCl (50 mL) and diluted with EtOAc (50 mL). The organic layer was washed two times with H$_2$O and brine (25 mL each time), and finally dried over Na$_2$SO$_4$. Solvents were removed in vacuo and the residue was purified via column chromatography (hexanes-ethyl acetate 20:1) yielding SI-1 as white crystals (1.24 g, 58%).

9.2. Knoevenagel condensation of SI-1 to 10b. The reaction scheme is as follows:

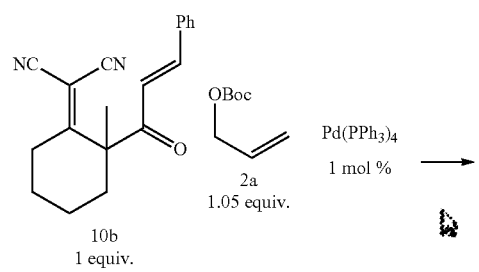

SI-1 (0.51 g) was converted to 10b using general procedure C with the following notes: the reaction was conducted overnight. Sticky yellow oil, 0.43 g, 71%.

9.3. Allylation of 15b to SI-2: 10b. The reaction scheme is as follows:

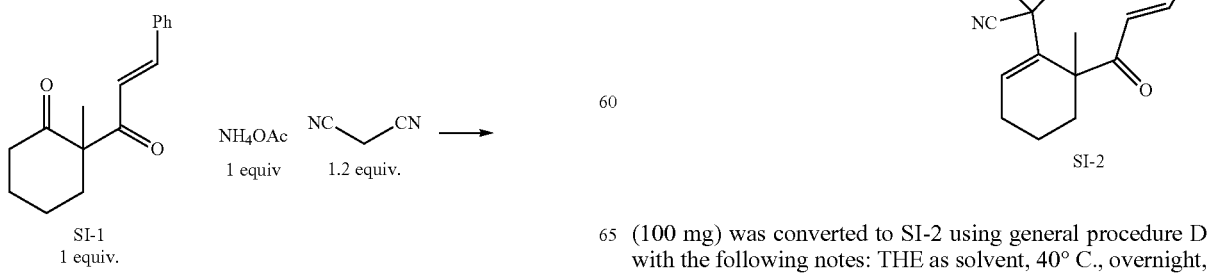

(100 mg) was converted to SI-2 using general procedure D with the following notes: THF as solvent, 40° C., overnight, electrophile 2a. Sticky yellow oil, 0.093 g, 82%.

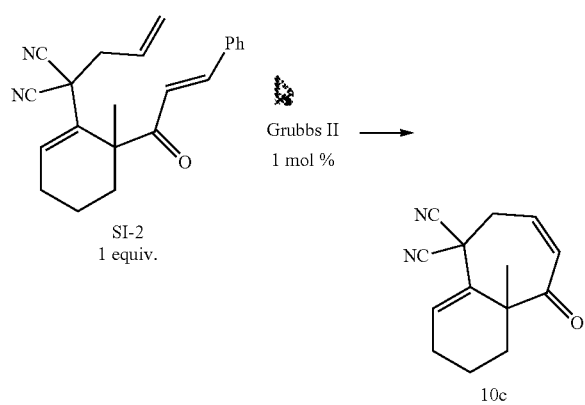

SI-2 (60 mg) was converted to 10c using general procedure F with the following notes: conducted at 80° C., overnight. White solid, 0.033 g, 80%.

10. Synthesis of tigliane core 8c. The reaction scheme is as follows:

2-cyclopentylidenemalononitrile 1h was prepared according to general procedure C. 1-(bromomethyl)cyclohex-1-ene 2h was prepared according to literature procedure (Hyeon Park, Ho-Keun Lee, Tae-Lim Choi *J. Am. Chem. Soc.* 2013, 135, 1076). Sodium hydride (54 mg, 2.27 mmol, 1.5 equiv.) was charged in a 25 mL flame-dried Schlenk flask under $N_2$ and suspended in dry DMF (8 mL). The suspension was then cooled down to 0° C. in an ice bath. 2-cyclopentylidenemalononitrile 1h (200 mg, 1.51 mmol) in 2 mL DMF was then added dropwise to the previous solution at 0° C. The resulting mixture was stirred for 10 min. at this temperature. Lastly, 1-(bromomethyl)cyclohex-1-ene 2h (318 mg, 1.82 mmol, 1.2 equiv.) was added dropwise. After 2 h, the reaction mixture was quenched with $H_2O$ (10 mL) and the resulting aqueous mixture was extracted with EtOAc. The organic layer was then washed with brine (2×15 mL), dried over $Na_2SO_4$, then the volatiles were evaporated in vacuo. The final product 8a was obtained after column chromatography (hexanes-ethyl acetate 50:1) as a white solid (336 mg, 98%).

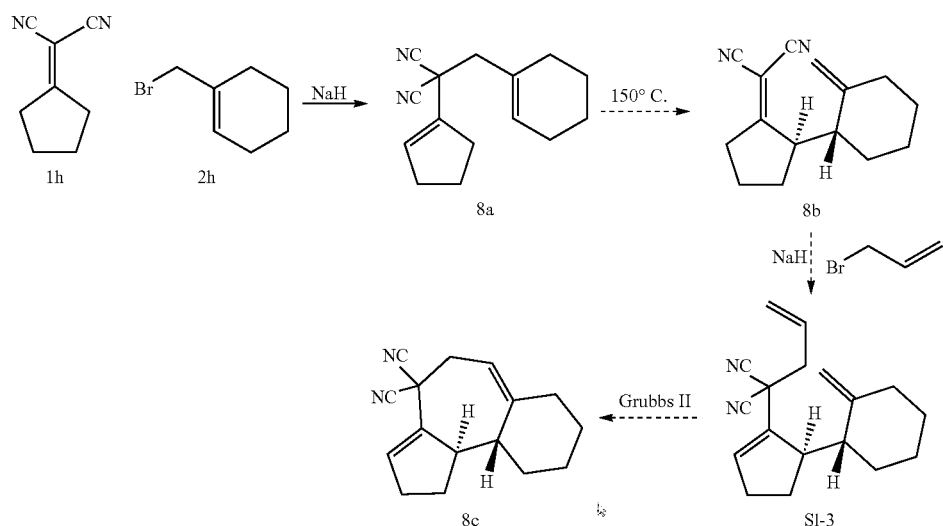

10.1. Alkylation of Knoevenagel adduct 1h with 2h. The reaction scheme is as follows:

10.2. Cope Rearrangement of 8a to 8b. The reaction scheme is as follows:

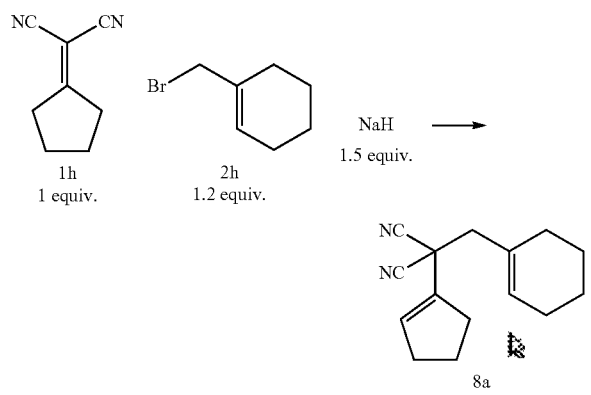

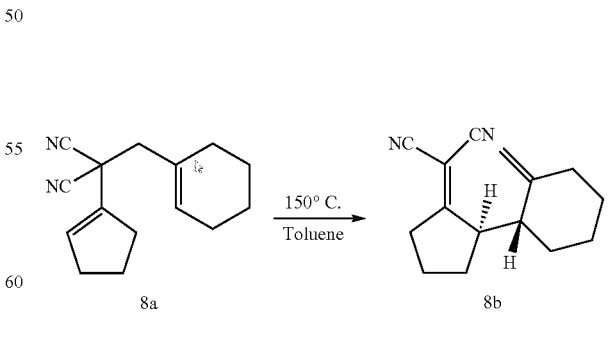

8b was prepared from 8a (210 mg) by general procedure E with the following notes: Conditions: 4.5 h; Light yellow oil, 0.147 g, 70%, >20:1 dr.

10.3. Allylation of 12b with allyl bromide. The reaction scheme is as follows:

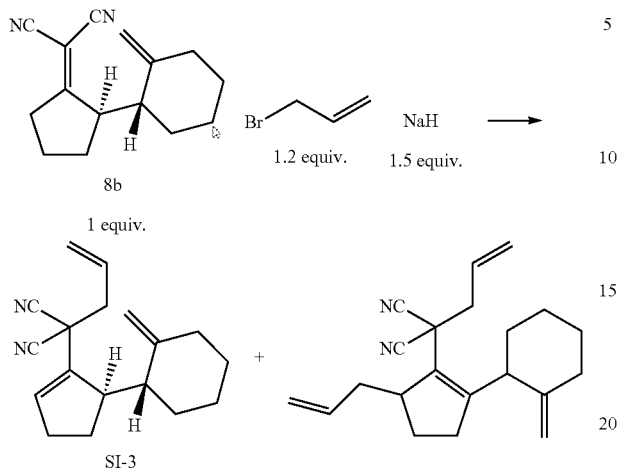

Sodium hydride (23 mg, 0.97 mmol, 1.5 equiv.) was charged in a 25 mL flame-dried Schlenk flask under a nitrogen atmosphere and suspended in dry DMF (8 mL). The suspension was then cooled to 0° C. in ice bath. 8b (147 mg, 0.65 mmol) in 2 mL DMF was then added dropwise to the previous solution at 0° C. The resulting mixture was stirred for 10 min. at this temperature. Allyl bromide (0.067 mL, 0.78 mmol, 1.2 equiv.) was added dropwise. After 45 min., the reaction mixture was quenched with $H_2O$ (10 mL) and the resulting aqueous mixture was extracted with EtOAc (15 mL). The organic layer was then washed with brine twice and dried over $Na_2SO_4$. The desired product was obtained after column chromatography (hexanes-ethyl acetate 50:1) as an inseparable mixture with bis-allylated byproduct in 5:1 ratio (128 mg, ~86%). NMR reprint of the mixture is available. HRMS, along with NMR, were used to identify the product and byproduct in the mixture. The mixture SI-3 was subjected to the next step.

10.4. Ring Closing Metathesis on mixture SI-3 to 8c. The reaction scheme is as follows:

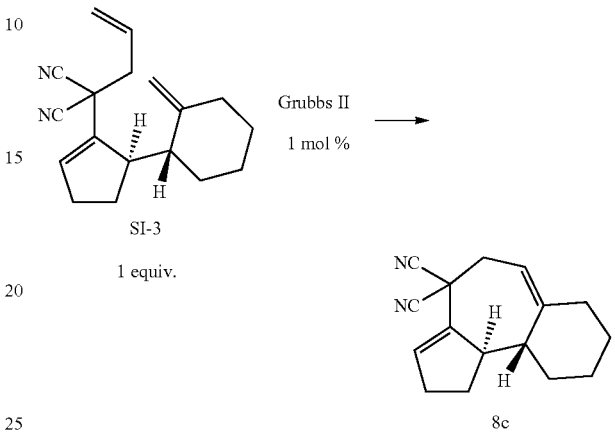

Prepared from mixture SI-3 by general procedure F with the following notes: Conditions: 1 mol % Grubbs II, DCM, reflux, overnight Clear oil, 0.024 g, 29%, purified via preparative TLC (Hexanes-Ethyl acetate 10:1).

11. Strategy toward 9d. The reaction scheme is as follows:

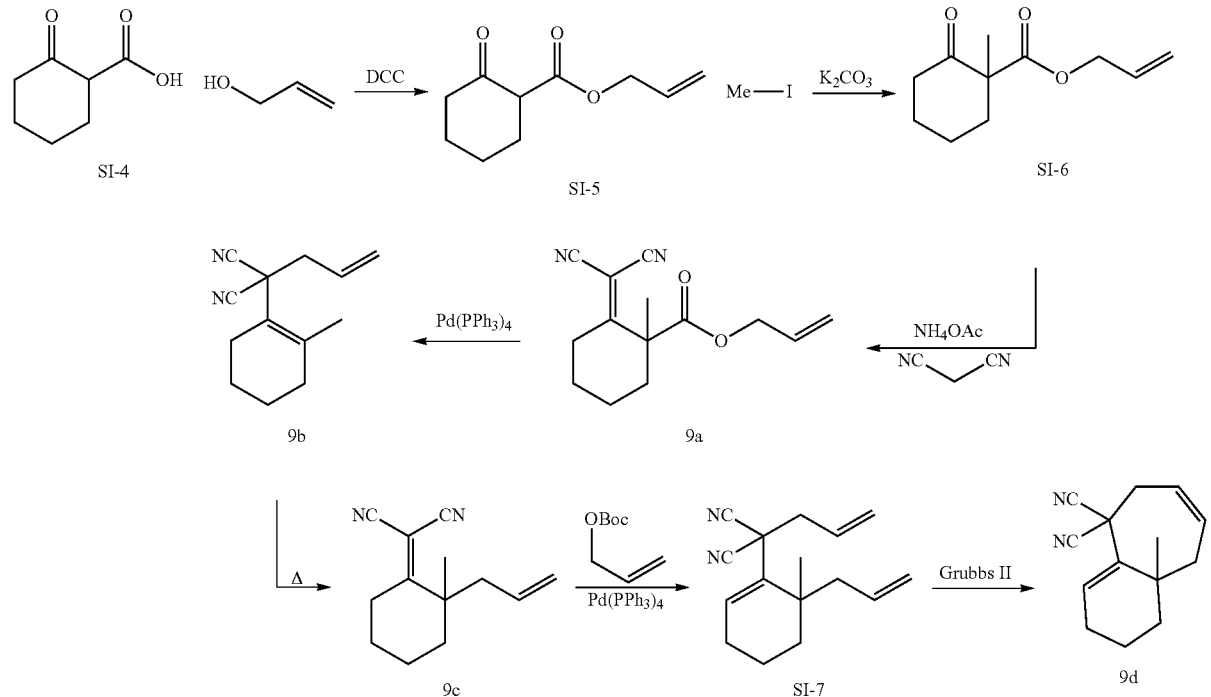

SI-4 was obtained as a white solid following a known procedure (10.59 g, 85%) and analytical data are identical to those in the reference (Sparrow, J. K.; Carley, S.; Söhnel, T.; Barker, D.; Brimble, M. A. *Tetrahedron*, 2015, 71, 2210).

11.1. Esterification of SI-4 (SI-5). The reaction scheme is as follows:

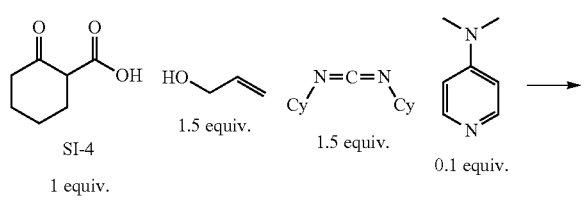

To a stirring solution of SI-4 (1.0 g, 7.03 mmol, 1 equiv.) in anhydrous CH$_2$Cl$_2$ (50 mL) was added allyl alcohol (613 mg, 10.55 mmol, 1.5 equiv.) and N,N-dimethylaminopyridine (DMAP) catalyst (86 mg, 0.70 mmol, 0.1 equiv.). The resulting solution mixture was cooled down to 0° C. before and a solution of dicyclohexylcarbodiimide (DCC) in CH$_2$Cl$_2$ (25 mL) was added dropwise. The reaction mixture was then allowed to stir and warm up to room temperature overnight. The reaction mixture was filtered twice to remove precipitated urea.

Concentration of the solution gave an oil which was dissolved in EtOAc. The latter was washed with a solution of 1M HCl (2×25 mL), NaHCO$_3$ (2×20 mL) and brine (2×20 mL) and dried over anhydrous Na$_2$SO$_4$. Concentration by rotary evaporation and purification by column chromatography gave the ketoester SI-5 (1.19 g, 6.53 mmol, 93%). Analytical data are identical to those in the reference (Kong, C.; Driver, T. G. Org. Lett, 2015, 17, 802).

11.2. Methylation of ketoester SI-5 (SI-6). The reaction scheme is as follows:

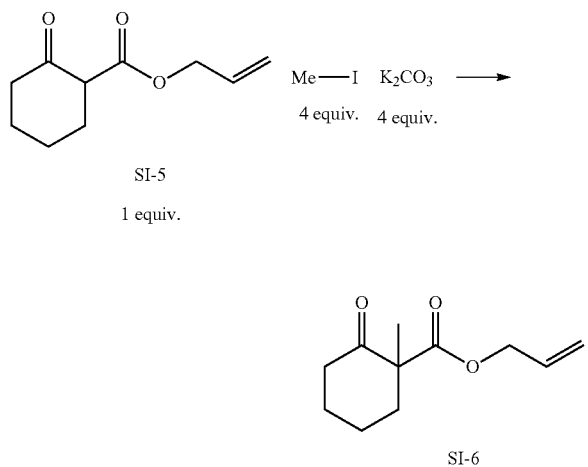

SI-5 (3 g, 16.46 mmol, 1 equiv.) was dissolved and stirred in dry acetone (200 mL). Ground K$_2$CO$_3$ (9.10 g, 65.85 mmol, 4 equiv.) was then added to the solution, subsequently followed by methyl iodide (9.35 g, 65.85 mmol, 4 equiv.) and the reaction mixture refluxed overnight. After the allotted reaction time, the reaction was brought to room temperature and concentrated by rotary evaporation. The residue was taken up in EtOAc and washed with HCl 1M, a saturated solution of Na$_2$S$_2$O$_3$, brine and was dried over anhydrous Na$_2$SO$_4$. Concentration and purification by chromatography gave the desired methylated product SI-6 with a yield of 75% (2.43 g, 12.38 mmol). Analytical data are identical to those in the reference (Minami, I.; Nisar, M.; Yuhara, M.; Shimizu, I.; Tsuji, J. Synthesis, 1987, 11, 992).

11.3. Knoevenagel condensation of malononitrile with SI-6. The reaction scheme is as follows:

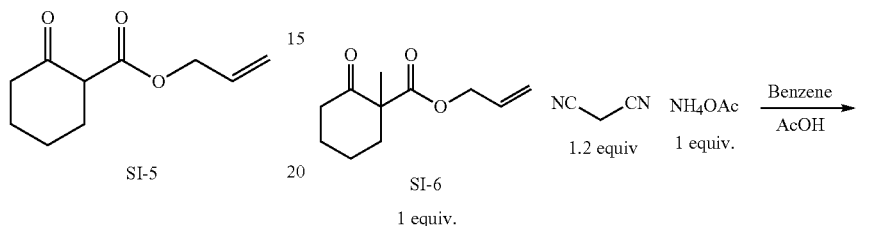

Prepared from SI-6 by general procedure C with the following notes: Conditions: overnight, reflux (bath temperature=130° C.). Yellow oil, 1.029 g, 55%.

11.4. Decarboxylative allylation of 9a. The reaction scheme is as follows:

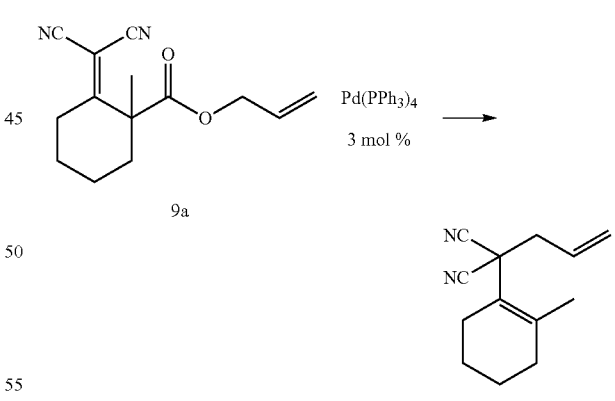

To a flame-dried Schlenk flask charged with Pd(PPh$_3$)$_4$ (43 mg, 0.037 mmol, 3 mol %) was added anhydrous THF (6 mL). Adduct 9a (300 mg, 1.23 mmol, 1 equiv.) was added to the stirring solution and fully converted after 2 minutes. Filtration of the reaction solution through a pad of silica gel using a 4:1 mixture of hexanes/EtOAc as eluent afforded a yellow solution which was concentrated by rotary evaporation. Purification by column chromatography gave the decarboxylation product 9b as a clear oil, 0.204 g, 83%.

11.5. Cope rearrangement from 9b to 9c. The reaction scheme is as follows:

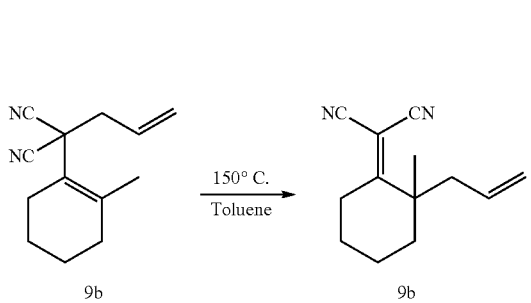

9c was prepared from 9b (100 mg) by general procedure E with the following conditions: 20 hours. Colorless oil, 0.084 g, 84%.

11.6. Allylation of 9c (SI-7). The reaction scheme is as follows:

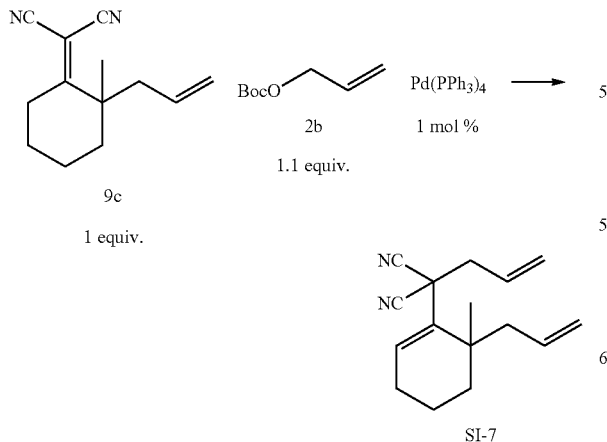

SI-7 was prepared from 9c (50 mg) by general procedure D with the following conditions: DCM, room temperature, 40 min., electrophile 2b. Colorless oil, 0.059 g, 98%.

11.7. Ring closing metathesis of SI-7 (9d). The reaction scheme is as follows:

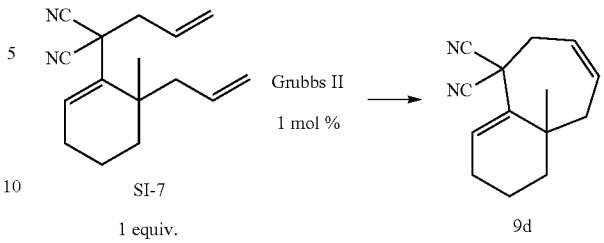

9d was prepared from SI-7 (50 mg) by general procedure F with the following conditions: PhMe, 100° C., 4 hours. Grubbs II catalyst, 1 mol %. Colorless oil, 0.039 g, 88%.

12. Protocol for the synthesis of tricyclic scaffolds 14a-14b from 12a-12b. The reaction scheme is as follows:

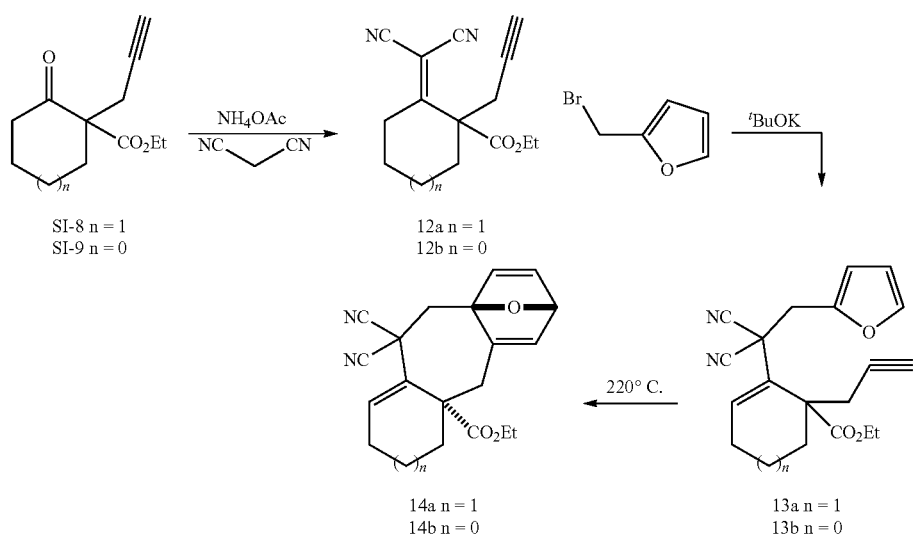

12.1. Preparation of SI-8 and SI-9. The reaction scheme is as follows:

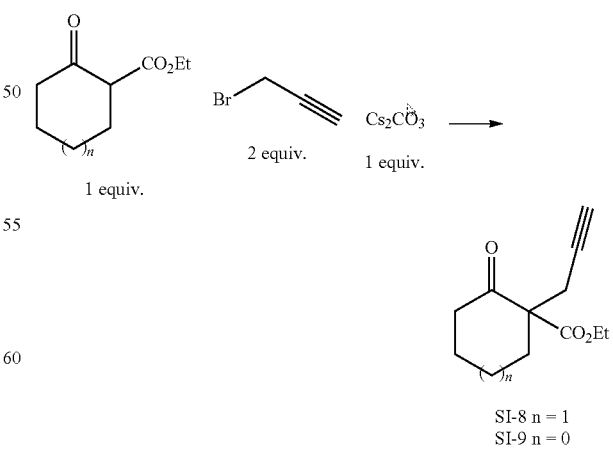

Propargyl bromide (2 equiv.) was added to a mixture of ethyl 2-oxocyclohexane-1-carboxylate or ethyl 2-oxocyclopentane-1-carboxylate (1 equiv.) and Cs₂CO₃ (1 equiv.) in acetone (0.4 M) and the resulting mixture was stirred overnight at rt. After completion, the reaction mixture was filtered over Celite and the filtration pad was washed with acetone. The solvent was removed in vacuo and the crude product was obtained which could be used in the next step without further purification. Analytical data are identical to those in the reference (Barbé, F.; Bétournay, G.; Bellavance, G.; Barriault L. *Org. Lett.* 2009, 11 (18), 4236).

12.2. Knoevenagel condensation of SI-8 and SI-9 to 12a-b. The reaction scheme is as follows:

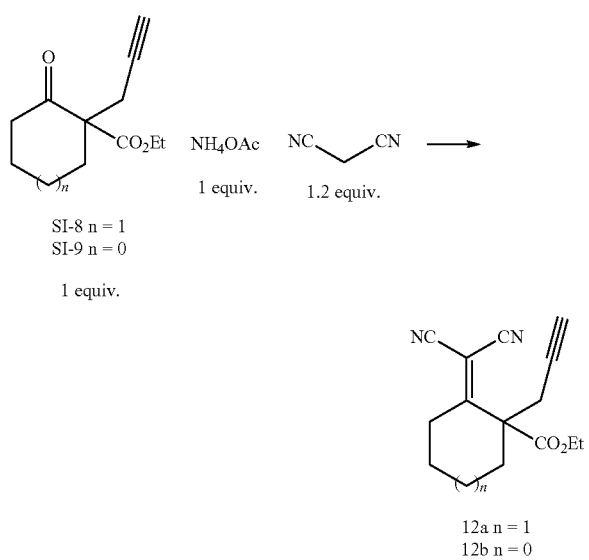

Prepared according to the general procedure C with the following notes: the reactions were conducted overnight. 12a isolated as yellow oil (1.9 g, 71%) and 12b isolated as pale yellow oil (1.6 g, 61%).

12.3. Alkylation of Knoevenagel Adducts 12a-b to 13a-b. The reaction scheme is as follows:

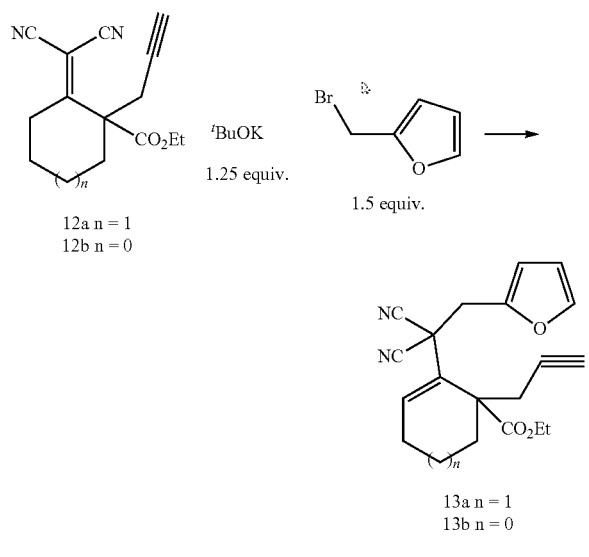

A 100-mL round-bottom flask equipped with a stir bar was charged with tBuOK (1.25 equiv.) and DMSO. A solution of the Knoevenagel adduct 12a or 12b (1 equiv.) in DMSO (final concentration 0.2 M) was added slowly over 5 minutes at room temperature and the resulting mixture was stirred for 1 h. Then, 2-(bromomethyl)furan (1.5 equiv.) was added, and the resulting mixture was stirred for 12 h at room temperature. After completion, the reaction mixture was quenched with a saturated aqueous solution of NH₄Cl and extracted with ether.

The ether layer was dried over Na₂SO₄ and concentrated in vacuo. The crude product was purified via column chromatography (hexanes-ethyl acetate 20:1) yielding respectively 13a as a pale yellow liquid (4 g, 85%) and 13b as pale yellow liquid (0.35 g, 75%).

12.4. Intramolecular Diels Alder Furan Reaction of 13a-b to 14a-b. The reaction scheme is as follows:

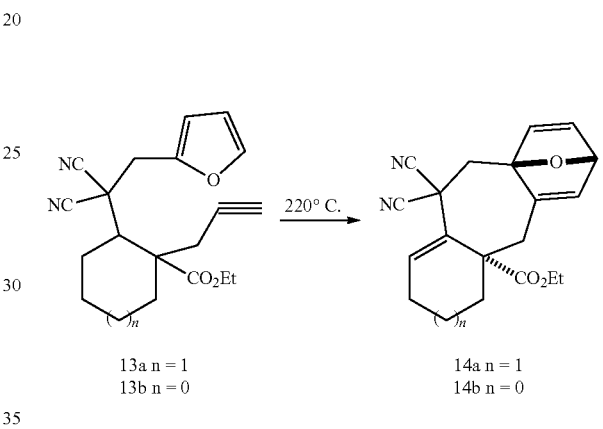

A 10-mL microwave tube equipped with a stir bar was charged with compound 13a or 13b (1 equiv.) and xylene (0.06 M). The tube was sealed with an aluminum cap and refilled with nitrogen. The reaction mixture was heated for 12 h at 220° C. After reaction, the solvent was removed in vacuo and the crude product was purified via column chromatography (hexanes-ethyl acetate 60:1) yielding respectively 14a as colorless oil (0.6 g, 64%, 2:1 dr) and 14b as pale yellow oil (0.015 g, 31%, 20:1 dr).

13. Protocols for diversification of scaffolds 6a, 6i, 6k, 6g, 16a.

13.1. Lactonization of 6a. The reaction scheme is as follows:

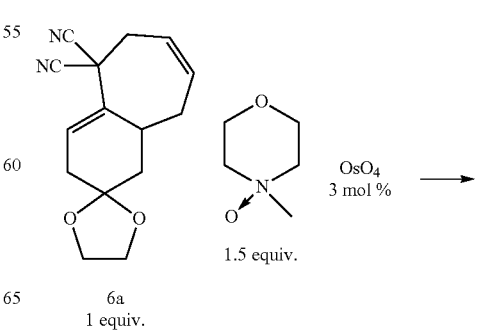

13.3. Hydrogenation of 6k. The reaction scheme is as follows:

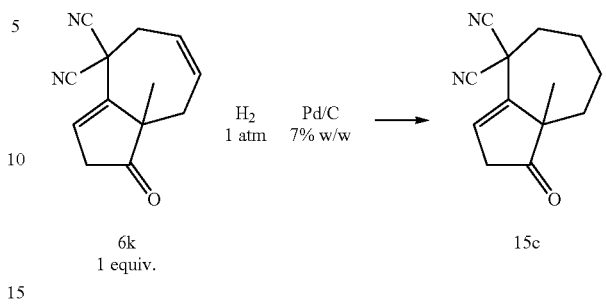

To a stirring mixture of compound 6k (50 mg, 0.24 mmol, 1 equiv.) in 2 mL dry THF, was added Pd/C (3.5 mg, 7% w/w). Then, $H_2$ was bubbled through the reaction mixture for 5 min using a balloon and a long needle. After 5 min, the needle was pulled out from the solution and left above the surface for 4 h at room temperature. The reaction was monitored by 1H NMR. After completion, the reaction mixture was filtered through a short pad of silica to remove particles of palladium. The pure product 15c was obtained as beige crystals without further purification (50 mg, quant. yield).

13.4. Reductive Decyanation of 6k. The reaction scheme is as follows:

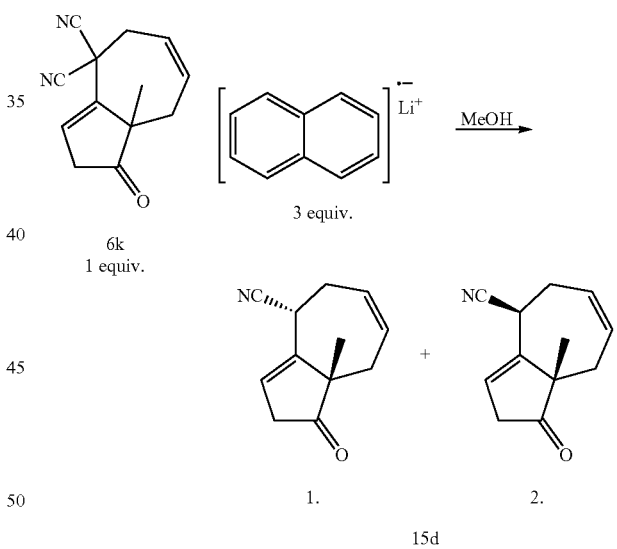

Lithium naphtalenide (LN) was prepared according to the previously reported procedure.[9] A solution of compound 6k (100 mg, 1.41 mmol, 1 equiv.) in 5 mL THF was cooled to −78° C. After 10 min, a solution of LN (1M in THF) was added dropwise (4.23 mmol, 3 equiv.) until a persistent olive-green color was observed for >20 sec. After 2 min. at −78° C., the reaction mixture was quenched with MeOH (2.5 mL) followed by a sat. $NH_4Cl$ solution in $H_2O$ (2.5 mL). The olive-green color disappeared instantly and the reaction mixture turned into a light orange-yellow color. The precipitate formed was filtered off and the EtOAc was used to rinse the sides of the flask. The mixture was then dried over $Na_2SO_4$ and the solvents were removed in vacuo. Final column chromatography (hexanes-ethyl acetate 10:1)

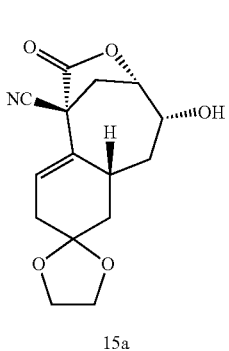

15a

To a stirred solution of N-methylmorpholine N-oxide (69 mg, 589 μmol, 1.5 equiv.) and (4 w/t % solution in THF, 75 μL, 3 mol %) was added the alkene substrate 6a (100 mg, 390 μmol, 1 equiv.) in a 4:1 mixture of acetone and $H_2O$ (2 mL) at r.t. After 2 hours, the reaction was quenched using 3 mL of a saturated solution of $Na_2SO_3$ and the resulting solution was allowed to stir overnight. Then, the reaction medium was transferred to a separatory funnel and extracted with 3×15 mL portions of diethyl ether. The combined phases were washed with 3 mL of a saturated solution of $Na_2SO_3$, $H_2O$, and brine; and dried over anhydrous $Na_2SO_4$. Concentration by rotary evaporation and purification by recrystallization using a mixture of EtOH/$H_2O$ with a ratio of 9:1 gave the product 15a (73 mg, 64%, dr>20:1).

13.2. Acetal deprotection of 6i. The reaction scheme is as follows:

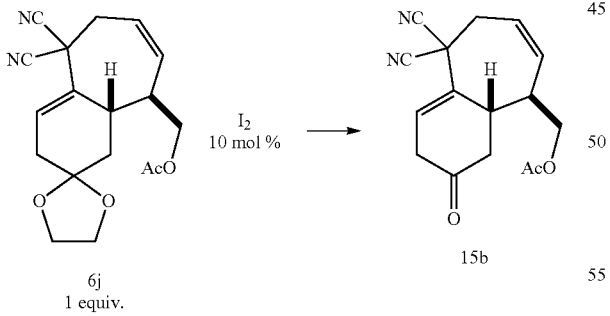

To a round bottom flask, protected ketone 6j (45 mg, 0.137 mmol, 1 equiv.) was dissolved in acetone (4 mL). Then, 10 mol % 12 was introduced. The mixture was then allowed to reflux overnight. Then the reaction medium was filtered through a short pad of silica gel eluted with a solvent mixture of ethyl acetate/hexanes 20% and concentrated in vacuo. The final product 15d was obtained as a light yellow oil (0.030 g, 77%).

afforded two separable diastereomers as beige solids in ~1:1 ratio (31.4 mg and 22.7 mg respectively, 61%).

13.5. NaH promoted Decyanation of 6k. The reaction scheme is as follows:

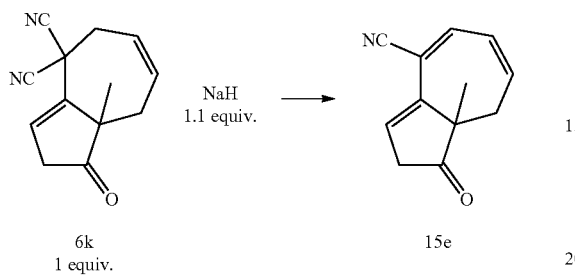

Compound 6k (20 mg, 0.094 mmol, 1 equiv.) was charged to a Schlenk flask under N₂ and DMF (1 mL) was added. At room temperature, NaH (3 mg, 0.104 mmol, 1.1 equiv.) in DMF (1 mL) was added dropwise to the previous mixture. The initial clear light brown solution turned instantly purple after NaH addition. The reaction mixture was then immediately quenched with 1M HCl in sat. NaCl solution. The purple solution turned to clear yellow. A volume of 2 mL of EtOAc was added and the aqueous mixture was extracted twice. The combined organic layers were washed with brine and finally dried over Na₂SO₄. The final compound 15e was obtained after column chromatography (hexanes-ethyl acetate 10:1) as a yellow solid (8 mg, 40%).

13.6. Ketone Reduction of 6k. The reaction scheme is as follows:

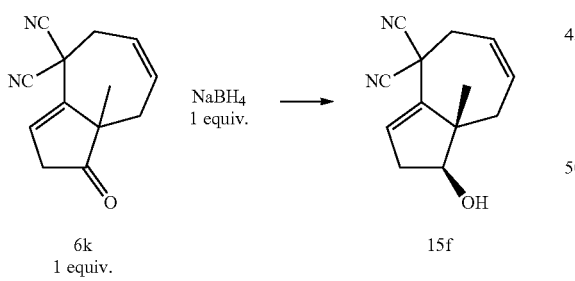

NaBH4 (3.5 mg, 0.094 mmol, 1 equiv.) was charged in a flame dried Schlenk flask under N₂ and dissolved in 1 mL ethanol at 0° C. Then, compound 6k (20 mg, 0.094 mmol, 1 equiv.) previously dissolved in 1 mL dry ethanol was added dropwise to the previous mixture at 0° C. After 10 min, the reaction mixture was quenched by H₂O (1 mL). The resulting solution was rotavapped and dried under high vacuum. The residue was finally purified via column chromatography (hexanes-ethyl acetate 3:1) yielding the title compound 15f as light-beige solid (13.5 mg, 66%, >20:1 dr).

13.7. Reductive Decyanation of 6g. The reaction scheme is as follows:

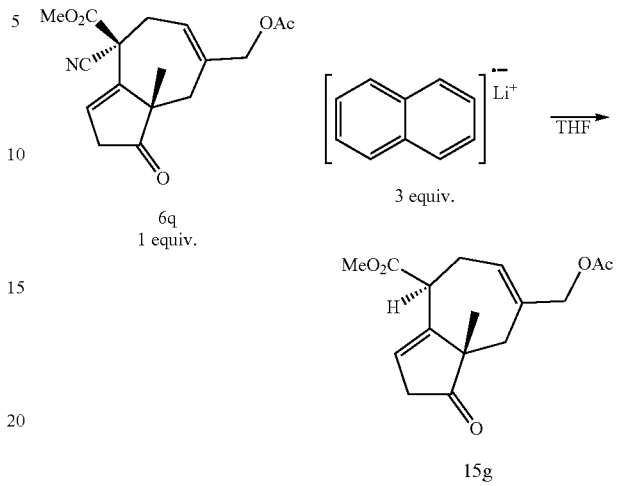

In a flame-dried schlenk flask, compound 6q (20 mg, 0.063 mmol, 1 equiv.) was dissolved in 2 mL dry THF and cooled down to −78° C. A 1 M lithium naphtalenide solution in THF (189 μL, 0.19 mmol, 3 equiv.) is slowly added at −78° C. until the green color remained for ~30 sec. The reaction mixture was then immediately quenched with a sat. NH₄Cl solution (2 mL). The resulting aqueous solution is extracted with EtOAc two times (5 mL). The combined organic layers were washed with brine (10 mL) and dried over Na₂SO₄. The solvents were removed under reduced pressure and the residue was purified via column chromatography (hexanes-ethyl acetate 5:1) yielding the final product as a colorless oil (7 mg, 40%).

13.8. Hydrolysis of 6g. The reaction scheme is as follows:

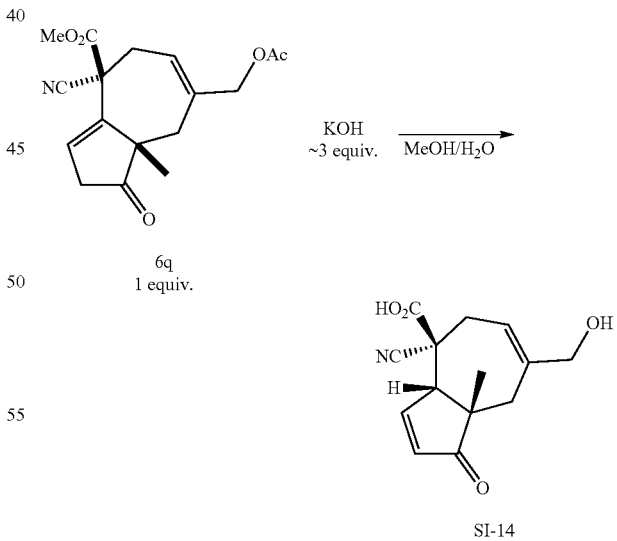

In a 10 mL round-bottom flask equipped with a stir bar, 6q (500 mg, 1.58 mmol, 1 equiv.) was charged and dissolved in MeOH (5 mL) at room temperature. Then, a 1 M aqueous solution of KOH was added (4.7 mL, 4.73 mmol, ~3 equiv.) still at room temperature. The initial clear colorless solution turned into a dark blue solution. After completion, 2 M aqueous HCl solution was added dropwise until pH reaches~1. The blue colored vanished and turned into a clear yellow. The reaction mixture was stirred for an additional 10 min. MeOH was then removed under reduced pressure and the resulting aqueous residue was extracted with EtOAc twice (2×5 mL). The combined organic layers were washed with brine and dried over $Na_2SO_4$. The final compound was obtained as a light yellow/white solid (317 mg, 77%) after purification via column chromatography (hexanes-ethyl acetate 1:1).

13.9. Decarboxylation of SI-14. The reaction scheme is as follows:

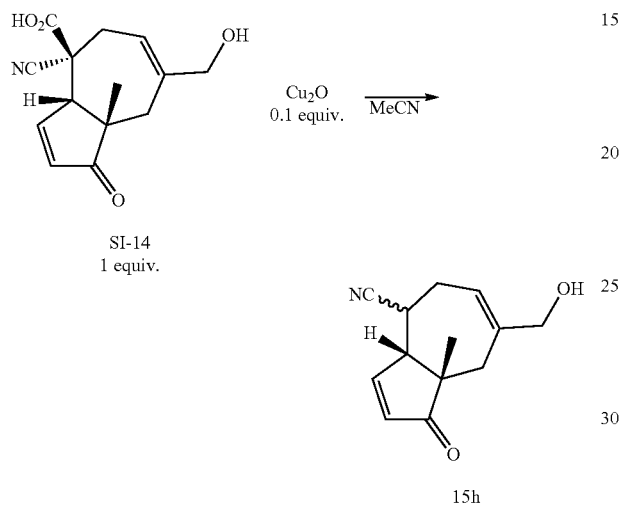

In a flame-dried schlenk flask, compound SI-14 (20 mg, 0.077 mmol, 1 equiv.) and $Cu_2O$ (1 mg, 0.0077 mmol, 10 mol %) were dissolved in 1.5 mL MeCN. The reaction mixture was refluxed at 80° C. After 1 h, the reaction mixture was cooled down to room temperature and pushed trough a short pad of silica gel. The final product was obtained as a mixture of diastereomers without further purification (15.4 mg, 1:1 d.r., 93%, orange solid).

13.10. Nitrile esterification by methanol. The reaction scheme is as follows:

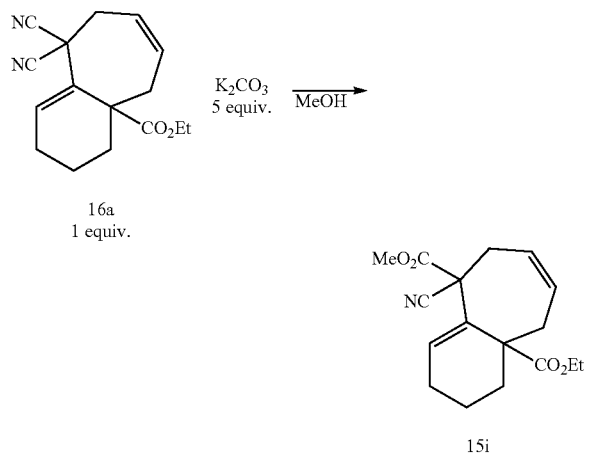

In a 2 mL vial equipped with a stir bar, compound 16a (26 mg, 0.096 mmol, 1 equiv.) was dissolved in MeOH (1 mL) and cooled down to 0° C. Then, $K_2CO_3$ (66 mg, 0.48 mmol, 5 equiv.) was added in one portion. The reaction mixture was allowed to reach room temperature over 2 h. Once the imidate intermediate was confirmed by TLC, the reaction mixture was cooled down to 0° C. and 2M HCl (1 mL) was added slowly until pH reaches ~1. After 50 min at room temperature, EtOAc (4 mL) was added and the reaction mixture was extracted two times. The resulting organic layers were combined, washed with brine (10 mL) and dried over $Na_2SO_4$. The solvents were concentrated down and the residue was purified via column chromatography (hexanes-ethyl acetate 10:1) yielding two separable diastereomers (27 mg, 10:1 d.r., 95%, major reported).

13.11. Nitrile esterification by allyl alcohol. The reaction scheme is as follows:

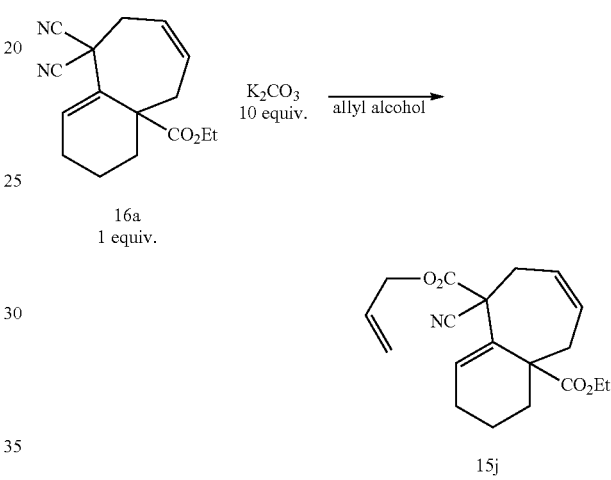

Substrate 16a (300 mg, 1.11 mmol, 1 equiv.) was dissolved in allyl alcohol (5 mL) and cooled down to 0° C. Ground $K_2CO_3$ (1.53 g, 11.10 mmol, 10 equiv.) was then added and the resulting mixture was stirred and allowed to warm up to room temperature. The imidate intermediate was monitored by TLC, and after 4 hours, 2M HCl (15 mL) was added slowly for hydrolysis. After 12 hours at room temperature, EtOAc (15 mL) was added and the reaction mixture was extracted three times with the same volume of solvent. The resulting organic layers were combined, washed with brine (10 mL) and dried over $Na_2SO_4$. The solvents were concentrated down and the residue was purified via column chromatography (ethyl acetate 7% in hexanes) yielding two separable diastereomers (165.6 mg, 4:1 d.r., 45

13.12. Amide formation from 16a. The reaction scheme is as follows:

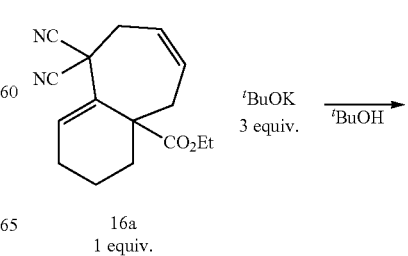

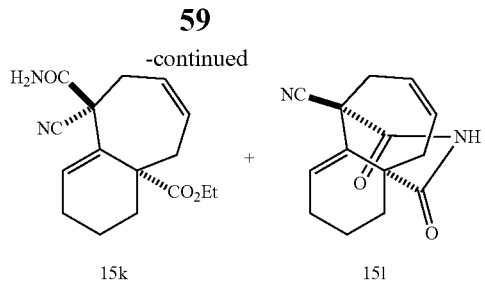

15k         15l

In a flame-dried schlenk flask, 16a (20 mg, 0.074 mmol, 1 equiv.) and fresh tBuOK (25 mg, 0.22 mmol, 3 equiv.) were charged under $N_2$. 2 mL $^t$BuOH was added and the reaction mixture was stirred at room temperature. After 30 min, completion was observed by TLC and the reaction mixture was quenched with $H_2O$ (2 mL) and extracted with EtOAc (4 mL). The organic layer was washed with brine (10 mL) and dried over $Na_2SO_4$. The solvents were removed under reduced pressure and the final products were isolated by column chromatography (hexanes-ethyl acetate 5:1) as white solids (13 mg, 1.5:1 d.r., 66%) respectively product 15k (8 mg, 38%) and 15l (5 mg, 28%).

2-(1,4-dioxaspiro[4.5]decan-8-ylidene)malononitrile (1a). Prepared by general procedure C with the following notes: Conditions: overnight, reflux (bath temperature=130° C.) White crystals, 23.19 g, 88%. $^1$H NMR (500 MHz, CDCl$_3$): δ 4.00 (4H, s), 2.85 (4H, d, J=6.4 Hz), 1.88 (4H, t, J=6.4 Hz) $^{13}$C NMR (126 MHz, CDCl$_3$): δ 182.1, 111.6, 106.4, 84.0, 65.0, 34.7, 31.7. HRMS (ESI-TOF) m/z: Calcd for $C_{11}H_{11}N_2O_2$ [M–H]$^-$ 203.0828 Found 203.0828.

2-(2-oxocyclohexylidene)malononitrile (1b). Prepared from 1,4-dioxaspiro[4.5]decan-6-one[21] by general procedure C with the following notes: Conditions: overnight, reflux (bath temperature=130° C.) Yellow oil, 770 mg, 55%. $^1$H NMR (Chloroform-d, 500 MHz) δ 4.15-3.64 (5H, m), 2.84-2.73 (1H, m), 1.94-1.66 (4H, m), 1.60-1.49 2H, m). $^{13}$C NMR (cdcl3, 126 MHz) δ 179.9, 112.2, 111.6, 106.9, 82.7, 65.3, 38.2, 34.2, 31.2, 22.7, 22.2. HRMS (ESI-TOF) m/z: Calcd for C11H12N2NaO2 [M+Na]$^+$227.0791; Found 227.0784. Note: contaminated with 50% of diprotected 1,2-cyclohexanedione, having the same Rf. Used as it is for the next step and was able to purify after Cope rearrangement.

2-(2,2-dimethyl-3-oxocyclohexylidene)malononitrile (1c). Prepared by general procedure C with the following notes: conditions: overnight, reflux (bath temperature=130° C.). $^1$H NMR (500 MHz, CDCl$_3$): δ 2.91 (t, J=6.6 Hz, 2H), 2.63 (t, J=7.3 Hz, 2H), 2.09-2.02 (m, 2H), 1.59 (s, 6H). $^{13}$C NMR (126 MHz, CDCl$_3$): δ 208.28, 186.01, 112.39, 112.12, 85.03, 53.27, 35.91, 33.46, 23.93, 19.56. HRMS (ESI-TOF) m/z: Calcd for $C_{14}H_{15}N_2O$ [M–H]$^-$ 227.1190; Found 227.1199.

2-cycloheptylidenemalononitrile (1d). Prepared by general procedure C with the following notes: Conditions: overnight, reflux (bath temperature=130° C.) Yellow oil, 5.47 g, 96%. $^1$H NMR (500 MHz, CDCl$_3$): δ 2.80 (2H, t, J=6.0 Hz), 1.86-1.67 (2H, m), 1.59 (2H, dt, J=6.0, 2.7 Hz). $^{13}$C NMR (126 MHz, CDCl$_3$): δ 188.6, 112.0, 85.0, 36.4, 29.1, 26.2. HRMS (ESI-TOF) m/z: Calcd for $C_{10}H_{11}N_2$ [M–H]$^-$ 159.0928; Found 159.0935.

2-(tetrahydro-4H-pyran-4-ylidene)malononitrile (1e). Prepared by general procedure C with the following notes: Conditions: overnight, reflux (bath temperature=130° C.) Brown-red crystals, 1.98 g, 67%. $^1$H NMR (500 MHz, CDCl$_3$): δ 3.86 (4H, t, J=5.5 Hz), 2.79 (4H, t, J=5.5 Hz). $^{13}$C NMR (126 MHz, CDCl$_3$): δ 178.5, 111.0, 84.0, 67.7, 35.0. HRMS (ESI-TOF) m/z: Calcd for $C_8H_7N_{20}$ [M–H]$^-$ 149.0678; Found 149.0716.

2-(3,4-dihydronaphthalen-1(2H)-ylidene)malononitrile (1f). Conditions: overnight, reflux (bath temperature=130° C.) Light green crystals, 1.90 g, 71%. Analytical data are identical to those in the reference.[17]

2-cyclohexylidenemalononitrile (1g). Prepared by general procedure C with the following notes: Conditions: overnight, reflux (bath temperature=130° C.) Colorless oil, 5 g, 80%. Analytical data are identical to those in the reference.[18]

allyl acetate (2a). Prepared by general procedure B with the following notes: Column chromatography (hexanes-ethyl acetate 20:1) affords the titled compound as a colorless oil (20g, 91%). Analytical data are identical to those in the reference.[14]

allyl tert-butyl carbonate (2b) Prepared by general procedure A with the following notes: Vacuum distillation (90-100° C., 1 torr) affords the title compound as a colorless oil (16 g, 90%). Analytical data are identical to those in the reference.[10]

tert-butyl (2-methylallyl) carbonate (2c). Prepared by general procedure A with the following notes: Vacuum distillation (105-110° C., 1 torr) affords the titled compound as a colorless oil (15 g, 95%). Analytical data are identical to those in the reference.[11]

2-methylenepropane-1,3-diyl diacetate (2d). Prepared by general procedure B with the following notes: Column chromatography (hexanes-ethyl acetate 20:1) affords the titled compound as a pale yellow oil (23 g, 98%). Analytical data are identical to those in the reference.[15]

di-tert-butyl (2-methylenepropane-1,3-diyl) bis(carbonate) (2e). Prepared by general procedure A with the following notes: Column chromatography (hexanes-ethyl acetate 10:1) affords the titled compound as white crystals (11 g, 98%). Analytical data are identical to those in the reference.[12]

di-tert-butyl (2-methylenepropane-1,3-diyl) bis(carbonate) (2f). Prepared by general procedure A with the following notes: Column chromatography (hexanes-ethyl acetate 20:1) affords the titled compound as a colorless oil (20 g, 89%). Analytical data are identical to those in the reference.[13]

(Z)-but-2-ene-1,4-diyl diacetate (2g). Prepared by general procedure B with the following notes: Column chromatography (hexanes-ethyl acetate 20:1) affords the titled compound as yellow oil (19 g, 83%). Analytical data are identical to those in the reference.[16]

2-allyl-2-(1,4-dioxaspiro[4.5]dec-7-en-8-yl)malononitrile (3a). Prepared from 1a by general procedure D with the following notes: Conditions: DCM, room temperature, 30 min, electrophile 2b Clear colorless oil, 0.080 g, 82%. $^1$H NMR (500 MHz, CDCl$_3$): δ 6.11 (1H, t, J=3.6 Hz), 5.81 (1H, ddt, J=17.3, 10.2, 7.2 Hz), 5.47-5.33 (2H, m), 3.98 (4H, s), 2.78 (2H, d, J=7.2 Hz), 2.45-2.33 (4H, m), 1.85 (2H, t, J=6.4 Hz). $^{13}$C NMR (126 MHz, CDCl$_3$): δ 128.4, 127.3, 127.2, 123.1, 114.0, 106.5, 64.6, 43.3, 41.5, 35.8, 30.8, 24.0.

HRMS (ESI-TOF) m/z: Calcd for $C_{14}H_{16}N_2NaO_2$ [M+Na]$^+$267.1104; Found 267.1094.

2-allyl-2-(1,4-dioxaspiro[4.5]dec-6-en-6-yl)malononitrile (3b). Prepared from 1b by general procedure D with the following notes: Conditions: DCM, room temperature, 20 min, electrophile 2b Colorless oil, 0.225 g, 75%. Determined from NMR spectrum. $^1$H NMR (Chloroform-d, 500 MHz) δ $^1$H NMR (Chloroform-d, 500 MHz) δ 6.38 (1H, t, J=3.9 Hz), 5.88 (1H, ddt, J=17.4, 10.2, 7.4 Hz), 5.46-5.26 (2H, m), 4.29-4.14 (2H, m), 4.08-4.01 (2H, m), 3.02-2.84

(2H, m), 2.22 (2H, td, J=5.9, 3.7 Hz), 1.83-1.69 (4H, m). $^{13}$C NMR (cdcl3, 126 MHz) δ 137.1, 129.5, 129.1, 122.7, 114.7, 105.9, 64.0, 44.6, 39.0, 32.8, 25.5, 19.4. HRMS (ESI-TOF) m/z: Calcd for $C_{17}H_{21}N_2O_2$ [M+H]$^+$ 285.1598; Found 285.1596. Note: contaminated with 50% of diprotected 1,2-cyclohexanedione, having the same Rf. Used as it is for the next step and was able to purify after Cope rearrangement.

2-allyl-2-(6,6-dimethyl-5-oxocyclohex-1-en-1-yl)malononitrile (3c). Prepared from 1c by general procedure D with the following notes: Conditions: DCM, room temperature, 1 h, electrophile 2b Brown-orange oil, 0.345 g. $^1$H NMR (Chloroform-d, 500 MHz) δ 6.41-6.31 (1H, m), 5.96-5.82 (1H, m), 5.50-5.35 (2H, m), 2.92-2.85 (2H, m), 2.61-2.52 (4H, m), 1.53 (6H, s). $^{13}$C NMR (cdcl3, 126 MHz) δ 210.2, 135.4, 130.8, 128.5, 123.6, 115.1, 48.1, 44.8, 40.2, 33.9, 24.3, 23.9. HRMS (ESI-TOF) m/z: Calcd for $C_{14}H_{15}N_2O$ [M−H]$^-$ 227.1190; Found 227.1197. Note: contaminated with up to 20% of E-adduct. Used as it is for the next step and was able to purify after Cope rearrangement.

2-allyl-2-(cyclohept-1-en-1-yl)malononitrile (3d). Prepared from 5b by general procedure D with the following notes: Conditions: DCM, room temperature, 30 min, electrophile 2b Clear colorless oil, 0.471 g, 76%. Analytical data are identical to those in the reference.[19]

2-allyl-2-(3,6-dihydro-2H-pyran-4-yl)malononitrile (3e). Prepared from 1e by general procedure D with the following notes: Conditions: DCM, room temperature, 30 min, electrophile 2b Clear colorless oil, 0.080 g, 63%. $^1$H NMR (500 MHz, CDCl$_3$): δ 6.33-6.17 (1H, m), 5.82 (1H, dddd, J=17.9, 10.0, 7.5, 6.7 Hz), 5.48-5.33 (2H, m), 4.31-4.20 (2H, m), 3.86 (2H, td, J=5.2, 0.8 Hz), 2.78 (2H, ddd, J=6.5, 1.6, 0.8 Hz), 2.36-2.17 (2H, m) 13C NMR (126 MHz, CDCl$_3$): δ 128.2, 128.1, 125.8, 123.3, 113.6, 65.0, 63.4, 43.1, 41.0, 24.5.

HRMS (ESI-TOF) m/z: Calcd for $C_{11}H_{11}N_2O$ [M−H]$^-$ 187.0871; Found 187.0865.

2-allyl-2-(3,4-dihydronaphthalen-1-yl)malononitrile (3f). Prepared from 5c by general procedure D with the following notes: Conditions: DCM, room temperature, 30 min, electrophile 2b Brown-orange oil, 0.583 g, 95%. (no purification required). $^1$H NMR (500 MHz, CDCl$_3$): δ 7.68-7.61 (1H, m), 7.32-7.18 (3H, m), 6.67 (1H, t, J=4.9 Hz), 5.87 (1H, dddt, J=17.0, 10.2, 7.3 Hz), 5.40 (1H, dq, J=10.2, 1.0 Hz), 5.32 (1H, dq, J=16.9, 1.2 Hz), 3.06 (2H, d, J=7.2 Hz), 2.75 (2H, t, J=7.9 Hz), 2.40 (2H, ddd, J=9.2, 7.2, 4.9 Hz). $^{13}$C NMR (126 MHz, CDCl$_3$): δ 137.3, 132.6, 129.2, 128.5, 128.5, 128.4, 127.6, 126.6, 123.2, 123.2, 114.7, 41.3, 41.0, 27.6, 23.3. HRMS (ESI-TOF) m/z: Calcd for $C_{16}H_{14}N_2Na$ [M+Na]$^+$ 257.1049; Found 257.0980.

4,4-dicyano-2-methylene-4-(1,4-dioxaspiro[4.5]dec-7-en-8-yl)butyl acetate (3g). Prepared from 1g by general procedure D with the following notes: Conditions: DCM, room temperature, 20 min, electrophile 2c Colorless oil, 1.62 g, 64%. $^1$H NMR (500 MHz, CDCl$_3$): δ 6.24-6.04 (1H, m), 5.18-5.11 (1H, m), 5.09-5.04 (1H, m), 3.98 (4H, s), 2.72 (2H, s), 2.48-2.31 (4H, m), 1.91 (3H, s), 1.84 (2H, t, J=6.3 Hz). $^{13}$C NMR (126 MHz, CDCl$_3$): δ 137.1, 128.0, 127.0, 118.9, 114.4, 106.5, 64.6, 44.9, 42.9, 35.9, 30.8, 24.1, 23.1. HRMS (ESI-TOF) m/z: Calcd for $C_{15}H_{19}N_2O_2$ [M+H]$^+$ 259.1441; Found 259.1451.

4,4-dicyano-2-methylene-4-(1,4-dioxaspiro[4.5]dec-7-en-8-yl)butyl acetate (3h). Prepared from 1a by general procedure D with the following notes: Conditions: DCM, room temperature, 2 h, base: K$_2$CO$_3$, electrophile 2d White solid, 1.02 g, 66%. $^1$H NMR (500 MHz, CDCl$_3$): δ 5.24 (1H, s), 5.02 (1H, s), 4.63-4.48 (2H, m), 4.06-3.87 (4H, m), 3.36 (1H, dd, J=16.4, 7.0 Hz), 3.04-2.92 (1H, m), 2.79 (1H, td, J=14.4, 5.2 Hz), 2.64 (1H, dd, J=13.9, 8.9 Hz), 2.40 (1H, dd, J=13.9, 7.0 Hz), 2.15-2.07 (3H, m), 2.07-1.93 (2H, m), 1.86 (1H, dd, J=14.2, 6.2 Hz), 1.73 (1H, td, J=13.8, 4.4 Hz). $^{13}$C NMR (126 MHz, CDCl$_3$): δ 184.4, 170.6, 139.9, 117.5, 111.5, 111.3, 106.4, 84.6, 66.1, 65.0, 64.3, 40.5, 37.3, 36.5, 35.1, 28.7, 20.9. HRMS (ESI-TOF) m/z: Calcd for $C_{17}H_{20}N_2NaO_4$ [M+Na]$^+$339.1496; Found 339.1314.

(E)-2-(cyclohex-1-en-1-yl)-2-(hex-2-en-1-yl)malononitrile (3i). Prepared from 1g by general procedure D with the following notes: Conditions: THF, 50° C., 3 h, electrophile 2f Clear oil, 0.4 g, 84%, $^1$H NMR (500 MHz, CDCl$_3$): δ 6.15 (q, J=3.7 Hz, 1H), 5.73 (dtd, J=14.2, 7.0, 3.5 Hz, 1H), 5.39 (ddt, J=18.8, 9.0, 5.5 Hz, 1H), 2.65 (dq, J=7.4, 3.6 Hz, 2H), 2.16-1.97 (m, 7H), 1.69 (qd, J=5.9, 3.0 Hz, 2H), 1.57 (dtt, J=9.4, 6.1, 3.2 Hz, 2H), 1.45-1.32 (m, 3H), 0.87 (tq, J=7.4, 3.5 Hz, 3H). Note: contaminated with up to 9% of Q-adduct. Used as it is for the next step and was able to purify after the second allylation.

(E)-5,5-dicyano-5-(1,4-dioxaspiro[4.5]dec-7-en-8-yl) pent-2-en-1-yl acetate (3j). Prepared from 1a by general procedure D with the following notes: Conditions: THF, 50° C., 3 h, electrophile 2g Light yellow oil, 30 g, 70%. $^1$H NMR (500 MHz, CDCl$_3$): δ 6.13-6.00 (m, 1H), 5.86 (dt, J=15.5, 5.6 Hz, 1H), 5.77-5.57 (m, 1H), 4.58-4.50 (m, 2H), 3.93 (s, 4H), 2.74 (d, J=7.2 Hz, 2H), 2.33 (dp, J=8.5, 2.1 Hz, 4H), 2.03 (s, 3H), 1.80 (t, J=6.3 Hz, 2H). $^{13}$C NMR (126 MHz, CDCl$_3$): δ 170.39, 132.62, 127.49, 126.99, 123.84, 113.89, 106.40, 64.49, 63.53, 43.12, 40.00, 35.70, 30.63, 23.94, 20.76. HRMS (ESI-TOF) m/z: Calcd for $C_{17}H_{21}N_2O_4$ [M+H]$^+$ 316.36; Found 317.1496.

2-(7-allyl-1,4-dioxaspiro[4.5]decan-8-ylidene)malononitrile (4a). Prepared from 3a by general procedure E with the following notes: Conditions: 55 min Colorless oil, 0.092 g, 76%. Conditions for large scale: Crude 3a was transferred to a 250 mL ace round-bottom pressure flask and diluted in 100 mL of toluene. The round bottom flask was then tightly closed, set in a silicon oil bath and the resulting medium was heated up to 170° C. for 2 hours. The reaction mixture was concentrated by rotary evaporation and purification by column chromatography afforded the γ-allylated product in quantitative yield. $^1$H NMR (500 MHz, CDCl$_3$): δ 5.70 (1H, ddt, J=16.9, 10.1, 7.7, 6.8 Hz), 5.13 (1H, ddt, J=10.1, 1.8, 1.0 Hz), 5.08 (1H, ddt, J=17.2, 3.3, 1.5 Hz), 4.10-3.82 (4H, m), 3.30-3.18 (1H, m), 2.96 (1H, dddd, J=14.7, 4.5, 2.7, 1.7 Hz), 2.73 (1H, td, J=14.4, 5.2 Hz), 2.62-2.42 (2H, m), 2.14-1.92 (2H, m), 1.87 (1H, dd, J=14.0, 6.2 Hz), 1.73 (1H, td, J=13.7, 4.4 Hz). $^{13}$C NMR (126 MHz, CDCl$_3$): δ 184.6, 134.4, 118.7, 111.5, 106.5, 65.0, 64.3, 42.2, 38.5, 37.2, 35.2, 29.7, 28.7.

HRMS (ESI-TOF) m/z: Calcd for $C_{14}H_{15}N_2O_2$ [M−H]$^-$ 243.1139; Found 243.114.

2-(7-allyl-1,4-dioxaspiro[4.5]decan-6-ylidene)malononitrile (4b). Prepared from 3b by general procedure E with the following notes: Condition: 3 h Clear yellow oil, 0.100 g, 50%. $^1$H NMR (Chloroform-d, 500 MHz) δ 5.73 (1H, ddt, J=17.1, 10.1, 7.3 Hz), 5.16-5.02 (2H, m), 4.30-4.21 (1H, m), 4.14-4.05 (1H, m), 4.02-3.90 (1H, m), 3.83-3.70 (1H, m), 3.38-3.25 (1H, m), 2.60 (1H, ddd, J=13.8, 8.8, 7.4 Hz), 2.47-2.34 (1H, m), 2.04-1.82 (3H, m), 1.82-1.75 (1H, m), 1.74-1.57 (2H, m). $^{13}$C NMR (cdcl3, 126 MHz) δ 180.1, 134.9, 118.3, 112.5, 111.8, 106.4, 85.5, 65.5, 65.3, 44.1, 38.0, 37.7, 30.0, 18.2. HRMS (ESI-TOF) m/z: Calcd for $C_{14}H_{17}N_2O_2$ [M+H]$^+$ 245.1285; Found 245.1285.

2-((8-(dicyanomethylene)-1,4-dioxaspiro[4.5]decan-7-yl) methyl)allyl acetate (4c). Prepared from 1c by general procedure E with the following notes: Conditions: 30 min clear yellow oil, 0.110 g, 55%. $^1$H NMR (500 MHz, CDCl$_3$): δ 5.73 (1H, ddt, J=17.1, 10.2, 7.1 Hz), 5.18 (1H, dd, J=9.9, 1.5 Hz), 5.10 (1H, dt, J=16.9, 1.5 Hz), 3.40 (1H, tt, J=7.5, 3.3 Hz), 2.70-2.52 (2H, m), 2.25-2.09 (4H, m), 1.59 (6H, d, J=10.5 Hz). $^{13}$C NMR (126 MHz, CDCl$_3$): δ 208.6, 189.3, 132.7, 119.5, 112.1, 112.0, 85.8, 50.3, 42.5, 35.5, 31.0, 25.5, 22.1, 22.0. HRMS (ESI-TOF) m/z: Calcd for C$_{14}$H$_{15}$N$_2$O [M–H]$^-$ 227.1190; Found 227.1199.

2-(2-allylcycloheptylidene)malononitrile (4d). Prepared from 3d by general procedure E with the following notes: Conditions: 35 min Colorless oil, 0.067 g, 67%. $^1$H NMR (500 MHz, CDCl$_3$): β 5.73 (1H, ddt, J=17.1, 10.1, 7.4 Hz), 5.10 (1H, dd, J=10.1, 1.6 Hz), 5.04 (1H, dq, J=17.1, 10.1, 7.4 Hz), 5.10 (1H, dd, J=10.1, 1.6 Hz), 5.04 (1H, dq, J=17.1, 1.6 Hz), 3.15 (1H, dq, J=10.4, 6.8 Hz), 2.88 (1H, ddd, J=12.3, 6.4, 1.9 Hz), 2.37-2.24 (2H, m), 2.15 (2H, dt, J=14.5, 7.4 Hz), 2.08 (1H, td, J=6.2, 1.8 Hz), 1.92-1.77 (2H, m), 1.36 (3H, dt, J=14.5, 10.4 Hz), 1.08-0.95 (1H, m). $^{13}$C NMR (126 MHz, CDCl$_3$): δ 190.8, 133.6, 118.5, 112.0, 111.8, 86.3, 46.8, 46.8, 40.4, 32.6, 31.1, 30.2, 29.1, 25.5. HRMS (ESI-TOF) m/z: Calcd for C$_{13}$H$_{15}$N$_2$ [M–H]$^-$ 199.1241; Found 199.1237.

2-(3-allyltetrahydro-4H-pyran-4-ylidene)malononitrile (4e). Prepared from 3e by general procedure E with the following notes: Conditions: 35 min Clear colorless oil, 0.423 g, 85%. $^1$H NMR (500 MHz, CDCl$_3$): δ 5.89-5.56 (1H, m), 5.26-5.05 (2H, m), 4.24 (1H, dd, J=11.3, 6.2 Hz), 4.05 (1H, dd, J=11.7, 1.4 Hz), 3.63-3.30 (2H, m), 3.01 (1H, d, J=7.8 Hz), 2.89-2.78 (1H, m), 2.78-2.64 (1H, m), 2.64-2.40 (2H, m). $^{13}$C NMR (126 MHz, CDCl$_3$): δ 181.1, 133.2, 119.1, 111.1, 84.4, 70.4, 67.8, 43.7, 36.3, 31.8. Note: overlapping nitrile groups at 111.1 ppm. HRMS (ESI-TOF) m/z: Calcd for C$_{11}$H$_{11}$N$_2$O [M–H]$^-$ 187.0878; Found 187.0877.

2-(2-allyl-3,4-dihydronaphthalen-1(2H)-ylidene)malononitrile (4f). Prepared from 3f by general procedure E with the following notes: Conditions: 1 h Clear colorless oil, 0.701 g, 99%, no purification. $^1$H NMR (500 MHz, CDCl$_3$): δ 8.04 (1H, dt, J=8.2, 1.9 Hz), 7.52 (1H, td, J=7.5, 1.3 Hz), 7.41-7.32 (1H, m), 7.32-7.25 (1H, m), 5.77 (1H, ddt, J=17.1, 10.1, 7.2 Hz), 5.11 (1H, dd, J=10.1, 1.7 Hz), 4.98 (1H, dd, J=17.1, 1.7 Hz), 3.46 (1H, tt, J=7.5, 4.6 Hz), 3.00 (1H, ddd, J=16.3, 10.0, 5.9 Hz), 2.88 (1H, ddd, J=17.6, 6.5, 4.2 Hz), 2.33-2.22 (2H, m), 2.17 (1H, dddd, J=14.3, 10.0, 6.5, 4.6 Hz), 2.01 (1H, ddt, J=14.3, 5.9, 4.2 Hz). $^{13}$C NMR (126 MHz, CDCl$_3$): δ 176.9, 134.0, 133.6, 129.5, 129.3, 128.4, 127.0, 118.4, 113.9, 113.5, 80.4, 77.4, 77.2, 76.9, 41.8, 36.9, 26.5, 25.4. HRMS (ESI-TOF) m/z: Calcd for C$_{16}$H$_{13}$N$_2$ [M–H]$^-$ 234.1157; Found 234.1154.

2-((8-(dicyanomethylene)-1,4-dioxaspiro[4.5]decan-7-yl)methyl)allyl acetate (4g). Prepared from 3g by general procedure E with the following notes: Conditions: 30 min Yellow oil, 0.701 g, 70%. $^1$H NMR (500 MHz, CDCl$_3$): δ 4.95-4.84 (1H, m), 4.76-4.66 (1H, m), 4.08-3.85 (4H, m), 3.32 (1H, dd, J=15.6, 6.7 Hz), 3.01-2.90 (1H, m), 2.77 (1H, dd, J=14.5, 5.2 Hz), 2.61-2.50 (1H, m), 2.31 (1H, dd, J=13.2, 6.9 Hz), 2.08-1.92 (2H, m), 1.82 (1H, dd, J=14.3, 6.2 Hz), 1.78-1.68 (4H, m). $^{13}$C NMR (126 MHz, CDCl$_3$): δ 185.4, 141.5, 114.8, 111.5, 111.4, 106.5, 84.1, 64.9, 64.3, 42.2, 40.3, 36.4, 35.2, 28.7, 21.8.

HRMS (ESI-TOF) m/z: Calcd for C$_{15}$H$_{18}$N$_2$NaO$_2$ [M+Na]$^+$258.1260 Found 281.1269.

2-((8-(dicyanomethylene)-1,4-dioxaspiro[4.5]decan-7-yl)methyl)allyl acetate (4h). Prepared from 3 h by general procedure E with the following notes: Conditions: 30 min Clear yellow oil, 0.359 g, 72%. $^1$H NMR (500 MHz, CDCl$_3$): δ 5.24 (1H, s), 5.02 (1H, s), 4.63-4.47 (2H, m), 4.06-3.87 (4H, m), 3.36 (1H, dd, J=15.7, 7.1 Hz), 2.99 (1H, dt, J=15.6, 2.8 Hz), 2.79 (1H, td, J=14.4, 5.2 Hz), 2.64 (1H, dd, J=13.8, 8.9 Hz), 2.40 (1H, dd, J=13.8, 7.0 Hz), 2.10 (3H, s), 2.07-1.94 (2H, m), 1.86 (1H, dd, J=14.2, 6.2 Hz), 1.73 (1H, td, J=13.8, 4.4 Hz). $^{13}$C NMR (126 MHz, CDCl$_3$): δ 184.4, 170.6, 139.9, 117.5, 111.5, 111.3, 106.4, 84.6, 66.1, 65.0, 64.3, 40.5, 37.3, 36.5, 35.1, 28.7, 20.9. HRMS (ESI-TOF) m/z: Calcd for C$_{17}$H$_{20}$N$_2$NaO$_4$ [M+Na]$^+$339.1315; Found 339.1316.

2-((S)-2-((R)-hex-1-en-3-yl)cyclohexylidene)malononitrile (4i). Prepared from 3l by general procedure E with the following notes: Conditions: 170° C., 1 h. Clear oil, 0.070 g, 74%. $^1$H NMR (500 MHz, CDCl$_3$): δ 5.39 (dt, J=17.0, 10.0 Hz, 1H), 5.02 (d, J=10.1 Hz, 1H), 4.91 (d, J=17.0 Hz, 1H), 2.87 (dq, J=13.1, 4.0, 3.4 Hz, 2H), 2.30 (dtt, J=33.1, 13.8, 6.3 Hz, 2H), 2.15 (dt, J=13.9, 2.6 Hz, 1H), 2.07 (ddd, J=13.3, 5.7, 2.8 Hz, 1H), 1.62 (dddd, J=14.4, 11.5, 8.4, 3.9 Hz, 3H), 1.57-1.32 (m, 3H), 1.27-1.13 (m, 2H), 0.90 (t, J=7.2 Hz, 3H). $^{13}$C NMR (126 MHz, CDCl$_3$): δ 188.09, 138.42, 116.77, 112.08, 111.90, 83.38, 47.21, 45.00, 34.21, 31.70, 29.10, 28.23, 20.00, 19.89, 14.02. HRMS (ESI-TOF) m/z: Calcd for C$_{15}$H$_{20}$N$_2$Na [M+Na]$^+$228.34; Found 251.1519. Note: contaminated with up to 8% of impurities. Used as it is for the next step and was able to purify after the second allylation. Stereochemistry was assigned based on 4j.

(R)-2-((S)-8-(dicyanomethylene)-1,4-dioxaspiro[4.5]decan-7-yl)but-3-en-1-yl acetate (4j). Prepared from 3j by general procedure E with the following notes: Conditions: 170° C., 1 h. Light yellow oil, 27 g, 99%. $^1$H NMR (500 MHz, CDCl$_3$): δ 5.64 (dt, J=17.0, 10.1 Hz, 1H), 5.17-4.99 (m, 2H), 4.29 (dd, J=11.2, 5.0 Hz, 1H), 4.19 (dd, J=11.2, 3.0 Hz, 1H), 4.10-3.90 (m, 4H), 3.22 (dd, J=11.0, 5.7 Hz, 1H), 3.16-3.02 (m, 1H), 2.92 (ddt, J=14.6, 4.5, 2.2 Hz, 1H), 2.59 (td, J=14.3, 5.3 Hz, 1H), 2.11 (dt, J=14.9, 2.3 Hz, 1H), 2.08 (s, 3H), 2.07-2.00 (m, 1H), 1.83 (dd, J=14.7, 5.8 Hz, 1H), 1.72 (td, J=13.9, 4.5 Hz, 1H). $^{13}$C NMR (126 MHz, CDCl$_3$): δ 183.45, 171.11, 135.71, 118.68, 111.63, 111.51, 106.51, 85.63, 65.31, 64.99, 64.54, 45.18, 42.80, 35.72, 35.57, 29.12, 20.96. HRMS (ESI-TOF) m/z: Calcd for C$_{17}$H$_{20}$N$_2$NaO$_4$ [M+Na]$^+$316.36; Found 339.1351. Note: Stereochemistry was assigned based on 6j.

2-(2-allyl-2-methyl-3-oxocyclopentylidene)malononitrile (4k). Prepared from allylated 7a by general procedure C with the following notes: Conditions: overnight, reflux (bath temperature=130° C.). Brown oil, 0.756 g, 57%. Large scale: 9.5 g was prepared by the same procedure. $^1$H NMR (500 MHz, CDCl$_3$): δ 5.47 (ddt, J=15.2, 10.2, 7.6 Hz, 1H), 5.19-5.12 (m, 2H), 3.21 (ddd, J=20.7, 10.6, 6.4 Hz, 1H), 3.03 (ddd, J=20.8, 11.0, 7.2 Hz, 1H), 2.76 (dd, J=13.8, 8.0 Hz, 1H), 2.69-2.59 (m, 2H), 2.54 (ddd, J=19.5, 11.0, 6.3 Hz, 1H), 1.46 (s, 3H). $^{13}$C NMR (126 MHz, CDCl$_3$): δ 215.03, 189.08, 130.83, 121.03, 111.24, 110.71, 85.09, 57.25, 41.66, 34.96, 30.19, 21.56. HRMS (ESI-TOF) m/z: Calcd for C$_{12}$H$_{11}$N$_2$O [M–H]$^-$ 199.0877; Found 199.0885.

2-(2-allyl-2-methyl-3-oxocyclohexylidene)malononitrile (4l). Prepared from allylated 7b by general procedure C with the following notes: Conditions: overnight, reflux (bath temperature=130° C.). Yellow-orange oil, 0.839 g, 47%. $^1$H NMR (500 MHz, CDCl$_3$): δ 5.52 (ddt, J=17.2, 10.0, 7.4 Hz, 1H), 5.22-5.09 (m, 2H), 3.14-2.99 (m, 1H), 2.96-2.79 (m, 2H), 2.79-2.47 (m, 3H), 2.15-1.89 (m, 2H), 1.60 (s, 3H). 13C NMR (126 MHz, CDCl$_3$): δ 207.78, 184.99, 131.33, 120.56, 112.36, 112.27, 85.68, 57.31, 42.11, 37.25, 34.61, 22.97, 19.09. HRMS (ESI-TOF) m/z: Calcd for C$_{13}$H$_{13}$N$_2$O [M–H]$^-$ 213.1033; Found 213.1039.

2-allyl-2,5,5-trimethylcyclohexane-1,3-dione (4m). Prepared from allylated 7c by general procedure C with the following notes: Conditions: overnight, reflux (bath temperature=130° C.). Yellow oil, 0.794 g, 64%. $^1$H NMR (500 MHz, CDCl$_3$): δ 5.56 (dddd, J=17.7, 9.8, 8.0, 6.9 Hz, 1H), 5.21-5.10 (m, 2H), 3.00 (d, J=15.4 Hz, 1H), 2.76-2.69 (m, 1H), 2.68-2.59 (m, 2H), 2.42 (s, 2H), 1.65 (s, 3H), 1.15 (s, 3H), 0.97 (s, 3H). $^{13}$C NMR (126 MHz, CDCl$_3$): δ 207.36, 183.07, 130.84, 121.02, 112.73, 112.31, 86.50, 57.32, 51.14, 47.58, 43.70, 32.93, 30.39, 27.99, 21.57. HRMS (ESI-TOF) m/z: Calcd for $C_{15}H_{17}N_2O$ [M−H]$^−$ 241.1346; Found 241.1358.

2-(2-methyl-2-(2-methylallyl)-3-oxocyclohexylidene)malononitrile (4n).

Prepared from allylated 7d by general procedure C with the following notes: Conditions: overnight, reflux (bath temperature=130° C.). Orange oil, 0.328 g, 43%. $^1$H NMR (500 MHz, CDCl$_3$): δ 4.89 (s, 1H), 4.60 (s, 1H), 3.16-3.07 (m, 1H), 3.04 (dd, J=14.7, 1.3 Hz, 1H), 2.92 (dd, J=14.8, 0.9 Hz, 1H), 2.87-2.79 (m, 1H), 2.71-2.54 (m, 2H), 2.13-2.05 (m, 1H), 2.03-1.93 (m, 1H), 1.66 (dt, J=1.6, 0.7 Hz, 3H). $^{13}$C NMR (126 MHz, CDCl$_3$): δ 207.62, 184.90, 140.29, 116.17, 112.46, 112.43, 85.83, 57.05, 44.93, 37.50, 34.53, 25.20, 23.95, 19.19. HRMS (ESI-TOF) m/z: Calcd for $C_{14}H_{19}N_2O$ [M+H]$^+$ 229.1339; Found 229.1341.

methyl 2-(2-(2-(acetoxymethyl)allyl)-2-methyl-3-oxocyclopentylidene)-2-cyanoacetate (SI-10). Prepared from allylated 2-methyl-1,3-cyclopentanone with 2d by general procedure C with the following notes: Conditions: overnight, reflux (bath temperature=130° C.). Dark-purple oil, 5.9g, 59%. $^1$H NMR (500 MHz, CDCl$_3$): δ 5.06 (s, 1H), 4.86 (s, 1H), 4.30 (s, 2H), 3.86 (s, 3H), 3.53 (ddd, J=22.0, 10.6, 6.1 Hz, 1H), 3.34 (ddd, J=22.0, 10.9, 7.5 Hz, 1H), 3.11 (d, J=14.8 Hz, 1H), 2.73 (d, J=14.7 Hz, 1H), 2.64-2.47 (m, 2H), 2.08 (s, 3H), 1.46 (s, 3H). $^{13}$C NMR (126 MHz, CDCl$_3$): δ 217.27, 184.53, 170.43, 161.91, 139.09, 117.17, 114.47, 103.45, 66.29, 56.49, 52.88, 39.23, 34.53, 29.64, 23.44, 20.83.

HRMS (ESI-TOF) m/z: Calcd for $C_{16}H_{19}NaNO_5$ [M+Na]$^+$ 328.1155; Found 328.1163.

ethyl 1-allyl-2-(dicyanomethylene)cyclohexane-1-carboxylate (SI-12). Prepared from allylated ethyl 2-oxocyclohexanecarboxylate[20] by general procedure C with the following notes: Conditions: overnight, reflux (bath temperature=130° C.). Light yellow oil, 9.5 g, 80%. $^1$H NMR (500 MHz, CDCl$_3$): δ 5.80 (dddd, J=16.7, 10.1, 8.2, 6.5 Hz, 1H), 5.22-5.06 (m, 2H), 4.34-4.18 (m, 2H), 2.95-2.82 (m, 2H), 2.68 (ddt, J=14.0, 8.2, 1.0 Hz, 1H), 2.57-2.45 (m, 1H), 2.13-2.04 (m, 1H), 1.93-1.80 (m, 2H), 1.77-1.64 (m, 3H), 1.31 (t, J=7.2 Hz, 3H). $^{13}$C NMR (126 MHz, CDCl$_3$): δ 180.91, 171.69, 131.81, 120.34, 112.44, 111.86, 86.03, 62.28, 55.16, 40.53, 35.25, 33.20, 24.26, 19.67, 14.05. HRMS (ESI-TOF) m/z: Calcd for $C_{15}H_{19}N_2O_2$ [M+H]$^+$ 259.1441; Found 259.1442.

2-allyl-2-(9-allyl-1,4-dioxaspiro[4.5]dec-7-en-8-yl)malononitrile (5a). Prepared from 4a by general procedure D with the following notes: Conditions: DCM, room temperature, 40 min, electrophile 2b Yellow oil, 0.072 g, 74%. $^1$H NMR (500 MHz, CDCl$_3$): δ 6.12 (1H, t, J=4.1 Hz), 5.95-5.71 (2H, m), 5.48-5.36 (2H, m), 5.19-5.09 (2H, m), 4.04-3.84 (4H, m), 2.87 (1H, dd, J=13.9, 7.2 Hz), 2.81 (1H, dd, J=13.8, 7.3 Hz), 2.71-2.56 (2H, m), 2.52-2.41 (3H, m), 1.89 (1H, dd, J=13.6, 5.0 Hz), 1.79 (1H, dd, J=13.3, 6.1 Hz). 13C NMR (126 MHz, CDCl$_3$): δ 135.5, 131.1, 128.9, 128.6, 123.3, 117.9, 114.7, 114.6, 106.7, 64.6, 64.1, 43.4, 41.7, 37.0, 36.7, 36.4, 34.6. HRMS (ESI-TOF) m/z: Calcd for $C_{17}H_{20}N_2NaO_2$ [M+Na]$^+$ 285.1598; Found 285.1604.

2-allyl-2-(7-allyl-1,4-dioxaspiro[4.5]dec-6-en-6-yl)malononitrile (5b). Prepared from 4b by general procedure D with the following notes: Reaction time: DCM, room temperature, 18 h, electrophile 2b. Yellow oil, 0.017 g, 50%. $^1$H NMR (Chloroform-d, 500 MHz) δ 6.04 (1H, ddt, J=17.4, 10.3, 7.3 Hz), 5.82 (1H, ddt, J=16.7, 10.3, 6.5 Hz), 5.51-5.32 (2H, m), 5.24-5.07 (2H, m), 4.29-4.13 (2H, m), 4.09-3.92 (2H, m), 3.12 (2H, d, J=6.4 Hz), 2.86 (2H, d, J=7.2 Hz), 2.16 (2H, t, J=6.0 Hz), 1.79-1.61 (4H, m). $^{13}$C NMR (cdcl3, 126 MHz) δ 146.0, 133.0, 129.7, 124.7, 122.4, 118.6, 115.2, 106.6, 63.4, 44.4, 38.8, 36.6, 34.7, 32.7, 31.4, 19.0. HRMS (ESI-TOF) m/z: Calcd for $C_{17}H_{21}N_2O_2$ [M+H]$^+$ 285.1598; Found 285.1596.

2-allyl-2-(9-(2-methylallyl)-1,4-dioxaspiro[4.5]dec-7-en-8-yl)malononitrile (5c). Prepared from 4c by general procedure D with the following notes: Conditions: DCM, room temperature, overnight, electrophile 2b Yellow oil, 0.072 g, 81%. $^1$H NMR (500 MHz, CDCl$_3$): δ 6.04 (1H, ddt, J=17.2, 10.1, 7.3 Hz), 5.84 (1H, ddt, J=16.6, 10.1, 6.2 Hz), 5.55-5.40 (2H, m), 5.31-5.12 (2H, m), 3.19 (2H, dt, J=6.4, 1.6 Hz), 2.91 (2H, dt, J=7.3, 1.1 Hz), 2.59 (2H, t, J=7.0 Hz), 2.45 (2H, t, J=7.0 Hz), 1.60 (6H, s). $^{13}$C NMR (126 MHz, CDCl$_3$): δ 209.8, 138.6, 132.6, 131.6, 128.6, 123.6, 119.0, 115.6, 48.6, 44.7, 39.5, 38.4, 34.6, 30.2, 24.1. HRMS (ESI-TOF) m/z: Calcd for $C_{17}H_{20}N_2NaO$ [M+Na]$^+$ 291.1474; Found 291.1457.

2-allyl-2-(7-allylcyclohept-1-en-1-yl)malononitrile (5d). Prepared from 4d by general procedure D with the following notes: Conditions: DCM, room temperature, 30 min, electrophile 2b Yellow oil, 0.115 g, 73%. $^1$H NMR (500 MHz, CDCl$_3$): δ 6.31 (1H, ddd, J=8.8, 5.3, 1.6 Hz), 5.87 (1H, ddt, J=17.2, 10.2, 7.2 Hz), 5.75 (1H, dddd, J=16.6, 10.1, 8.0, 6.3 Hz), 5.45-5.36 (2H, m), 5.18-5.05 (2H, m), 2.79 (1H, ddt, J=13.8, 7.2, 1.1 Hz), 2.70 (1H, ddt, J=13.8, 7.2, 1.1 Hz), 2.62 (1H, ddd, J=13.9, 11.2, 8.0 Hz), 2.50-2.38 (1H, m), 2.37-2.24 (3H, m), 1.93 (1H, dq, J=13.8, 4.4 Hz), 1.86-1.74 (3H, m), 1.39 (1H, dddd, J=13.9, 9.6, 6.1, 2.8 Hz), 1.32-1.15 (1H, m). $^{13}$C NMR (126 MHz, CDCl$_3$): δ 136.2, 135.6, 133.7, 128.8, 123.0, 117.2, 114.4, 114.4, 45.3, 42.0, 40.3, 33.7, 28.6, 27.5, 26.7, 25.1. HRMS (ESI-TOF) m/z: Calcd for $C_{16}H_{19}N_2$ [M−H]$^−$ 239.1554; Found 239.1559.

2-allyl-2-(3-allyl-3,6-dihydro-2H-pyran-4-yl)malononitrile (5e). Prepared from 4e by general procedure D with the following notes: Conditions: DCM, room temperature, 30 min, electrophile 2b. Clear colorless oil, 0.052 g, 86%. $^1$H NMR (500 MHz, CDCl$_3$) δ 6.23-6.11 (1H, m), 5.95-5.72 (2H, m), 5.52-5.37 (2H, m), 5.22-5.10 (2H, m), 4.33 (1H, dd, J=17.8, 3.1 Hz), 4.21 (1H, dt, J=18.0, 2.4 Hz), 3.99 (1H, dd, J=11.0, 1.5 Hz), 3.43 (1H, dt, J=11.3, 2.0 Hz), 2.90-2.78 (2H, m), 2.61-2.49 (1H, m), 2.46-2.33 (1H, m), 2.21 (1H, d, J=10.4 Hz). $^{13}$C NMR (125 MHz, CDCl$_3$): 135.0, 130.0, 129.0, 128.3, 123.5, 118.0, 114.1, 114.0, 65.9, 65.1, 43.4, 41.8, 35.9, 35.4. HRMS (ESI-TOF) m/z: Calcd for $C_{14}H_{17}N_2O$ [M+H]$^+$ 229.1332; Found 229.1326.

2-allyl-2-(2-allyl-3,4-dihydronaphthalen-1-yl)malononitrile (5f). Prepared from 4f by general procedure D with the following notes: Conditions: toluene, 80° C., 12 h, electrophile 2b. Light yellow crystals, 0.313g, 58%. $^1$H NMR (500 MHz, CDCl$_3$): δ 7.44 (1H, d, J=7.7 Hz), 7.35-7.06 (2H, m), 6.01 (1H, ddt, J=6.7, 2.8, 2.3 Hz), 5.96-5.85 (1H, m), 5.51-5.38 (2H, m), 5.28-5.17 (2H, m), 3.35 (2H, dd, J=6.1, 1.8 Hz), 2.23 (2H, d, J=7.8 Hz), 6.11-5.79 (2H, m), 3.13 (2H, dd, J=7.1 0.8 Hz), 2.63 (2H, d, J=7.1 Hz). $^{13}$C NMR (126 MHz, CDCl$_3$): δ 144.7, 137.1, 133.5, 131.8, 128.7, 127.5, 127.5, 125.9, 123.5, 123.4, 118.5, 115.4, 43.2, 39.2, 39.1, 30.3, 28.1, 21.9. HRMS (ESI-TOF) m/z: Calcd for $C_{19}H_{18}N_2Na$ [M+Na]$^+$ 297.1362; Found 297.1348.

2-allyl-2-(9-(2-methylallyl)-1,4-dioxaspiro[4.5]dec-7-en-8-yl)malononitrile (5g). Prepared from 4g by general procedure D with the following notes: Conditions: DCM, room temperature, 2 h, electrophile 2b. Clear oil, 0.263 g, 46%. $^1$H NMR (500 MHz, CDCl$_3$): δ 6.11 (1H, t, J=4.1 Hz), 5.89 (1H, ddt, J=17.0, 10.0, 7.3 Hz), 5.48-5.35 (2H, m), 4.92-4.84 (1H, m), 2.47-2.37 (3H, m), 4.78 (1H, d, J=2.5 Hz), 4.06-3.85 (4H, m), 1.77-1.74 (3H, m), 2.95-2.84 (1H, m), 2.85-2.77 (2H, m), 1.87-1.80 (1H, m), 2.61-2.37 (4H, m), 1.89-1.69 (5H, m), 2.60-2.49 (1H, m). $^{13}$C NMR (126 MHz, CDCl$_3$): δ 142.4, 131.3, 128.8, 128.7, 123.3, 114.8, 114.6, 113.9, 106.7, 64.7, 64.5, 64.2, 43.7, 41.7, 40.7, 36.5, 35.0, 34.1, 21.4. HRMS (ESI-TOF) m/z: Calcd for C$_{18}$H$_{20}$N$_2$NaO$_4$ [M+Na]$^+$ 321.1573; Found 321.1568.

2-((8-(1,1-dicyanobut-3-en-1-yl)-1,4-dioxaspiro[4.5]dec-8-en-7-yl)methyl)allyl acetate (5h). Prepared from 4h by general procedure D with the following notes: Conditions: DCM, room temperature, 2 h, electrophile 2b. Clear oil, 0.194 g, 79%. $^1$H NMR (500 MHz, CDCl$_3$): δ 6.14 (1H, t, J=4.1 Hz), 5.89 (1H, dq, J=16.9, 7.7 Hz), 5.51-5.34 (2H, m), 5.21 (1H, s), 5.07 (1H, s), 4.65-4.49 (2H, m), 4.02-3.84 (4H, m), 2.95-2.77 (3H, m), 2.72 (1H, d, J=13.9 Hz), 2.54-2.41 (3H, m), 2.09 (3H, s), 1.86 (1H, dd, J=13.8, 4.4 Hz), 1.78 (1H, dd, J=13.6, 5.8 Hz). $^{13}$C NMR (126 MHz, CDCl$_3$): δ 170.8, 140.8, 131.0, 129.2, 128.6, 123.4, 116.5, 114.7, 114.6, 110.0, 106.6, 66.1, 64.7, 64.2, 43.5, 41.6, 36.6, 36.1, 34.9, 34.3, 21.0. HRMS (ESI-TOF) m/z: Calcd for C$_{20}$H$_{24}$N$_2$NaO$_4$ [M+Na]$^+$ 379.1628; Found 379.1630.

2-allyl-2-((S)-6-((R)-hex-1-en-3-yl)cyclohex-1-en-1-yl)malononitrile (5i). Prepared from 4l by general procedure D with the following notes: Conditions: THF, 50° C., 3 h, base: K$_2$CO$_3$, electrophile 2a. Clear oil, 0.090 g, 67%. $^1$H NMR (500 MHz, CDCl$_3$): δ 6.35-6.27 (m, 1H), 5.99-5.70 (m, 3H), 5.48-5.33 (m, 2H), 5.20-5.08 (m, 2H), 2.89-2.75 (m, 2H), 2.54-2.41 (m, 2H), 2.21-2.11 (m, 2H), 1.89-1.80 (m, 1H), 1.77-1.63 (m, 1H), 1.62-1.48 (m, 3H), 1.35 (dddd, J=22.3, 9.9, 5.6, 2.4 Hz, 3H), 1.26-1.14 (m, 1H), 0.89 (t, J=7.0 Hz, 4H). $^{13}$C NMR (126 MHz, CDCl$_3$): δ 140.87, 133.29, 130.88, 129.12, 123.15, 116.76, 115.30, 115.23, 45.94, 43.93, 42.49, 41.50, 32.37, 25.41, 24.24, 21.32, 18.97, 14.49. HRMS (ESI-TOF) m/z: Calcd for C$_{18}$H$_{24}$N$_2$Na [M+Na]$^+$ 268.40; Found 291.1832. Note: Stereochemistry was assigned based on 6i.

2-(8-(1,1-dicyanobut-3-en-1-yl)-1,4-dioxaspiro[4.5]dec-8-en-7-yl)but-3-en-1-yl acetate (5j). Prepared from 4j by general procedure D with the following notes: Conditions: THF, 50° C., 3 h, base: K$_2$CO$_3$, 0.25 mol % Pd(PPh$_3$)$_4$ used, electrophile 2a. Light yellow oil, 16 g, 52%. $^1$H NMR (500 MHz, CDCl$_3$): δ 6.22 (ddd, J=6.5, 2.6, 1.1 Hz, 1H), 5.99-5.77 (m, 2H), 5.50-5.35 (m, 2H), 5.29-5.18 (m, 2H), 4.23 (dd, J=11.3, 8.3 Hz, 1H), 4.10 (dd, J=11.3, 3.9 Hz, 1H), 4.05-3.84 (m, 5H), 3.14 (dt, J=8.0, 4.0 Hz, 1H), 2.98-2.76 (m, 3H), 2.52-2.30 (m, 2H), 2.04 (s, 3H), 1.89 (ddd, J=13.7, 6.3, 2.2 Hz, 1H), 1.80 (dd, J=13.6, 8.3 Hz, 1H). $^{13}$C NMR (126 MHz, CDCl$_3$): δ 171.25, 136.90, 130.85, 130.30, 128.68, 123.65, 118.28, 114.74, 110.13, 107.02, 64.82, 64.52, 63.77, 43.49, 42.61, 41.99, 40.41, 36.32, 33.53, 21.01. HRMS (ESI-TOF) m/z: Calcd for C$_{20}$H$_{24}$N$_2$NaO$_4$ [M+Na]$^+$ 356.42; Found 374.2074. Note: Stereochemistry was assigned based on 6j.

2-allyl-2-(5-allyl-5-methyl-4-oxocyclopent-1-en-1-yl)malononitrile (5k). Prepared from 4k by general procedure D with the following notes: Conditions: THF, 40° C., 1 h, electrophile 2a. Orange-brown oil, 0.224 g, 62%. Large scale: 5.5 g was prepared using the same procedure. $^1$H NMR (500 MHz, CDCl$_3$): δ 6.53 (t, J=2.5 Hz, 1H), 5.94 (ddt, J=17.2, 10.3, 7.3 Hz, 1H), 5.59-5.43 (m, 3H), 5.16-5.07 (m, 2H), 3.02-2.94 (m, 2H), 2.92-2.84 (m, 2H), 2.79 (dd, J=14.4, 7.4 Hz, 1H), 2.49 (dd, J=14.3, 7.6 Hz, 1H), 1.38 (s, 3H). 13C NMR (126 MHz, CDCl$_3$): δ 216.17, 137.92, 131.96, 130.42, 128.36, 124.18, 120.04, 114.13, 114.07, 57.17, 44.26, 41.89, 41.87, 37.82, 21.78. HRMS (ESI-TOF) m/z: Calcd for C$_{15}$H$_{20}$N$_3$O [M+NH$_4$]$^+$258.1601; Found 258.1612.

2-allyl-2-(6-allyl-6-methyl-5-oxocyclohex-1-en-1-yl)malononitrile (5i). Prepared from 4l by general procedure D with the following notes: Conditions: THF, room temperature, 10 min, electrophile 2a. Light yellow oil, 0.355 g, 82%. $^1$H NMR (500 MHz, CDCl$_3$): δ 6.50-6.43 (m, 1H), 6.02-5.84 (m, 1H), 5.62-5.37 (m, 3H), 5.17-5.06 (m, 2H), 3.03-2.76 (m, 4H), 2.69-2.42 (m, 4H), 1.50 (s, 3H). $^{13}$C NMR (126 MHz, CDCl$_3$): δ 209.94, 134.60, 132.65, 132.51, 128.70, 123.92, 119.63, 115.43, 115.38, 53.02, 46.15, 42.29, 40.21, 35.41, 23.68, 22.26. HRMS (ESI-TOF) m/z: Calcd for C$_{16}$H$_{22}$N$_3$O [M+NH$_4$]$^+$272.1757; Found 272.1746.

2-allyl-2-(6-allyl-3,3,6-trimethyl-5-oxocyclohex-1-en-1-yl)malononitrile (5m). Prepared from 4m by general procedure D with the following notes: Conditions: THF, room temperature, overnight, electrophile 2a. Colorless oil, 0.257 g, 73%. $^1$H NMR (500 MHz, CDCl$_3$): δ 6.12 (s, 1H), 5.98-5.84 (m, 1H), 5.61-5.50 (m, 1H), 5.50-5.37 (m, 2H), 5.19-5.09 (m, 2H), 3.02-2.76 (m, 4H), 2.49 (d, J=13.1 Hz, 1H), 2.38 (d, J=13.3 Hz, 1H), 1.47 (s, 3H), 1.14 (s, 3H), 1.05 (s, 3H). $^{13}$C NMR (126 MHz, CDCl$_3$): δ 208.89, 142.33, 132.79, 132.46, 128.65, 124.01, 119.70, 115.59, 115.57, 51.83, 49.83, 47.06, 41.65, 39.61, 36.04, 29.62, 29.19, 27.91, 22.13. HRMS (ESI-TOF) m/z: Calcd for C$_{18}$H$_{23}$N$_2$O [M+H]$^+$ 283.1805; Found 283.1796.

2-(6-allyl-6-methyl-5-oxocyclohex-1-en-1-yl)-2-(2-methylallyl)malononitrile (5n). Prepared from 4l by general procedure D with the following notes: Conditions: THF, 40° C., overnight, electrophile 2c. Light yellow oil, 0.100 g, 65%. $^1$H NMR (500 MHz, CDCl$_3$): δ 6.53-6.44 (m, 1H), 5.63-5.48 (m, 1H), 5.22 (tq, J=2.5, 1.5, 1.0 Hz, 1H), 5.16-5.08 (m, 3H), 2.95-2.74 (m, 4H), 2.67-2.43 (m, 6H), 1.98 (s, 3H), 1.51 (s, 3H). $^{13}$C NMR (126 MHz, CDCl$_3$): δ 209.80, 137.09, 135.47, 132.55, 132.12, 119.84, 119.48, 115.80, 115.58, 52.94, 49.83, 42.20, 35.22, 23.61, 23.26, 21.89. HRMS (ESI-TOF) m/z: Calcd for C$_{17}$H$_{21}$N$_2$O [M+H]$^+$ 269.1648; Found 269.1661.

4-(6-allyl-6-methyl-5-oxocyclohex-1-en-1-yl)-4,4-dicyano-2-methylenebutyl tert-butyl carbonate (5o). Prepared from 4l by general procedure D with the following notes: Conditions: THF, 40° C., 2 h, electrophile 2e. Light yellow oil, 0.050 g, 63%. $^1$H NMR (500 MHz, CDCl$_3$): δ 6.51 (d, J=3.2 Hz, 1H), 5.58-5.45 (m, 1H), 5.16-5.08 (m, 2H), 4.73-4.65 (m, 2H), 3.03 (d, J=14.3 Hz, 1H), 2.99-2.80 (m, 4H), 2.61-2.44 (m, 5H), 1.51 (s, 3H), 1.48 (d, 9H). $^{13}$C NMR (126 MHz, CDCl$_3$): δ 209.70, 152.95, 135.67, 135.04, 132.64, 132.51, 123.05, 119.54, 115.48, 115.38, 82.79, 68.68, 52.93, 44.50, 42.15, 39.84, 35.19, 27.74 (3 overlapping C), 23.56, 21.99. HRMS (ESI-TOF) m/z: Calcd for C$_{22}$H$_{32}$N$_3$O$_4$ [M+NH$_4$]$^+$402.2387; Found 402.2391.

2-allyl-2-(6-methyl-6-(2-methylallyl)-5-oxocyclohex-1-en-1-yl)malononitrile (5p). Prepared from 4n by general procedure D with the following notes: Conditions: THF, room temperature, 20 min, electrophile 2a. Light yellow oil, 0.097 g, 82%. $^1$H NMR (500 MHz, CDCl$_3$): δ 6.46-6.42 (m, 1H), 5.93 (ddt, J=17.3, 10.1, 7.3 Hz, 1H), 5.49-5.39 (m, 2H), 4.89-4.85 (m, 1H), 4.75-4.73 (m, 1H), 3.03-2.79 (m, 4H), 2.66-2.48 (m, 4H), 1.64 (s, 3H), 1.50 (s, 3H). $^{13}$C NMR (126 MHz, CDCl$_3$): δ 210.07, 141.27, 135.18, 132.10, 128.67, 123.75, 116.00, 115.45, 115.36, 52.88, 46.76, 44.42, 40.31, 35.18, 24.00, 23.95, 23.63. HRMS (ESI-TOF) m/z: Calcd for C$_{17}$H$_{21}$N$_2$O [M+H]$^+$ 269.1648; Found 269.1660.

methyl 2-(5-(2-(acetoxymethyl)allyl)-5-methyl-4-oxocyclopent-1-en-1-yl)-2-cyanopent-4-enoate (SI-11). In a 250 mL round-bottom flask, SI-10 (2.5 g, 6.55 mmol, 1 equiv.) was dissolved in dry DMF under N$_2$. Freshly ground K$_2$CO$_3$ (1.359 g, 9.82 mmol, 1.5 equiv.) was added and the resulting suspension was stirred at room temperature for 5 min. Then, allyl bromide (680 µL, 7.86 mmol, 1.2 equiv.) was added dropwise and the reaction mixture was stirred at room temperature for 45 min. After reaction completion, the reaction mixture was diluted with H$_2$O (50 mL) and extracted with EtOAc (20 mL×3). The combined organic layers were then washed with brine and dried over Na$_2$SO$_4$. The title compound was obtained as an orange oil (2 g, 71%) after purification by column chromatography (Hexanes-Ethyl Acetate 8:1). $^1$H NMR (500 MHz, CDCl$_3$): δ 6.41 (s, 1H), 5.81 (ddt, J=17.1, 10.0, 7.2 Hz, 1H), 5.31 (d, J=5.2 Hz, 1H), 5.28 (s, 1H), 5.01 (s, 1H), 4.75 (s, 1H), 4.35 (d, J=17.6 Hz, 3H), 3.78 (s, 3H), 2.99-2.90 (m, 3H), 2.82 (d, J=15.8 Hz, 1H), 2.76 (dt, J=13.6, 6.2 Hz, 1H), 2.58 (d, J=15.9 Hz, 1H), 2.07 (s, 3H), 1.36 (s, 3H). 13C NMR (126 MHz, CDCl$_3$): δ 217.27, 170.64, 167.02, 140.84, 139.97, 130.42, 128.27, 122.08, 117.49, 115.63, 67.00, 56.47, 54.05, 49.92, 44.52, 41.46, 38.89, 24.07, 20.99.

HRMS (ESI-TOF) m/z: Calcd for C$_{19}$H$_{23}$NaNO$_5$ [M+Na]$^+$368.1468; Found 368.1481.

ethyl 1-allyl-2-(1,1-dicyanobut-3-en-1-yl)cyclohex-2-ene-1-carboxylate (SI-13). Prepared from SI-12 by general procedure D with the following notes: Conditions: THF, room temperature, 10 min, electrophile 2a. Light yellow oil, 8.8 g, 97%. $^1$H NMR (500 MHz, CDCl$_3$): δ 6.31 (t, J=4 Hz, 1H), 5.93 (dddt, J=37.2, 17.2, 10.1, 7.2 Hz, 2H), 5.48-5.37 (m, 2H), 5.26-5.14 (m, 2H), 4.24 (qt, J=7.1, 3.7 Hz, 2H), 3.03-2.76 (m, 4H), 2.30-2.11 (m, 2H), 2.01-1.84 (m, 2H), 1.68 (ddtd, J=14.5, 9.2, 6.0, 3.3 Hz, 1H), 1.62-1.53 (m, 2H), 1.33 (t, J=7.2 Hz, 3H). $^{13}$C NMR (126 MHz, CDCl$_3$): δ 175.18, 134.78, 133.70, 132.27, 129.50, 123.24, 119.42, 115.68, 115.67, 61.91, 49.82, 46.33, 40.97, 40.16, 34.83, 25.88, 17.88, 14.12. HRMS (ESI-TOF) m/z: Calcd for C$_{18}$H$_{23}$N$_2$O$_2$ [M+H]$^+$ 299.1754; Found 299.1760.

3,6,9,9a-tetrahydrospiro[benzo[7]annulene-2,2'-[1,3]dioxolane]-5,5(1H)-dicarbonitrile (Compound 6a). The compound has the structural formula:

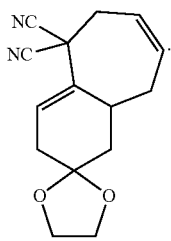 [SMILES: N#CC1(C#N)CC=CCC2CC3(CC=C21)OCCO3]

Prepared from 5a by general procedure F with the following notes: Conditions: DCM, 40° C., overnight. White solid, 0.016 g, 79%. $^1$H NMR (500 MHz, CDCl$_3$): δ 6.32 (1H, td, J=4.0, 1.3 Hz), 6.21-6.05 (1H, m), 5.74 (1H, dddd, J=11.0, 6.5, 5.5, 2.7 Hz), 4.07-3.91 (4H, m), 3.09 (1H, ddt, J=15.8, 5.5, 1.0 Hz), 2.91-2.76 (2H, m), 2.66-2.52 (1H, m), 2.46 (2H, dd, J=4.0, 2.2 Hz), 2.25 (1H, ddd, J=17.1, 7.8, 2.0 Hz), 1.97 (1H, dd, J=13.3, 6.4 Hz), 1.76 (1H, dd, J=13.3, 6.4 Hz). 13C NMR (126 MHz, CDCl$_3$): δ 135.4, 132.9, 127.6, 122.9, 115.3, 115.1, 106.5, 64.6, 64.4, 41.4, 39.2, 36.9, 36.0, 35.5, 34.9. HRMS (ESI-TOF) m/z: Calcd for C$_{15}$H$_{17}$N$_2$O$_2$ [M+H]$^+$ 257.1104; Found 257.1285.

3,4,5,8-tetrahydrospiro[benzo[7]annulene-1,2'-[1,3]dioxolane]-9,9(2H)-dicarbonitrile (Compound 6b). The compound has the structural formula:

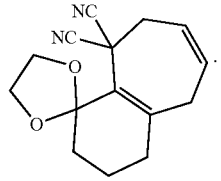 [SMILES: N#CC1(C#N)CC=CCC2=C1C1(CCC2)OCCO1]

Prepared from 5b by general procedure F with the following notes: Conditions: 100° C., 2.5 h. Transparent crystals, 0.007 g, 54%. $^1$H NMR (500 MHz, CDCl$_3$): δ 5.83-5.69 (1H, m), 5.69-5.56 (1H, m), 4.28-4.14 (2H, m), 4.08-3.92 (2H, m), 3.20-3.07 (2H, m), 3.07-2.94 (2H, m), 2.18 (2H, t, J=5.9 Hz), 1.86-1.62 (4H, m). 13C NMR (126 MHz, CDCl$_3$): δ 147.8, 127.4, 124.9, 124.0, 115.3, 106.6, 63.6, 38.1, 34.8, 34.4, 34.1, 31.9, 19.2. HRMS (ESI-TOF) m/z: Calcd for C$_{15}$H$_{16}$N$_2$NaO$_2$ [M+Na]$^+$279.1091; Found 279.1091.

4,4-dimethyl-3-oxo-1,2,3,4,6,9-hexahydro-5H-benzo[7] annulene-5,5-dicarbonitrile (Compound 6c). The compound has the structural formula:

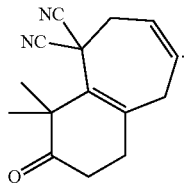 [SMILES: CC1(C)C(=O)CCC2=C1C(C#N)(C#N)CC=CC2]

Prepared from 5c by general procedure F with the following notes: Conditions: 100° C., 30 min. Colorless oil, 0.040 g, 89%. $^1$H NMR (500 MHz, CDCl$_3$): δ 5.86-5.70 (1H, m), 5.67-5.55 (1H, m), 3.30-3.17 (2H, m), 3.10-3.01 (2H, m), 2.66-2.56 (2H, m), 2.51 (2H, t, J=7.0 Hz), 1.57 (6H, s). 13C NMR (126 MHz, CDCl$_3$): δ 209.8, 140.6, δ 130.7, 127.5, 123.0, 115.6, 48.2, 39.0, 36.3, 34.9, 34.6, 34.3, 23.6. HRMS (ESI-TOF) m/z: Calcd for C$_{15}$H$_{16}$N$_2$NaO [M+Na]$^+$ 263,1155; Found 263.1147.

5,5a,6,7,8,9-hexahydroheptalene-1,1(2H)-dicarbonitrile (Compound 6d). The compound has the structural formula:

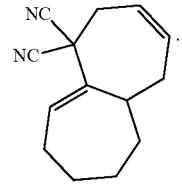

Prepared from 5d by general procedure F with the following notes: Conditions: 85° C., overnight. Colorless oil, 0.042 g, 65%. $^1$H NMR (500 MHz, CDCl$_3$): δ 6.44 (1H, t, J=6.2 Hz), 5.94 (1H, dt, J=10.5, 4.8 Hz), 5.62 (1H, dt, J=12.0, 6.4 Hz), 3.28-3.15 (1H, m), 3.01 (1H, dq, J=12.1, 4.5 Hz), 2.77 (1H, dd, J=15.5, 6.6 Hz), 2.50 (1H, ddd, J=17.0, 11.5, 4.8 Hz), 2.42-2.28 (3H, m), 2.23 (1H, dddd, J=17.4, 9.8, 6.5, 3.2 Hz), 1.91-1.67 (6H, m), 1.28 (4H, s). $^{13}$C NMR (126 MHz, CDCl$_3$): δ 136.5, 134.7, 133.8, 120.8, 115.9, 115.7, 43.0, 37.9, 37.0, 33.7, 31.7, 27.3, 26.3, 24.7. HRMS (ESI-TOF) m/z: Calcd for C$_{14}$H$_{20}$N$_3$[M+NH4]+230.1652; Found 230.1650.

3,6,9,9a-tetrahydrocyclohepta[c]pyran-5,5(1H)-dicarbonitrile (Compound 6e). The compound has the structural formula:

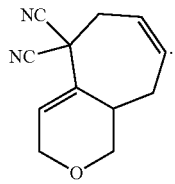

Prepared from 5e by general procedure F with the following notes: Conditions: 85° C., overnight. White solid, 0.058 g, 89%. $^1$H NMR (500 MHz, CDCl$_3$): δ 6.39-6.30 (1H, m), 6.18-6.06 (1H, m), 5.79-5.68 (1H, m), 4.35-4.18 (2H, m), 3.80-3.66 (2H, m), 3.12 (1H, dd, J=15.0, 7.1 Hz), 2.70 (1H, dd, J=15.0, 5.0 Hz), 2.56-2.42 (2H, m), 2.42-2.31 (1H, m). $^{13}$C NMR (126 MHz, CDCl$_3$): δ 135.8, 132.1, 127.7, 122.4, 114.7, 114.3, 69.7, 65.3, 41.0, 36.9, 34.0, 33.7. HRMS (ESI-TOF) m/z: Calcd for C$_{12}$H$_{16}$N$_3$O [M+NH4]+ 218.1294; Found 218.1294.

5,6,7,10-tetrahydro-11H-cyclohepta[a]naphthalene-11,11-dicarbonitrile (Compound 6f). The compound has the structural formula:

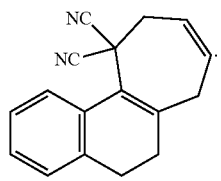 [SMILES: N#CC1(C#N)CC=CCC2=C1c1ccccc1CC2]

Prepared from 5f by general procedure F with the following notes: Conditions: 85° C., overnight. White solid, 0.071 g, 80%. $^1$H NMR (500 MHz, CDCl$_3$): δ 7.77 (1H, d, J=7.9 Hz), 7.31 (1H, t, J=7.8 Hz), 7.22 (1H, tt, J=7.4, 1.2 Hz), 7.16 (1H, d, J=7.4 Hz), 6.17 (1H, dt, J=10.2, 5.2 Hz), 6.11 (1H, dt, J=10.0, 6.8 Hz), 3.29 (2H, d, J=6.7 Hz), 3.25 (2H, d, J=4.8 Hz), 2.69 (2H, t, J=7.5 Hz), 2.31 (2H, t, J=7.5 Hz). $^{13}$C NMR (126 MHz, CDCl$_3$): δ 142.6, 135.7, 134.3, 133.2, 127.6, 127.4, 126.5, 126.2, 123.4, 123.2, 115.7, 110.0, 36.4, 35.4, 35.1, 33.7, 27.8. HRMS (ESI-TOF) m/z: Calcd for C$_{17}$H$_{14}$N$_2$Na [M+Na]+269.1041; Found 269.1049.

8-methyl-3,6,9,9a-tetrahydrospiro[benzo[7]annulene-2,2'-1,3]dioxolane]-5,5(1H)-dicarbonitrile (Compound 6g). The compound has the structural formula:

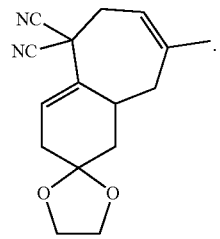 [SMILES: CC1=CCC(C#N)(C#N)C2=CCC3(CC2C1)OCCO3]

Prepared from 5g by general procedure F with the following notes: Conditions: 100° C., 30 min. White solid, 0.099 g, 73%. $^1$H NMR (500 MHz, CDCl$_3$): δ 6.25 (1H, t, J=3.3 Hz), 5.48 (1H, t, J=6.2 Hz), 4.05-3.87 (4H, m), 2.97 (1H, dd, J=15.3, 6.1 Hz), 2.88-2.68 (2H, m), 2.69-2.53 (1H, m), 2.47-2.33 (2H, m), 2.10-1.89 (2H, m), 1.82 (3H, s), 1.75-1.67 (1H, m). $^{13}$C NMR (126 MHz, CDCl$_3$): δ 144.7, 133.2, 127.0, δ 117.0, 115.3, 115.0, 106.5, 64.6, 64.4, 41.5, 40.5, 39.4, 36.5, 35.9, 34.7, 25.8. HRMS (ESI-TOF) m/z: Calcd for C$_{16}$H$_{18}$N$_2$NaO$_2$ [M+Na]+293.1260; Found 293.1270.

(5,5-dicyano-1,3,5,6,9,9a-hexahydrospiro[benzo[7]annulene-2,2'-[1,3]dioxolan]-8-yl)methyl acetate (Compound 6h). The compound has the structural formula:

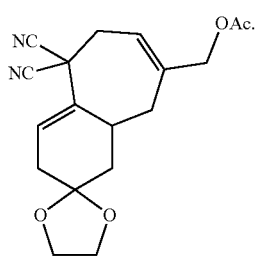 [SMILES: CC(=O)OCC1=CCC(C#N)(C#N)C2=CCC3(CC2C1)OCCO3]

Prepared from 5h by general procedure F with the following notes: Conditions: 100° C., 5 h. Colorless oil, 0.021 g, 44%. $^1$H NMR (500 MHz, CDCl$_3$): δ 6.28 (1H, t, J=4.0 Hz), 5.78 (1H, t, J=6.3 Hz), 4.51 (2H, s), 4.03-3.91 (4H, m), 3.06 (1H, dd, J=15.3, 6.4 Hz), 2.86-2.73 (2H, m), 2.62 (1H, dd, J=16.0, 12.6 Hz), 2.43 (2H, dd, J=3.9, 2.0 Hz), 2.09 (4H, s), 1.98 (1H, dd, J=13.3, 6.0 Hz), 1.76 (1H, dd, J=13.4, 6.1 Hz). $^{13}$C NMR (500 MHz, CDCl$_3$): δ 170.5, 142.6, 132.6, 127.6, 120.2, 115.0, 114.6, 106.4, 67.8, 64.6, 64.4, 41.2, 39.2, 36.4, 36.3, 35.9, 34.9, 20.9. HRMS (ESI-TOF) m/z: Calcd for C$_{18}$H$_{20}$N$_2$NaO$_4$ [M+Na]+351.1315; Found 351.1330.

(9R,9aS)-9-propyl-1,2,3,6,9,9a-hexahydro-5H-benzo[7]annulene-5,5-dicarbonitrile (Compound 6). The compound has the structural formula:

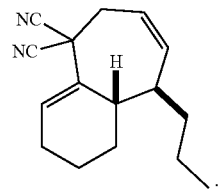

Prepared from 5l by general procedure F with the following notes: Conditions: 80° C., overnight. Clear oil, 0.020 g, 99%. $^1$H NMR (500 MHz, CDCl$_3$): δ 6.34 (t, J=3.7 Hz, 1H), 5.91 (dd, J=10.8, 6.3 Hz, 1H), 5.65 (dt, J=10.8, 7.1 Hz, 1H), 3.06 (dd, J=14.3, 6.7 Hz, 1H), 2.69 (dd, J=14.3, 7.5 Hz, 1H), 2.37 (dd, J=9.4, 3.1 Hz, 1H), 2.22 (t, J=4.7 Hz, 2H), 2.19-2.05 (m, 1H), 1.89-1.78 (m, 1H), 1.68 (d, J=5.7 Hz, 1H), 1.61-1.37 (m, 5H), 1.26 (d, J=4.3 Hz, 1H), 0.92 (t, J=7.2 Hz, 3H). $^{13}$C NMR (126 MHz, CDCl$_3$): δ 141.01, 132.69, 132.37, 120.28, 115.99, 44.34, 41.37, 36.44, 36.18, 33.95, 26.52, 25.46, 19.94, 16.33, 14.44. HRMS (ESI-TOF) m/z: Calcd for C$_{16}$H$_{21}$N$_2$ [M+H]+ 240.35; Found 241.1699.

(5,5-dicyano-1,3,5,6,9,9a-hexahydrospiro[benzo[7]annulene-2,2'-dioxolan]-9-yl)methyl acetate (Compound 6i). The compound has the structural formula:

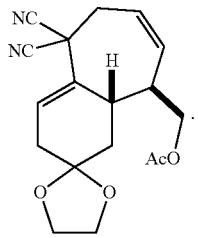

Prepared from 5j by general procedure F with the following notes: Conditions: 80° C., overnight. Light Yellow Solid, 0.016 g, 53%. $^1$H NMR (500 MHz, CDCl$_3$): δ 6.35 (t, J=3.9 Hz, 1H), 5.91 (dd, J=11.0, 5.3 Hz, 1H), 5.86-5.73 (m, 1H), 4.23 (qd, J=11.3, 4.1 Hz, 2H), 4.07-3.85 (m, 5H), 3.12 (dt, J=14.8, 5.4 Hz, 2H), 2.85 (ddd, J=9.7, 5.9, 2.3 Hz, 1H), 2.74 (dd, J=14.7, 6.8 Hz, 1H), 2.49 (d, J=3.9 Hz, 2H), 2.09 (s, 3H), 2.05-1.97 (m, 1H), 1.92 (dd, J=14.0, 5.8 Hz, 1H). $^{13}$C NMR (126 MHz, CDCl$_3$): δ 171.18, 138.29, 131.72, 130.31, 122.69, 115.48, 115.28, 106.60, 65.44, 64.95, 64.31, 41.92, 41.44, 36.96, 35.32, 35.24, 34.45, 21.08. HRMS (ESI-TOF) m/z: Calcd for C$_{18}$H$_{21}$N$_2$O$_4$ [M+H]$^+$ 328.14; Found 329.1496.

8a-methyl-1-oxo-2,5,8,8a-tetrahydroazulene-4,4(1H)-dicarbonitrile (Compound 6k). The compound has the structural formula:

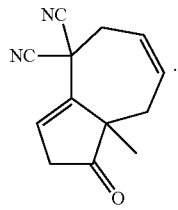

Prepared from 3o by general procedure F with the following notes: Conditions: 80° C., overnight. Beige solid, 0.037 g, 83%. Large scale: 3.5 g was prepared using the same procedure. $^1$H NMR (500 MHz, CDCl$_3$): δ 6.65 (t, J=2.4 Hz, 1H), 6.30-6.20 (m, 1H), 6.07-5.96 (m, 1H), 3.19-2.97 (m, 4H), 2.82-2.74 (m, 1H), 2.43 (dd, J=14.6, 8.3 Hz, 1H), 2.22-2.11 (m, 1H), 1.35 (s, 3H). $^{13}$C NMR (126 MHz, CDCl$_3$): δ 215.85, 140.98, 134.97, 127.82, 125.72, 114.25, 113.72, 53.76, 39.92, 37.16, 36.93, 34.01, 21.30. HRMS (ESI-TOF) m/z: Calcd for C$_{13}$H$_{12}$N$_2$NaO [M+Na]$^+$ 235.0842; Found 235.0850.

9a-methyl-1-oxo-1,2,3,6,9,9a-hexahydro-5H-benzo[7]annulene-5,5-dicarbonitrile (Compound 6l). The compound has the structural formula:

Prepared from 5l by general procedure F with the following notes: Conditions: 80° C., overnight. Colorless oil, 0.024 g, 70%. $^1$H NMR (500 MHz, CDCl$_3$): δ 6.67 (dd, J=5.7, 3.6 Hz, 1H), 5.99-5.90 (m, 1H), 5.65-5.59 (m, 1H), 3.23-3.13 (m, 1H), 2.96-2.88 (m, 1H), 2.82-2.69 (m, 2H), 2.67-2.59 (m, 2H), 2.58-2.50 (m, 1H), 2.40-2.31 (m, 1H), 1.43 (s, 3H). $^{13}$C NMR (126 MHz, CDCl$_3$): δ 209.94, 135.06, 131.32, 131.12, 123.66, 115.90, 115.55, 53.01, 40.51, 39.21, 34.31, 32.24, 24.80, 23.26. HRMS (ESI-TOF) m/z: Calcd for C$_{14}$H$_{18}$N$_3$O [M+NH$_4$]$^+$244.1444; Found 244.1434.

3,3,9a-trimethyl-1-oxo-1,2,3,6,9,9a-hexahydro-5H-benzo[7]annulene-5,5-dicarbonitrile (Compound 6m). The compound has the structural formula:

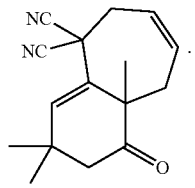

Prepared from 5m by general procedure F with the following notes: Conditions: 80° C., overnight. Beige solid, 0.039 g, 87%. $^1$H NMR (500 MHz, CDCl$_3$): δ 6.40 (s, 1H), 6.11-6.02 (m, 1H), 5.89-5.78 (m, 1H), 3.22-3.12 (m, 1H), 2.95-2.86 (m, 1H), 2.72-2.61 (m, 2H), 2.45 (dd, J=15.7, 6.2 Hz, 1H), 2.32 (d, J=13.2 Hz, 1H), 1.51 (s, 3H), 1.19 (s, 3H), 1.05 (s, 3H). $^{13}$C NMR (126 MHz, CDCl$_3$): δ 209.33, 141.32, 133.15, 132.78, 124.63, 115.77, 115.66, 50.73, 48.89, 38.99, 38.89, 35.98, 33.39, 29.25, 28.97, 24.97. HRMS (ESI-TOF) m/z: Calcd for C$_{16}$H$_{22}$N$_3$O [M+NH4]+ 272.1757; Found 272.1758.

7,9a-dimethyl-1-oxo-1,2,3,6,9,9a-hexahydro-5H-benzo[7]annulene-5,5-dicarbonitrile (Compound 6n). The compound has the structural formula:

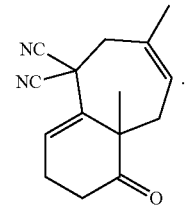

Prepared from 5n by general procedure F with the following notes: Conditions: 80° C., overnight. Colorless oil, 0.030 g, 66%. $^1$H NMR (500 MHz, CDCl$_3$): δ 6.66 (dd, J=5.2, 3.8 Hz, 1H), 5.72 (t, J=7.0 Hz, 1H), 3.06 (d, J=15.6 Hz, 1H), 2.89 (d, J=15.7 Hz, 1H), 2.72 (dt, J=15.0, 6.5 Hz, 1H), 2.67-2.47 (m, 4H), 2.42-2.34 (m, 1H), 1.85 (dd, J=1.9, 1.1 Hz, 3H), 1.44 (s, 3H). $^{13}$C NMR (126 MHz, CDCl$_3$): δ 210.08, 135.25, 132.91, 131.12, 125.68, 115.64, 115.58, 52.09, 44.00, 38.49, 34.49, 32.59, 25.02, 24.42, 23.56. HRMS (ESI-TOF) m/z: Calcd for C$_{15}$H$_{20}$N$_3$O [M+NH4]+ 258.1601; Found 258.1589.

tert-butyl((5,5-dicyano-9a-methyl-1-oxo-2,3,5,6,9,9a-hexahydro-1H-benzo[7]annulen-7-yl)methyl) carbonate (Compound 6o). The compound has the structural formula:

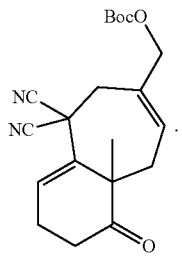

Prepared from 5o by general procedure F with the following notes: Conditions: 80° C., overnight. Colorless oil, 0.030 g, 70%. $^1$H NMR (500 MHz, CDCl$_3$): δ 6.69 (dd, J=5.3, 3.8 Hz, 1H), 6.07 (t, J=6.9 Hz, 1H), 4.55-4.45 (m, 2H), 3.25-3.17 (m, 1H), 2.98 (d, J=16.3 Hz, 1H), 2.80-2.71 (m, 2H), 2.63-2.50 (m, 3H), 2.42-2.33 (m, 1H), 1.49 (s, 9H), 1.45 (s, 3H). $^{13}$C NMR (126 MHz, CDCl$_3$): δ 209.62, 153.16, 134.71, 131.79, 131.34, 130.83, 115.62, 115.36, 82.91, 70.63, 52.32, 40.75, 38.70, 34.29, 32.19, 27.87 (3 overlapping C), 24.79, 23.59. HRMS (ESI-TOF) m/z: Calcd for C$_{20}$H$_{28}$N$_3$O$_4$ [M+NH4]+374.2074; Found 374.2089.

8,9a-dimethyl-1-oxo-1,2,3,6,9,9a-hexahydro-5H-benzo[7]annulene-5,5-dicarbonitrile (Compound 6p). The compound has the structural formula:

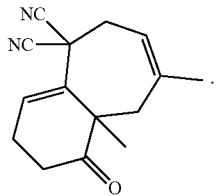 [SMILES: CC1=CCC(C#N)(C#N)C2=CCCC(=O)C2(C)C1]

Prepared from 5p by general procedure F with the following notes: Conditions: 80° C., overnight. Colorless oil, 0.031 g, 87%. $^1$H NMR (500 MHz, CDCl$_3$): δ 6.66 (dd, J=5.0, 4.0 Hz, 1H), 5.56 (dddd, J=7.6, 4.5, 2.1, 1.2 Hz, 1H), 3.06 (ddq, J=15.6, 6.2, 1.0 Hz, 1H), 2.87 (dddt, J=15.6, 6.1, 1.8, 0.9 Hz, 1H), 2.74 (dt, J=14.6, 6.8 Hz, 1H), 2.67-2.49 (m, 5H), 2.42 (ddd, J=14.3, 7.4, 6.7 Hz, 1H), 1.85 (q, J=1.3 Hz, 3H), 1.46 (s, 3H). $^{13}$C NMR (126 MHz, CDCl$_3$): δ 210.17, 142.35, 135.57, 131.31, 118.10, 115.80, 115.78, 51.36, 39.54, 38.78, 38.52, 34.87, 26.84, 24.14, 23.88. HRMS (ESI-TOF) m/z: Calcd for C$_{15}$H$_{17}$N$_2$O [M+H]$^+$ 241.1335; Found 241.1336.

methyl(4S,8aS)-7-(acetoxymethyl)-4-cyano-8a-methyl-1-oxo-1,2,4,5,8,8a-hexa-hydroazulene-4-carboxylate (Compound 6q). The compound has the structural formula:

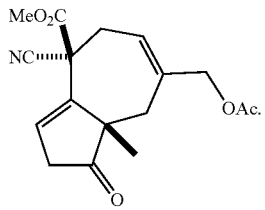 [SMILES: COC(=O)[C@@]1(C#N)CC=C(COC(C)=O)C[C@]2(C)C(=O)CC=C21]

Prepared from SI-11 by general procedure F with the following notes: Conditions: DCM, reflux, overnight. Beige solid, 1.32 g, 80%. $^1$H NMR (500 MHz, CDCl$_3$): δ 6.59 (s, 1H), 5.94 (d, J=7.1 Hz, 1H), 4.46 (d, J=13.1 Hz, 1H), 4.37 (d, J=13.0 Hz, 1H), 3.82 (s, 3H), 3.17-3.07 (m, 2H), 2.96 (dd, J=23.6, 2.5 Hz, 1H), 2.63 (dd, J=14.4, 5.9 Hz, 1H), 2.37 (d, J=14.8 Hz, 1H), 2.29 (d, J=14.8 Hz, 1H), 2.05 (s, 3H), 1.05 (s, 3H). $^{13}$C NMR (126 MHz, CDCl$_3$): δ 217.36, 170.63, 166.62, 142.71, 138.73, 128.14, 124.52, 118.13, 68.07, 54.17, 53.38, 49.76, 40.24, 36.12, 33.32, 21.82, 20.97. HRMS (ESI-TOF) m/z: Calcd for C$_{17}$H$_{18}$NaNO$_5$ [M+Na]$^+$340.1155; Found 340.1150.

(10aR,10bR)-2,5,7,8,9,10,10a,10b-octahydrobenzo[e]azulene-4,4(1H)-dicarbonitrile (Compound 8c). The compound has the structural formula:

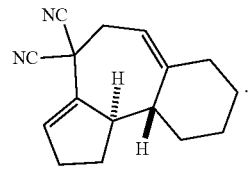

$^1$H NMR (500 MHz, CDCl$_3$): δ 6.28 (dq, J=2.6, 1.4 Hz, 1H), 5.43-5.37 (m, 1H), 3.07 (ddt, J=14.7, 5.1, 2.0 Hz, 1H), 2.92-2.84 (m, 1H), 2.60 (dd, J=14.7, 8.9 Hz, 1H), 2.54-2.45 (m, 1H), 2.40-2.32 (m, 1H), 2.26-2.14 (m, 2H), 2.06-1.92 (m, 3H), 1.85-1.70 (m, 3H), 1.45-1.28 (m, 2H), 1.19 (qd, J=12.4, 3.4 Hz, 1H). $^{13}$C NMR (126 MHz, CDCl$_3$): δ 150.17, 138.41, 135.90, 115.91, 115.77, 112.61, 48.91, 47.28, 37.99, 36.66, 33.56, 33.37, 30.58, 30.58, 28.13, 25.89. HRMS (ESI-TOF) m/z: Calcd for C$_{16}$H$_{18}$NaN$_2$ [M+Na]$^+$261.1362; Found 261.1374.

9a-methyl-1,2,3,6,9,9a-hexahydro-5H-benzo[7]annulene-5,5-dicarbonitrile (Compound 9d). The compound has the structural formula:

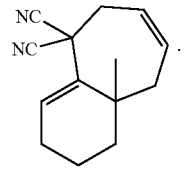

$^1$H NMR (500 MHz, CDCl$_3$): δ 6.39 (1H, t, J=3.9 Hz), 6.09-5.98 (1H, m), 5.81-5.72 (1H, m), 3.15-3.06 (1H, m), 2.93 (1H, ddt, J=16.0, 6.4, 1.1 Hz), 2.36 (1H, dd, J=16.5, 5.4 Hz), 2.32-2.23 (2H, m), 2.20-2.11 (1H, m), 1.81-1.59 (4H, m), 1.51 (1H, ddd, J=13.1, 4.7, 3.4 Hz), 1.32 (3H, s). $^{13}$C NMR (126 MHz, CDCl$_3$): 135.8, 133.2, 132.0, 123.6, 116.4, 116.2, 41.0, 40.4, 39.9, 38.7, 38.5, 26.4, 25.9, 17.6. HRMS (ESI-TOF) m/z: Calcd for C$_{14}$H$_{17}$N$_2$[M+H]$^+$213.1383; Found 213.1383.

9a-methyl-9-oxo-1,2,3,6,9,9a-hexahydro-5H-benzo[7]annulene-5,5-dicarbonitrile (Compound 10c). The compound has the structural formula:

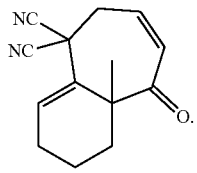

¹H NMR (500 MHz, CDCl₃): δ 6.41 (dd, J=4.3, 3.5 Hz, 1H), 6.23 (dt, J=12.5, 1.4 Hz, 1H), 6.17 (dt, J=12.5, 4.5 Hz, 1H), 3.39-3.29 (m, 1H), 3.01 (ddd, J=17.7, 4.4, 1.6 Hz, 1H), 2.37-2.26 (m, 1H), 2.26-2.14 (m, 1H), 1.88 (td, J=11.9, 3.1 Hz, 1H), 1.84-1.74 (m, 1H), 1.72-1.62 (m, 1H), 1.58 (s, 3H), 1.56-1.50 (m, 1H). ¹³C NMR (126 MHz, CDCl₃): δ 203.45, 133.71, 133.07, 132.02, 131.73, 115.25, 114.37, 52.06, 43.18, 39.46, 36.60, 25.48, 22.60, 17.60. HRMS (ESI-TOF) m/z: Calcd for $C_{14}H_{14}N_2NaO$ [M+Na]⁺249.0998; Found 249.1005.

7-methylene-6,7,8,8a-tetrahydro-1H-spiro[naphthalene-2,2'-[1.3]dioxolane]-5,5(3H)-dicarbonitrile (Compound 11b). The compound has the structural formula:

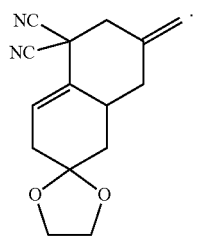

¹H NMR (500 MHz, CDCl₃): δ 6.23 (1H, td, J=4.1, 1.7 Hz), 5.13-5.00 (2H, m), 4.05-3.89 (4H, m), 2.99 (1H, dd, J=13.0, 1.9 Hz), 2.74-2.58 (2H, m), 2.47-2.33 (3H, m), 2.09 (1H, td, J=12.8, 1.7 Hz), 2.06-2.00 (1H, m), 1.60 (1H, ddd, J=13.5, 7.5, 1.2 Hz). ¹³C NMR (126 MHz, CDCl₃): δ 137.9, 129.2, 126.1, 115.8, 114.1, 113.7, 106.5, 64.6, 64.5, 44.9, 40.7, 40.6, 37.8, 35.6, 35.0. HRMS (ESI-TOF) m/z: Calcd for $C_{15}H_{16}N_2NaO_2$ [M+Na]⁺279.1104; Found 279.1093.

ethyl(3R,5aS,11aS)-10,10-dicyano-3,5,7,8,10,11-hexahydro-3,11a-epoxydi-benzo[a,d][7]annulene-5a(6H)-carboxylate (Compound 14a). The compound has the structural formula:

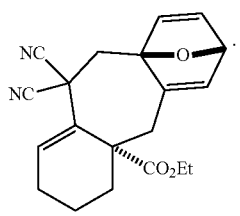

¹H NMR (500 MHz, CDCl₃): δ 6.51 (d, J=5.3 Hz, 1H), 6.48 (d, J=5.6 Hz, 1H), 5.24 (s, 1H), 4.99 (s, 2H), 4.47-4.29 (m, 2H), 3.15 (d, J=14.5 Hz, 1H), 2.78 (t, J=16.2 Hz, 2H), 2.46 (s, 1H), 2.28 (ddd, J=27.7, 12.0, 6.3 Hz, 2H), 2.14 (d, J=12.3 Hz, 1H), 1.97-1.84 (m, 1H), 1.59-1.48 (m, 1H), 1.42 (t, J=7.2 Hz, 4H). ¹³C NMR (126 MHz, CDCl₃): δ 166.9, 145.7, 137.0, 136.3, 135.9, 135.3, 115.0, 114.8, 108.7, 85.5, 82.5, 62.1, 45.2, 38.0, 37.4, 33.2, 28.4, 27.3, 20.3, 13.9. HRMS (ESI-TOF) m/z: Calcd for $C_{20}H_{20}N_2NaO_3$ [M+Na]+ 359.1372; Found 359.1393.

ethyl(3aS,6R,8aS)-10,10-dicyano-2,3,4,6,9,10-hexahydro-3aH-6,8a-epoxy-benzo[f]azulene-3a-carboxylate (Compound 14b). The compound has the structural formula:

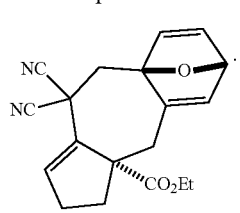

¹H NMR (500 MHz, CDCl₃): δ 6.66 (d, J=5.6 Hz, 1H), 6.60 (d, J=5.7 Hz, 1H), 5.34 (d, J=1.3 Hz, 1H), 5.18 (s, 1H), 5.17 (s, 1H), 4.63-4.49 (m, 2H), 3.33 (d, J=14.8 Hz, 1H), 3.24-3.12 (m, 1H), 2.96 (dd, J=9.8, 3.3 Hz, 2H), 2.91 (d, J=14.8 Hz, 1H), 2.66-2.55 (m, 1H), 2.25 (d, J=11.9 Hz, 1H), 2.00 (dq, J=19.6, 9.9 Hz, 1H), 1.60 (dd, J=12.6, 5.5 Hz, 4H). ¹³C NMR (126 MHz, CDCl₃): δ 163.64, 145.96, 140.87, 137.60, 136.61, 136.30, 114.08, 113.63, 106.72, 85.63, 82.42, 77.27, 77.02, 76.77, 61.76, 48.01, 47.29, 37.65, 33.04, 30.54, 28.75, 13.92. HRMS (ESI-TOF) m/z: Calcd for $C_{19}H_{16}N_2NaO_3$ [M+Na]+345.1215; Found 345.1216.

7,8-dihydroxy-3,6,7,8,9,9a-hexahydrospiro[benzo[7]annulene-2,2'-[1,3]dioxolane]-5,5(1H)-dicarbonitrile (Compound 15a). The compound has the structural formula:

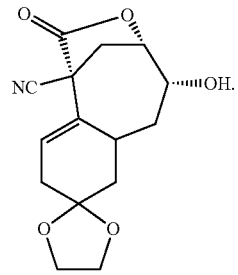 [SMILES: N#C[C@]12C[C@H](OC1=O)[C@H](O)CC1CC3(CC=C12)OCCO3]

¹H NMR (500 MHz, DMSO-d6): δ 5.99-5.69 (1H, m), 5.02 (1H, d, J=4.7 Hz), 4.67 (1H, d, J=8.8 Hz), 3.78-3.55 (6H, dtd, J=11.2, 4.7, 1.6 Hz), 2.91 (1H, dd, J=14.0, 9.2 Hz), 2.79 (1H, d, J=13.8 Hz), 2.31 (1H, m), 1.84 (2H, ddd, J=13.0, 5.8, 1.4 Hz), 1.63 (1H, dd, J=14.8, 4.9 Hz), 1.43 (1H, dd, J=13.3, 10.7 Hz), 1.30 (1H, dd, J=14.5, 11.6 Hz). ¹³C NMR (126 MHz, DMSO-d6): δ 172.1, 133.0, 127.0, 118.9, 106.1, 82.8, 71.6, 63.9, 63.8, 47.9, 39.8, 36.7, 35.5, 32.5, 31.8. HRMS (ESI-TOF) m/z: Calcd for $C_{15}H_{18}NO_3$ [M+H]+ 292.1185; Found 292.1182.

(5,5-dicyano-2-oxo-2,3,5,6,9,9a-hexahydro-1H-benzo[7]annulen-9-yl)methyl acetate (Compound 15b). The compound has the structural formula:

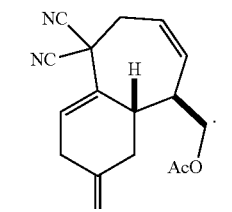

¹H NMR (500 MHz, CDCl₃): δ 6.47 (t, J=3.7 Hz, 1H), 5.78-5.73 (m, 2H), 4.16 (qd, J=11.7, 4.0 Hz, 2H), 3.22-3.16 (m, 2H), 3.13 (dd, J=23.0, 4.6 Hz, 1H), 2.98 (dd, J=22.9, 2.9 Hz, 1H), 2.88-2.81 (m, 1H), 2.74 (t, J=3.2 Hz, 2H), 2.32 (dd, J=10.4, 4.4 Hz, 1H), 2.08 (s, 3H). ¹³C NMR (126 MHz, CDCl₃): δ 205.88, 170.64, 136.03, 132.84, 129.53, 122.49, 114.82, 114.72, 63.62, 45.04, 43.09, 40.61, 39.26, 35.64, 34.06, 20.95. HRMS (ESI-TOF) m/z: Calcd for $C_{16}H_{16}N_2NaO_3$ [M+Na]+284.32; Found 307.1053.

8a-methyl-1-oxo-2,5,6,7,8,8a-hexahydroazulene-4,4 (1H)-dicarbonitrile (Compound 15c). The compound has the structural formula:

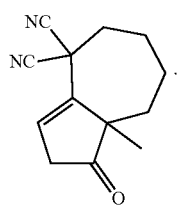 [SMILES: CC12CCCCC(C#N)(C#N)C1=CCC2=O]

¹H NMR (500 MHz, CDCl₃): δ 6.61 (t, J=2.5 Hz, 1H), 3.19 (dd, J=23.2, 2.1 Hz, 1H), 2.93 (dd, J=23.1, 2.8 Hz, 1H), 2.65 (ddd, J=13.7, 5.4, 3.3 Hz, 1H), 2.24 (ddt, J=14.8, 8.1, 1.3 Hz, 1H), 2.10-2.02 (m, 1H), 1.97-1.88 (m, 1H), 1.86-1.79 (m, 1H), 1.75 (dddd, J=15.2, 10.2, 5.0, 2.8 Hz, 1H), 1.59 (ddd, J=15.0, 10.7, 1.8 Hz, 1H), 1.36 (s, 3H), 1.02 (dtt, J=14.9, 10.7, 2.2 Hz, 1H). ¹³C NMR (126 MHz, CDCl₃): δ 215.60, 141.19, 127.98, 115.01, 113.86, 56.47, 42.53, 40.60, 37.84, 34.74, 26.61, 24.68, 23.61. HRMS (ESI-TOF) m/z: Calcd for $C_{13}H_{18}N_3O$ [M+NH4]+232.1444; Found 232.1441.

8a-methyl-1-oxo-1,2,4,5,8,8a-hexahydroazulene-4-carbonitrile (Compound 15d). The compound has the structural formula:

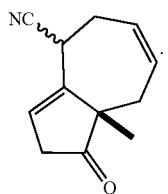

(trans)—diastereomer: ¹H NMR (500 MHz, CDCl₃): δ 6.30 (p, J=1.9 Hz, 1H), 5.98-5.89 (m, 2H), 3.33 (d, J=11.9 Hz, 1H), 3.07-2.93 (m, 2H), 2.69 (dd, J=14.9, 7.9 Hz, 1H), 2.43-2.34 (m, 1H), 2.27 (dd, J=14.8, 7.9 Hz, 1H), 2.08 (d, J=14.4 Hz, 1H), 1.06 (s, 3H). ¹³C NMR (126 MHz, CDCl₃): δ 218.72, 145.68, 131.05, 129.09, 121.34, 119.34, 52.86, 40.21, 34.76, 32.28, 31.14, 19.18. HRMS (ESI-TOF) m/z: Calcd for $C_{12}H_{13}NNaO$ [M+Na]+210.0889; Found 210.0897. (cis)—diastereomer: ¹H NMR (500 MHz, CDCl₃): δ 6.11-6.01 (m, 2H), 6.01 (s, 1H), 3.71 (td, J=3.6, 1.3 Hz, 1H), 3.07-2.97 (m, 1H), 2.93-2.83 (m, 1H), 2.69-2.60 (m, 1H), 2.40-2.31 (m, 2H), 2.13-2.05 (m, 1H), 1.32 (s, 3H). ¹³C NMR (126 MHz, CDCl₃): δ 218.48, 145.36, 131.99, 128.96, 124.67, 119.56, 53.60, 40.03, 34.27, 32.62, 30.26, 20.98. HRMS (ESI-TOF) m/z: Calcd for $C_{12}H_{13}NNaO$ [M+Na]+210.0889; Found 210.0882.

8a-methyl-1-oxo-1,2,8,8a-tetrahydroazulene-4-carbonitrile (Compound 15e). The compound has the structural formula:

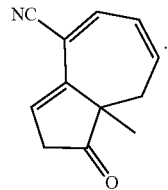

¹H NMR (500 MHz, CDCl₃): δ 6.57 (ddt, J=8.1, 1.7, 0.8 Hz, 1H), 6.53 (t, J=2.9 Hz, 1H), 6.31 (ddd, J=11.8, 8.6, 3.4 Hz, 1H), 6.10 (ddd, J=11.3, 7.9, 3.2 Hz, 1H), 3.33-3.22 (m, 1H), 3.04 (dd, J=24.7, 3.0 Hz, 1H), 2.69 (dd, J=17.3, 8.6 Hz, 1H), 2.19-2.11 (m, 1H), 1.06 (s, 3H). ¹³C NMR (126 MHz, CDCl₃): δ 217.35, 144.66, 138.74, 135.84, 127.91, 125.67, 118.42, 111.39, 50.89, 41.15, 35.57, 21.12. HRMS (ESI-TOF) m/z: Calcd for $C_{12}H_{16}N_2O$ [M+NH4]+203.1179; Found 203.1182.

(1S*,8aS*)-1-hydroxy-8a-methyl-2,5,8,8a-tetrahydroazulene-4,4(1H)-dicarbonitrile (Compound 15f). The compound has the structural formula:

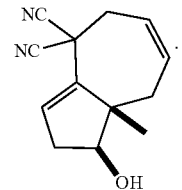 [SMILES: C[C@]12CC=CCC(C#N)(C#N)C1=CC[C@@H]2O]

¹H NMR (500 MHz, CDCl₃): δ 6.21-6.15 (m, 2H), 5.97-5.91 (m, 1H), 4.04 (dd, J=8.9, 7.6 Hz, 1H), 3.01-2.94 (m, 1H), 2.84 (ddd, J=14.5, 6.1, 1.7 Hz, 1H), 2.65 (ddd, J=16.4, 7.6, 3.3 Hz, 1H), 2.36 (dd, J=14.6, 7.9 Hz, 1H), 2.29-2.20 (m, 2H), 1.17 (s, 3H). ¹³C NMR (126 MHz, CDCl₃): δ 140.61, 135.23, 130.59, 125.00, 115.16, 114.56, 80.71, 50.00, 36.93, 36.40, 35.79, 35.75, 16.51. HRMS (ESI-TOF) m/z: Calcd for $C_{13}ClH_{14}N_2O$ [M+Cl]− 249.0800; Found 249.0790.

methyl(4S,8aS)-7-(acetoxymethyl)-8a-methyl-1-oxo-1,2,4,5,8,8a-hexahydro-azulene-4-carboxylate (Compound 15g). The compound has the structural formula:

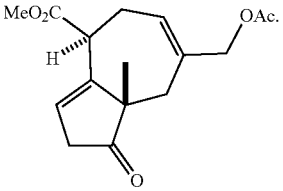

¹H NMR (500 MHz, CDCl₃): δ 6.07-6.00 (m, 1H), 5.95 (t, J=2.2 Hz, 1H), 4.48-4.38 (m, 3H), 3.67 (s, 3H), 3.55 (dd, J=6.4, 4.1 Hz, 1H), 3.03 (dd, J=23.3, 2.0 Hz, 1H), 2.87 (dd, J=23.4, 2.4 Hz, 1H), 2.75 (ddd, J=14.4, 8.2, 6.4 Hz, 1H), 2.25 (d, J=3.2 Hz, 2H), 2.24-2.21 (m, 1H), 2.05 (s, 3H), 1.04 (s, 3H). ¹³C NMR (126 MHz, CDCl₃): δ 220.10, 172.86, 170.90, 147.73, 135.84, 129.08, 124.48, 69.37, 53.44, 52.16, 47.07, 40.38, 36.35, 27.99, 21.11, 21.01. HRMS (ESI-TOF) m/z: Calcd for $C_{15}H_{20}O_5Na$ [M+Na]+315.1210; Found 315.1211.

(3aR,8aS)-7-(hydroxymethyl)-8a-methyl-1-oxo-1,3a,4,5,8,8a-hexahydroazulene-4-carbonitrile (Compound 15h). The compound has the structural formula:

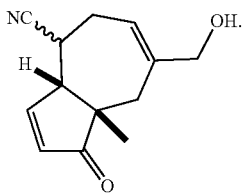 [SMILES: C[C@]12CC(CO)=CCC(C#N)[C@H]1C=CC2=O]

HRMS (ESI-TOF) m/z: Calcd for $C_{13}H_{15}NO_2Na$ [M+Na]+240.0995; Found 240.1003.

4a-ethyl 9-methyl 9-cyano-2,3,4,5,8,9-hexahydro-4aH-benzo[7]annulene-4a,9-dicarboxylate (Compound 15i). The compound has the structural formula:

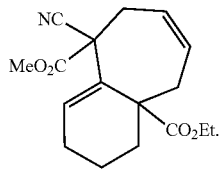

$^1$H NMR (500 MHz, CDCl$_3$): δ 6.22 (dd, J=4.6, 3.4 Hz, 1H), 5.69-5.61 (m, 1H), 5.51-5.44 (m, 1H), 4.22-4.13 (m, 2H), 3.80 (s, 3H), 3.08-3.00 (m, 1H), 2.94 (dd, J=17.2, 7.4 Hz, 1H), 2.72 (dd, J=17.4, 6.6 Hz, 1H), 2.40-2.33 (m, 1H), 2.31-2.22 (m, 1H), 2.20-2.11 (m, 1H), 2.03-1.97 (m, 1H), 1.72-1.65 (m, 2H), 1.54-1.45 (m, 1H), 1.26 (t, J=7.1 Hz, 3H). $^{13}$C NMR (126 MHz, CDCl$_3$): δ 175.78, 169.13, 133.51, 132.57, 129.77, 124.46, 120.16, 61.32, 53.97, 53.43, 50.92, 37.76, 37.35, 36.16, 25.68, 18.38, 14.26. HRMS (ESI-TOF) m/z: Calcd for $C_{17}H_{22}NO_4$ [M+H]+ 304.1543; Found 304.1544.

9-allyl 4a-ethyl 9-cyano-2,3,4,5,8,9-hexahydro-4aH-benzo[7]annulene-4a,9-dicarboxylate (15i) (Compound 15l). The compound has the structural formula:

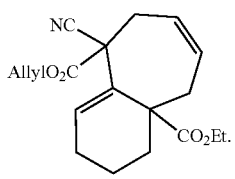

(major diastereomer): $^1$H NMR (500 MHz, CDCl$_3$): δ 6.23 (1H, dd, J=4.7, 3.1 Hz), 5.87 (1H, ddt, J=17.0, 10.3, 5.6 Hz), 5.62 (1H, ddt, J=12.4, 6.4, 2.9 Hz), 5.51-5.42 (1H, m), 5.36 (1H, d, J=17.2, 1.4 Hz), 5.26 (1H, dq, J=10.6, 1.3 Hz), 4.66 (2H, d, J=5.7 Hz), 4.23-4.09 (2H, m), 3.09-2.99 (1H, m), 2.95 (1H, dd, J=17.3, 7.3 Hz), 2.69 (1H, dd, J=17.5, 6.8 Hz), 2.40-2.31 (1H, m), 2.29-2.21 (1H, m), 2.14 (1H, dddd, J=18.7, 10.3, 6.7, 3.1 Hz), 2.01-1.95 (1H, m), 1.72-1.61 (2H, m), 1.53-1.42 (1H, m), 1.24 (3H, t, J=7.1 Hz). $^{13}$C NMR (126 MHz, CDCl$_3$): δ 175.6, 168.0, 133.4, 132.3, 130.8, 129.5, 124.3, 119.9, 119.0, 67.1, 61.1, 53.4, 50.7, 37.6, 37.2, 35.9, 25.5, 18.2, 14.1. (minor diastereomer): $^1$H NMR (500

MHz, CDCl$_3$): δ 6.17 (1H, t, J=3.9 Hz), 5.98-5.88 (1H, m), 5.79 (1H, ddt, J=12.7, 6.6, 3.3 Hz), 5.63-5.56 (1H, m), 5.40 (1H, dd, J=17.3, 1.4 Hz), 5.28 (1H, dd, J=10.6, 1.2 Hz), 4.71 (2H, ddt, J=5.6, 2.8, 1.4 Hz), 4.19 (1H, dq, J=10.7, 7.1 Hz), 4.07 (1H, dq, J=10.9, 7.1 Hz), 3.13-3.05 (1H, m), 2.77 (1H, dd, J=17.6, 6.2 Hz), 2.61-2.52 (1H, m), 2.48 (1H, dd, J=17.1, 7.9 Hz), 2.22-2.11 (2H, m), 1.97 (1H, ddd, J=12.8, 6.3, 2.8 Hz), 1.71-1.58 (3H, m), 1.57-1.43 (2H, m), 1.25-1.20 (3H, m). $^{13}$C NMR (126 MHz, CDCl$_3$): δ 6 175.5, 167.7, 133.8, 132.9, 130.9, 130.6, 123.4, 120.1, 119.1, 66.9, 61.1, 53.9, 50.1, 37.8, 37.6, 33.1, 25.6, 17.7, 14.0. HRMS (ESI-TOF) m/z: Calcd for $C_{19}H_{24}NO_4$ [M+H]+ 330.1700; Found 330.1703.

Ethyl(4aR,9R)-9-carbamoyl-9-cyano-2,3,4,5,8,9-hexahydro-4aH-benzo[7]annulene-4a-carboxylate (Compound 15k). The compound has the structural formula:

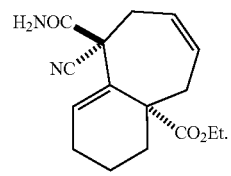

$^1$H NMR (500 MHz, CDCl$_3$): δ 6.70 (s, 1H), 5.90 (dd, J=5.0, 2.8 Hz, 1H), 5.75-5.64 (m, 1H), 5.58 (s, 1H), 5.56-5.50 (m, 1H), 4.34-4.17 (m, 2H), 3.26 (ddq, J=16.7, 5.2, 2.6 Hz, 1H), 2.99-2.80 (m, 2H), 2.34 (dd, J=16.7, 7.8 Hz, 1H), 2.22-2.13 (m, 1H), 2.13-2.01 (m, 2H), 1.75-1.63 (m, 2H), 1.47-1.37 (m, 1H), 1.31 (t, J=7.1 Hz, 3H). $^{13}$C NMR (126 MHz, CDCl$_3$): δ 176.38, 169.10, 135.60, 130.22, 126.65, 125.28, 121.91, 61.73, 52.21, 49.98, 39.68, 35.77, 33.95, 25.40, 18.81, 14.18. HRMS (ESI-TOF) m/z: Calcd for $C_{16}H_{21}N_2O_3$ [M+H]+ 289.1547; Found 289.1550.

(4aR,9S)-10,12-dioxo-3,4,5,8-tetrahydro-4a,9-(methanoiminomethano)benzo[7]annulene-9(2H)-carbonitrile (Compound 15l). The compound has the structural formula:

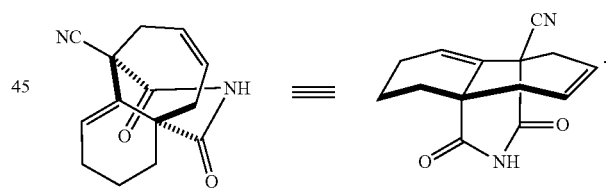

$^1$H NMR (500 MHz, CDCl$_3$): δ 8.02 (s, 1H), 6.48 (dd, J=4.6, 3.0 Hz, 1H), 5.98 (ddt, J=11.7, 8.4, 3.4 Hz, 1H), 5.80 (ddt, J=11.6, 8.6, 3.3 Hz, 1H), 3.22 (dd, J=14.9, 8.7 Hz, 1H), 2.68 (dq, J=14.9, 3.2 Hz, 1H), 2.60 (dq, J=14.9, 3.2 Hz, 1H), 2.52 (dd, J=15.0, 8.4 Hz, 1H), 2.28-2.16 (m, 3H), 1.88-1.80 (m, 2H), 1.79-1.68 (m, 1H). $^{13}$C NMR (126 MHz, CDCl$_3$): δ 174.31, 166.57, 132.13, 131.34, 129.04, 126.38, 116.97, 51.55, 44.49, 41.15, 40.93, 33.15, 25.36, 18.07. HRMS (ESI-TOF) m/z: Calcd for $C_{14}H_{15}N_2O_2$ [M+H]+ 243.1128; Found 243.1132.

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method of synthesizing a terpenoid framework, comprising:
providing a γ-allyl Knoevenagel adduct or a quasi γ-allyl Knoevenagel adduct having a structure represented by a formula:

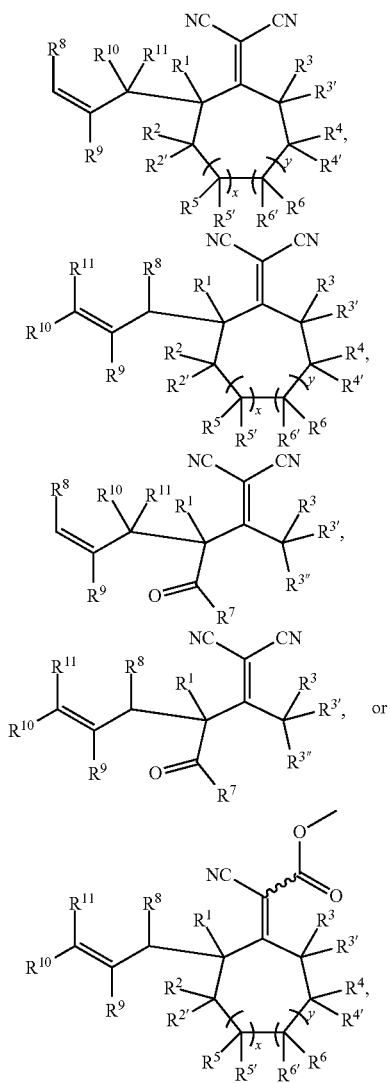

wherein x and y are independently 0 or 1;
wherein $R_7$ is $C_1$ to $C_6$ alkyl or $C_1$ to $C_6$ alkoxy;
wherein $R^1$, $R^2$, $R^{2'}$, $R^3$, $R^{3'}$, $R^{3''}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_6$ to $C_{12}$ alkatrienyl, $C_3$ to $C_8$ cycloalkanyl, $C_3$ to $C_8$ cycloalkenyl, $C_1$ to $C_{12}$ alkoxy, phenoxy, acetoxy, or phenyl;
wherein one or more of $R^2$ with $R^{2'}$, $R^3$ with $R^{3'}$, $R^4$ with $R^{4'}$, $R^5$ with $R^{5'}$, and $R^6$ with $R^{6'}$ is optionally combined as carbonyl, ethylenyl, $C_3$ to $C_8$ cycloalkyl, $C_3$ to $C_8$ cycloalkenyl, —O(CH$_2$)$_2$O—, or —O(CH$_2$)$_3$O—;
wherein one or more of $R^{2'}$ with $R^{5'}$, $R^{3'}$ with $R^{4'}$, $R^{4'}$ with $R^{6'}$, and $R^{5'}$ with $R^{6'}$ is optionally combined as a π-bond or a π-bond with $R^2$ with $R^5$, $R^3$ with $R^4$, $R^4$ with $R^6$, and/or $R^5$ with $R^6$ combined as an aromatic ring, $C_5$ or $C_6$ cycloalkene, or $C_5$ or $C_6$ cycloalkadiene, and where each of $R^2$, $R^3$, $R^4$, $R^5$, and $R^6$ is combined only once;
wherein one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or
wherein $R^4R^{4'}C$, $R^5R^{5'}C$ or $R^6R^{6'}C$ are optionally replaced with an oxygen; and wherein any of the previous said alkyl, alkadienyl, alkatrienyl, cycloalkyl, cycloalkenyl, alkoxy, phenoxy, aromatic ring, and alkylene chain is optionally substituted with one or more $C_1$ to $C_4$ alkyl, $C_1$ to $C_4$ alkoxy, $C_3$ to $C_6$ cycloalkyl, $C_3$ to $C_6$ cycloalkenyl, phenyl, acetyl, or nitro groups; and
wherein $R^8$ is H, phenyl or the oxygen of an oxo group, $R^9$, $R^{10}$, and $R^{11}$ are independently H, CH$_2$X, $C_1$ to $C_{12}$ alkyl, or phenyl, or wherein $R^9$ and $R^{10}$ are combined as a $C_5$ or $C_6$ cycloalkene or phenyl, wherein the $C_1$ to $C_{12}$ alkyl of $R^9$-$R^{11}$, the three previous phenyl, or $C_5$ or $C_6$ cycloalkene of $R^9$ and $R^{10}$ are optionally further substituted with one or more Br, Cl, I, $C_1$ to $C_4$ alkoxy, or where two adjacent carbons are substituted by methylenedioxy, wherein X is a leaving group selected from acetoxy, t-butyloxycarbonoxy, Cl, Br, I, trifluroacetoxy, or tosyl,
reacting the γ-allyl Knoevenagel adduct or the quasi γ-allyl Knoevenagel adduct with an allyl comprising electrophile to form an α,γ-diallyl Knoevenagel adduct or quasi α,γ-diallyl Knoevenagel adduct; and
catalyzing a ring-closure metathesis of the α,γ-diallyl Knoevenagel adduct or quasi α,γ-diallyl Knoevenagel adduct thereby forming a compound with a terpenoid framework.

2. The method of claim 1, wherein the γ-allyl Knoevenagel adduct or the quasi γ-allyl Knoevenagel adduct has a structure represented by a formula:

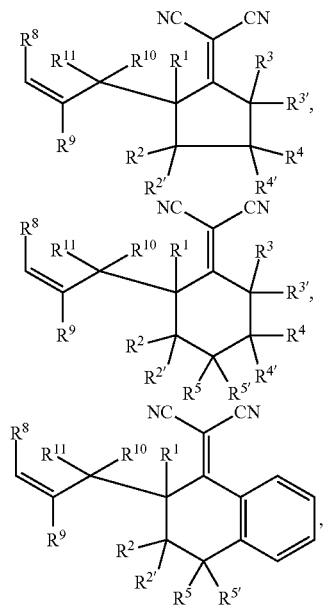

3. The method of claim 1, wherein the γ-allyl Knoevenagel adduct or the quasi γ-allyl Knoevenagel adduct has a structure represented by a formula:

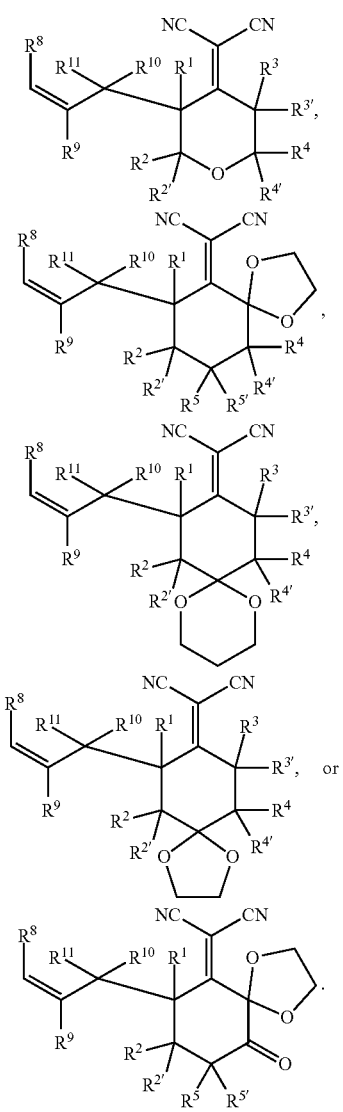

4. The method of claim 1, wherein providing the γ-allyl Knoevenagel adduct or the quasi γ-allyl Knoevenagel adduct comprises reacting a ketone having a structure represented by a formula:

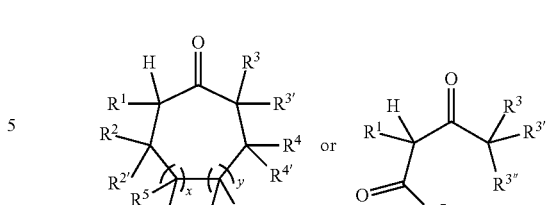

with an allyl electrophile having a structure represented by a formula:

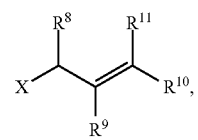

wherein X is a leaving group selected from acetoxy, t-butyloxycarbonoxy, Cl, Br, I, trifluroacetoxy, or tosyl.

5. The method of claim 4, wherein the ketone has a structure represented by a formula:

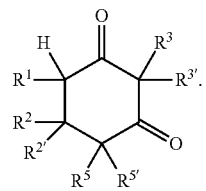

6. The method of claim 5, wherein the ketone has a structure represented by a formula:

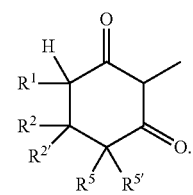

7. The method of claim 1, wherein providing the γ-allyl Knoevenagel adduct or the quasi γ-allyl Knoevenagel adduct comprises reacting a ketone having a structure represented by a formula:

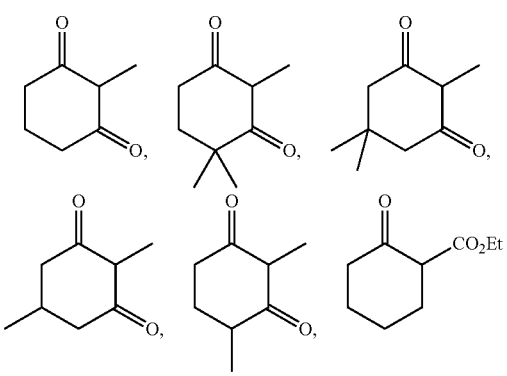

-continued

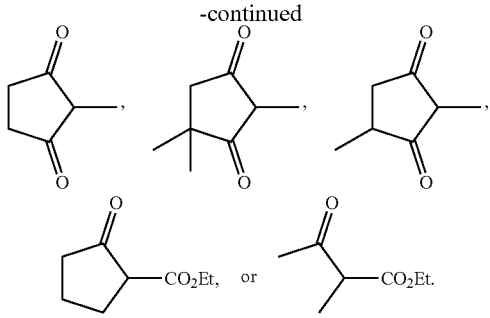

with an allyl electrophile having a structure represented by a formula:

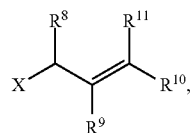

wherein X is a leaving group selected from acetoxy, t-butyloxycarbonoxy, Cl, Br, I, trifluroacetoxy, or tosyl.

8. The method of claim 1, wherein providing the γ-allyl Knoevenagel adduct or the quasi γ-allyl Knoevenagel adduct comprises reacting a Knoevenagel adduct having a structure represented by a formula:

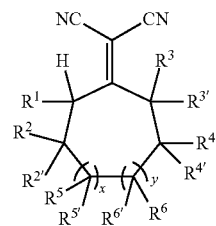

with an allyl electrophile having a structure represented by a formula:

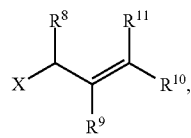

wherein X is a leaving group selected from acetoxy, t-butyloxycarbonoxy, Cl, Br, I, trifluroacetoxy, or tosyl.

9. The method of claim 8, wherein the Knoevenagel adduct has a structure represented by a formula:

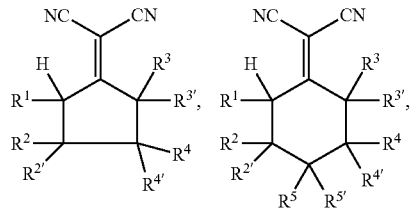

-continued

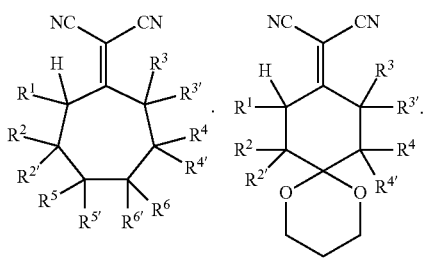

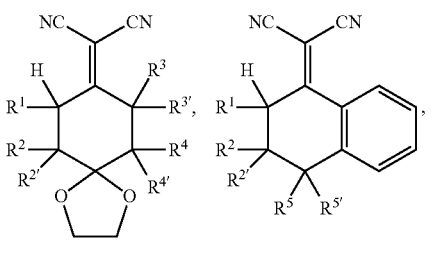

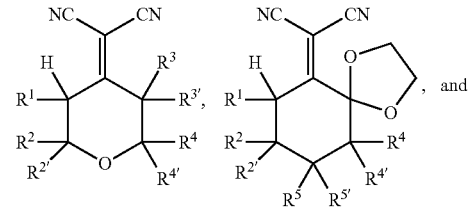

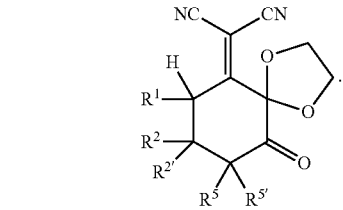

10. The method of claim 9, wherein the Knoevenagel adduct has a structure represented by a formula:

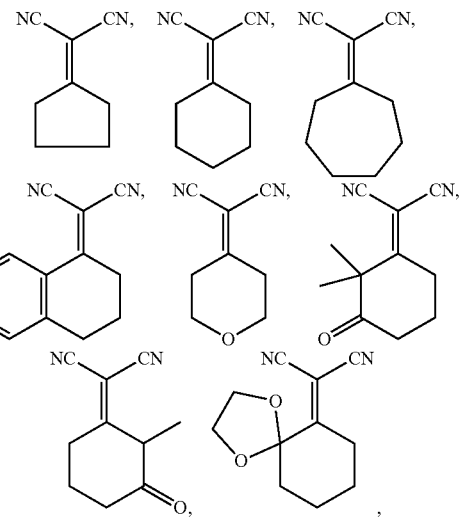

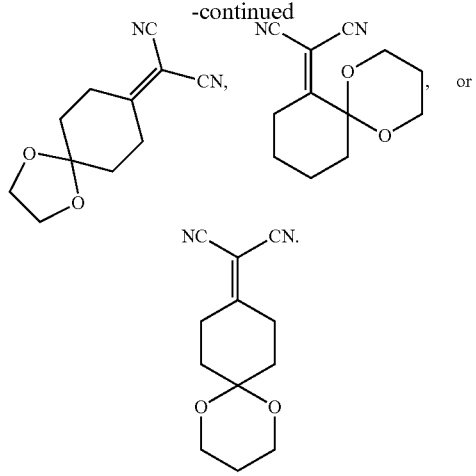

11. The method of claim 8, wherein the Knoevenagel adduct has a structure represented by a formula:

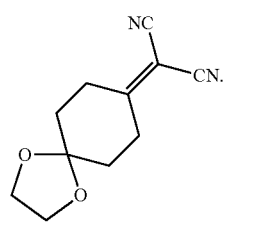 [SMILES: N#CC(C#N)=C1CCC2(CC1)OCCO2]

12. The method of claim 8, wherein X is acetoxy, t-butyloxycarbonoxy, or Br.

13. The method of claim 8, wherein the allyl electrophile has a structure represented by a formula:

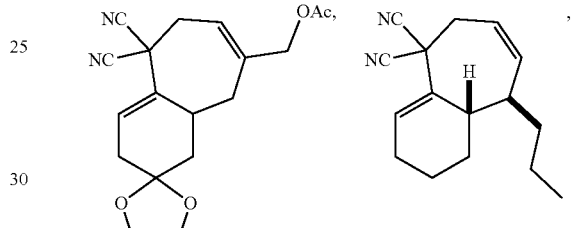

14. The method of claim 1, wherein the compound with a terpenoid framework has a structure represented by a formula:

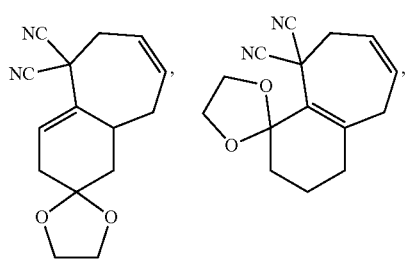

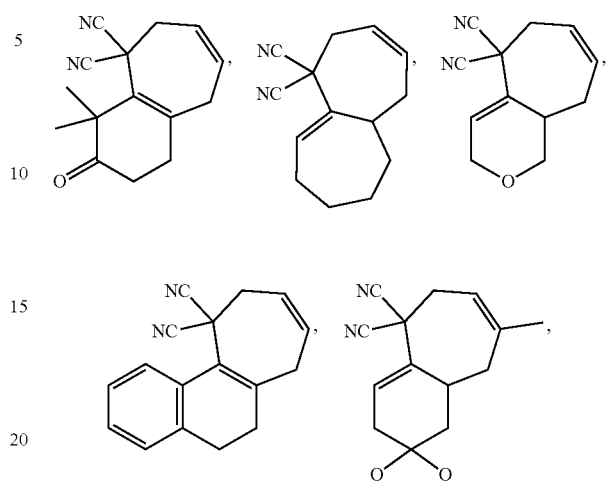

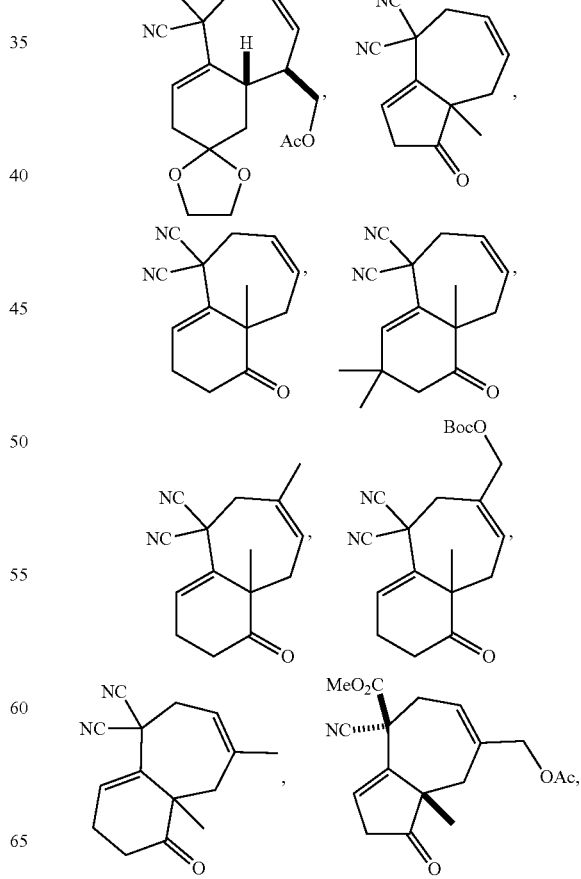

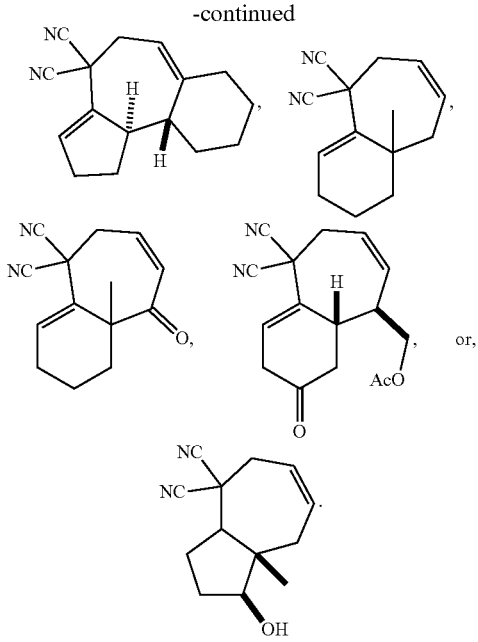

15. A γ-allyl Knoevenagel adduct or a quasi γ-allyl Knoevenagel adduct having a structure represented by a formula:

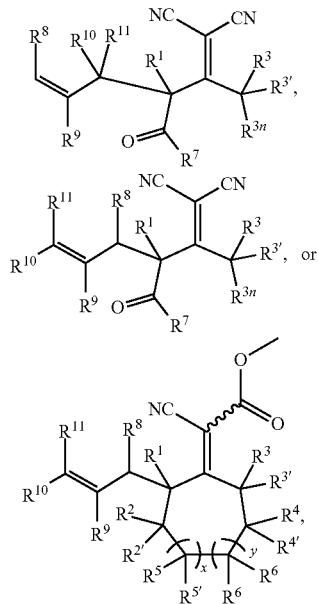

wherein x and y are independently 0 or 1;
wherein $R_7$ is $C_1$ to $C_6$ alkyl;
wherein $R^1$, $R^2$, $R^{2'}$, $R^3$, $R^{3'}$, $R^{3''}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_6$ to $C_{12}$ alkatrienyl, $C_3$ to $C_5$ cycloalkanyl, $C_3$ to $C_5$ cycloalkenyl, $C_1$ to $C_{12}$ alkoxy, phenoxy, acetoxy, or phenyl;
wherein one or more of $R^2$ with $R^{2'}$, $R^3$ with $R^{3'}$, $R^4$ with $R^{4'}$, $R^5$ with $R^{5'}$, and $R^6$ with $R^{6'}$ is optionally combined as carbonyl, ethylenyl, $C_3$ to $C_8$ cycloalkyl, $C_3$ to $C_8$ cycloalkenyl, $-O(CH_2)_2O-$, or $-O(CH_2)_3O-$;

wherein one or more of $R^{2'}$ with $R^{2'}$, $R^{3'}$ with $R^{4'}$, $R^{4'}$ with $R^{6'}$, and $R^{5'}$ with $R^{6'}$ is optionally combined as a π-bond or a π-bond with $R^2$ with $R^5$, $R^3$ with $R^4$, $R^4$ with $R^6$, and/or $R^5$ with $R^6$ combined as an aromatic ring, $C_5$ or $C_6$ cycloalkene, or $C_5$ or $C_6$ cycloalkadiene, and where each of $R^2$, $R^3$, $R^4$, $R^5$, and $R^6$ is combined only once;
wherein one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or wherein $R^4R^{4'}C$, $R^5R^{5'}C$ or $R^6R^{6'}C$ are optionally replaced with an oxygen; and wherein any of the previous said alkyl alkadienyl, alkatrienyl, cycloalkyl, cycloalkenyl, alkoxy, phenoxy, aromatic ring, and alkylene chain is optionally substituted with one or more $C_1$ to $C_4$ alkyl, $C_1$ to $C_4$ alkoxy, $C_3$ to $C_6$ cycloalkyl, $C_3$ to $C_6$ cycloalkenyl, phenyl, acetyl, or nitro groups; and
wherein $R^8$ is H, phenyl or the oxygen of an oxo group, $R^9$, $R^{10}$, and $R^{11}$ are independently H, $CH_2X$, $C_1$ to $C_{12}$ alkyl, or phenyl, or wherein $R^9$ and $R^{10}$ are combined as a $C_5$ or $C_6$ cycloalkene or phenyl, wherein X is a leaving group selected from acetoxy, t-butyloxycarbonoxy, Cl, Br, I trifluroacetoxy, or tosyl, wherein the $C_1$ to $C_{12}$ alkyl of $R^9$-$R^{11}$, the three previous phenyl, or $C_5$ or $C_6$ cycloalkene of $R^9$ and $R^{10}$ are optionally further substituted with one or more Br, Cl, I, $C_1$ to $C_4$ alkoxy, or where two adjacent carbons are substituted by methylenedioxy;
wherein at least one of $R^1$, $R^8$, $R^9$, $R^{10}$, and $R^{11}$ is present and is not H.

16. A γ-allyl Knoevenagel adduct or a quasi γ-allyl Knoevenagel adduct having a structure represented by a formula:

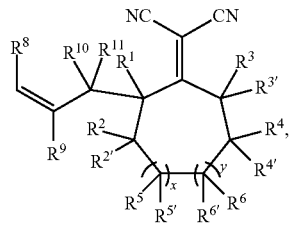

wherein x and y are independently 0 or 1;
wherein $R^1$, $R^2$, $R^{2'}$, $R^3$, $R^{3'}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_6$ to $C_{12}$ alkatrienyl, $C_3$ to $C_8$ cycloalkanyl, $C_3$ to $C_8$ cycloalkenyl, $C_1$ to $C_{12}$ alkoxy, phenoxy, acetoxy, or phenyl, wherein at least one of $R^2$, $R^{2'}$, $R^3$, $R^{3'}$, $R^4$, $R^{4'}$, $R^5$, $R^{5'}$, $R^6$, and $R^{6'}$ is present and is not H;
wherein one or more of $R^2$ with $R^{2'}$, $R^3$ with $R^{3'}$, $R^4$ with $R^{4'}$, $R^5$ with $R^{5'}$, and $R^6$ with R6' is optionally combined as carbonyl, ethylenyl, $C_3$ to $C_8$ cycloalkyl, $C_3$ to $C_8$ cycloalkenyl, $-O(CH_2)_2O-$, or $-O(CH_2)_3O-$;
wherein one or more of $R^{2'}$ with $R^5$, $R^{3'}$ with $R^{4'}$, $R^{4'}$ with $R^{6'}$, and $R^{5'}$ with $R^{6'}$ is optionally combined as a π-bond or a π-bond with $R^2$ with $R^5$, $R^3$ with $R^4$, $R^4$ with $R^6$, and/or $R^5$ with $R^6$ combined as an aromatic ring, $C_5$ or $C_6$ cycloalkene, or $C_5$ or $C_6$ cycloalkadiene, and where each of $R^2$, $R^3$, $R^4$, $R^5$, and $R^6$ is combined only once;

wherein one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or wherein $R^4R^{4'}C$, $R^5R^{5'}C$ or $R^6R^{6'}C$ are optionally replaced with an oxygen; and wherein any of the previous said alkyl alkadienyl, alkatrienyl, cycloalkyl, cycloalkenyl, alkoxy, phenoxy, aromatic ring, and alkylene chain is optionally substituted with one or more $C_1$ to $C_4$ alkyl, $C_1$ to $C_4$ alkoxy, $C_3$ to $C_6$ cycloalkyl, $C_3$ to $C_6$ cycloalkenyl, phenyl, acetyl, or nitro groups; and wherein $R^8$ is H, phenyl or the oxygen of an oxo group, $R^9$, $R^{10}$, and $R^{11}$ are independently H, $CH_2X$, $C_1$ to $C_{12}$ alkyl, or phenyl, or wherein $R^9$ and $R^{10}$ are combined as a $C_5$ or $C_6$ cycloalkene, wherein X is a leaving group selected from acetoxy, t-butyloxycarbonoxy, Cl, Br, I, trifluroacetoxy, or tosyl, wherein the $C_1$ to $C_{12}$ alkyl of $R^9$-$R^{11}$, the two previous phenyl, or $C_5$ or $C_6$ cycloalkene of $R^9$ and $R^{10}$ are optionally be further substituted with one or more Br, Cl, I, $C_1$ to $C_4$ alkoxy, or where two adjacent carbons are substituted by methylenedioxy.

17. The compound of claim 16 wherein the γ-allyl Knoevenagel adduct or the quasi γ-allyl Knoevenagel adduct has a structure represented by a formula:

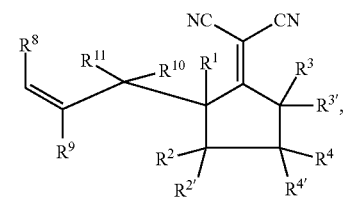

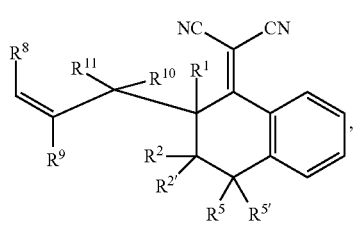

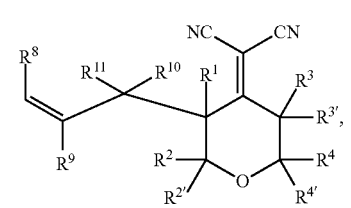

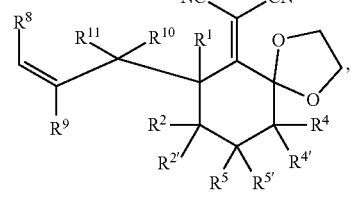

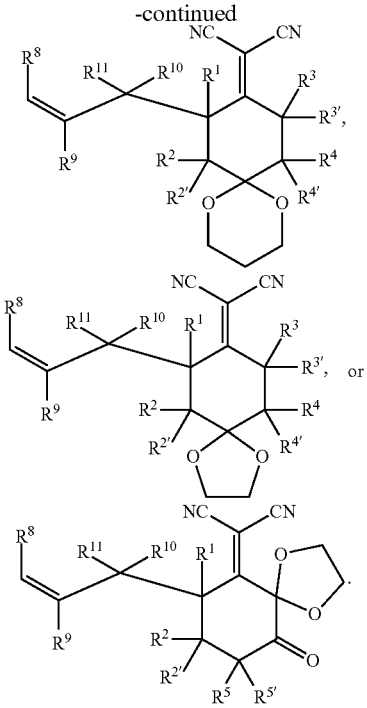

18. A γ-allyl Knoevenagel adduct or a quasi γ-allyl Knoevenagel adduct having a structure represented by a formula:

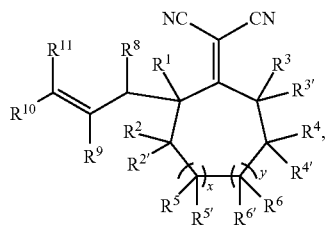

wherein x and y are independently 0 or 1;
wherein $R^1$, $R^2$, $R^{2'}$, $R^3$, $R^{3'}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_6$ to $C_{12}$ alkatrienyl, $C_3$ to $C_5$ cycloalkanyl, $C_3$ to $C_5$ cycloalkenyl, $C_1$ to $C_{12}$ alkoxy, phenoxy, acetoxy, or phenyl, wherein at least one of $R^2$, $R^{2'}$, $R^3$, $R^{3'}$, $R^4$, $R^{4'}$, $R^5$, $R^{5'}$, $R^6$, and $R^{6'}$ is present and is not H;
wherein one or more of $R^2$ with $R^{2'}$, $R^3$ with $R^{3'}$, $R^4$ with $R^{4'}$, $R^5$ with $R^{5'}$, and $R^6$ with $R6'$ is optionally combined as carbonyl, ethylenyl, $C_3$ to $C_8$ cycloalkyl, $C_3$ to $C_8$ cycloalkenyl, —O(CH$_2$)$_2$O—, or —O(CH$_2$)$_3$O—;
wherein one or more of $R^{2'}$ with $R^{5'}$, $R^{3'}$ with $R^{4'}$, $R^4$ with $R^{6'}$, and $R^{5'}$ with $R^{6'}$ is optionally combined as a π-bond or a π-bond with $R^2$ with $R^5$, $R^3$ with $R^4$, $R^4$ with $R^6$, and/or $R^5$ with $R^6$ combined as an aromatic ring, $C_5$ or $C_6$ cycloalkene, or $C_5$ or $C_6$ cycloalkadiene, and where each of $R^2$, $R^3$, $R^4$, $R^5$, and $R^6$ is combined only once;
wherein one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or wherein $R^4R^{4'}C$, $R^5R^{5'}C$ or $R^6R^{6'}C$ are optionally replaced with an oxygen; and wherein any of the previous said alkyl alkadienyl, alkatrienyl, cycloalkyl, cycloalkenyl, alkoxy, phenoxy, aromatic ring, and alkylene chain is optionally substituted with one or more $C_1$ to $C_4$ alkyl, $C_1$ to $C_4$ alkoxy, $C_3$ to $C_6$ cycloalkyl, $C_3$ to $C_6$ cycloalkenyl, phenyl, acetyl, or nitro groups; and wherein $R^8$ is phenyl or the oxygen of an oxo group, $R^9$, $R^{10}$, and $R^{11}$ are independently H, $CH_2X$, $C_1$ to $C_{12}$ alkyl, or phenyl, or wherein $R^9$ and $R^{10}$ are combined as a $C_5$ or $C_6$ cycloalkene, wherein X is a leaving group selected from acetoxy, t-butyloxycarbonoxy, Cl, Br, I, trifluroacetoxy, or tosyl, wherein the $C_1$ to $C_{12}$ alkyl of $R^9$-$R^{11}$, the two previous phenyl, or $C_5$ or $C_6$ cycloalkene of $R^9$ and $R^{10}$ are optionally be further substituted with one or more Br, Cl, I, $C_1$ to $C_4$ alkoxy, or where two adjacent carbons are substituted by methylenedioxy.

19. A γ-allyl Knoevenagel adduct or a quasi γ-allyl Knoevenagel adduct having a structure represented by a formula:

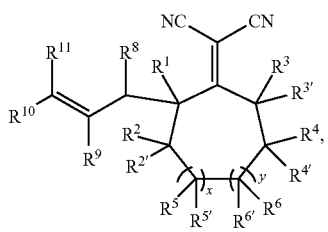

wherein x and y are independently 0 or 1;

wherein $R^1$, $R^2$, $R^{2'}$, $R^3$, $R^{3'}$, $R^4$, $R^{4'}$, $R^5$, $R^{5'}$, $R^6$, and $R^{6'}$ are independently H, linear or branched $C_1$ to $C_{12}$ alkyl, linear or branched $C_2$ to $C_{12}$ alkenyl, linear or branched $C_2$ to $C_{12}$ alkynyl, linear or branched $C_4$ to $C_{12}$ alkadienyl, linear or branched $C_6$ to $C_{12}$ alkatrienyl, $C_3$ to $C_8$ cycloalkanyl, $C_3$ to $C_8$ cycloalkenyl, $C_1$ to $C_{12}$ alkoxy, phenoxy, acetoxy, or phenyl, wherein at least one of $R^2$, $R^{2'}$, $R^3$, $R^{3'}$, $R^4$, $R^{4'}$, $R^5$, $R^{5'}$, $R^6$, and $R^{6'}$ is present and is not H;

wherein one or more of $R^2$ with $R^{2'}$, $R^3$ with $R^{3'}$, $R^4$ with $R^{4'}$, $R^5$ with $R^{5'}$, and $R^6$ with $R6'$ is optionally combined as carbonyl, ethylenyl, $C_3$ to $C_8$ cycloalkyl, $C_3$ to $C_8$ cycloalkenyl, —$O(CH_2)_2O$—, or —$O(CH_2)_3O$—;

wherein one or more of $R^{2'}$ with $R^{5'}$, $R^{3'}$ with $R^{4'}$, $R^{4'}$ with $R^{6'}$, and $R^{5'}$ with $R^{6'}$ is optionally combined as a π-bond or a π-bond with $R^2$ with $R^5$, $R^3$ with $R^4$, $R^4$ with $R^6$, and/or $R^5$ with $R^6$ combined as an aromatic ring, $C_5$ or $C_6$ cycloalkene, or $C_5$ or $C_6$ cycloalkadiene, and where each of $R^2$, $R^3$, $R^4$, $R^5$, and $R^6$ is combined only once;

wherein one or more of $R^2$ with $R^3$, $R^2$ with $R^4$, $R^2$ with $R^6$, $R^3$ with $R^5$, $R^3$ with $R^6$, and $R^4$ with $R^5$ are optionally combined as a sigma bond, or $C_1$ to $C_4$ alkylene chain where one of the carbons is optionally replaced with an oxygen and where each of $R^2$, $R^3$, $R^4$, $R^5$, and $R^6$ is combined only once; and/or wherein $R^4R^{4'}C$, $R^5R^{5'}C$ or $R^6R^{6'}C$ are optionally replaced with an oxygen; and wherein any of the previous said alkyl alkadienyl, alkatrienyl, cycloalkyl, cycloalkenyl, alkoxy, phenoxy, aromatic ring, and alkylene chain is optionally substituted with one or more $C_1$ to $C_4$ alkyl, $C_1$ to $C_4$ alkoxy, $C_3$ to $C_6$ cycloalkyl, $C_3$ to $C_6$ cycloalkenyl, phenyl, acetyl, or nitro groups; and wherein $R^8$ is H, phenyl or the oxygen of an oxo group, $R^9$, $R^{10}$, and $R^{11}$ are independently $CH_2X$, $C_1$ to $C_{12}$ alkyl, or phenyl, or wherein $R^9$ and $R^{10}$ are combined as a $C_5$ or $C_6$ cycloalkene or phenyl, wherein X is a leaving group selected from acetoxy, t-butyloxycarbonoxy, Cl, Br, I, trifluroacetoxy, or tosyl, wherein the $C_1$ to $C_{12}$ alkyl of $R^9$-$R^{11}$, the three previous phenyl, or $C_5$ or $C_6$ cycloalkene of $R^9$ and $R^{10}$ are optionally further substituted with one or more Br, Cl, I, $C_1$ to $C_4$ alkoxy, or where two adjacent carbons are substituted by methylenedioxy.

* * * * *